(12) United States Patent
List et al.

(10) Patent No.: US 11,584,787 B2
(45) Date of Patent: Feb. 21, 2023

(54) SOLUBLE CD33 FOR TREATING MYELODYSPLASTIC SYNDROMES (MDS)

(71) Applicant: H. LEE MOFFITT CANCER CENTER AND RESEARCH INSTITUTE, INC., Tampa, FL (US)

(72) Inventors: Alan F. List, Tampa, FL (US); Sheng Wei, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 314 days.

(21) Appl. No.: 16/451,525

(22) Filed: Jun. 25, 2019

(65) Prior Publication Data

US 2020/0055916 A1    Feb. 20, 2020

Related U.S. Application Data

(62) Division of application No. 14/902,719, filed as application No. PCT/US2014/045444 on Jul. 3, 2014, now Pat. No. 10,344,072.

(60) Provisional application No. 61/843,274, filed on Jul. 5, 2013, provisional application No. 61/930,798, filed on Jan. 23, 2014, provisional application No. 61/931,366, filed on Jan. 24, 2014, provisional application No. 61/978,009, filed on Apr. 10, 2014.

(51) Int. Cl.

| | | |
|---|---|---|
| *A61K 38/17* | (2006.01) | |
| *A61K 47/00* | (2006.01) | |
| *A61K 47/50* | (2017.01) | |
| *C07K 14/705* | (2006.01) | |
| *C07K 14/735* | (2006.01) | |
| *C07K 19/00* | (2006.01) | |
| *A61K 47/69* | (2017.01) | |
| *G01N 33/68* | (2006.01) | |
| *A61K 38/00* | (2006.01) | |

(52) U.S. Cl.
CPC ...... *C07K 14/70503* (2013.01); *A61K 38/177* (2013.01); *A61K 38/1774* (2013.01); *A61K 47/6913* (2017.08); *C07K 14/705* (2013.01); *C07K 14/70596* (2013.01); *C07K 19/00* (2013.01); *G01N 33/6872* (2013.01); *A61K 38/00* (2013.01); *A61K 47/6911* (2017.08); *C07K 14/70535* (2013.01); *C07K 2319/00* (2013.01); *C07K 2319/30* (2013.01); *C07K 2319/32* (2013.01); *C07K 2319/70* (2013.01); *G01N 2333/4727* (2013.01); *G01N 2333/70503* (2013.01); *G01N 2500/02* (2013.01)

(58) Field of Classification Search
CPC .............. C07K 14/00; C07K 14/70503; C07K 14/70596; C07K 14/71; C07K 14/705; C07K 14/70535; C07K 14/715; C07K 19/00; A61K 38/1774; A61K 38/179; A61K 38/1793; A61K 38/17; A61K 38/177
See application file for complete search history.

(56) References Cited

U.S. PATENT DOCUMENTS

| | | | |
|---|---|---|---|
| 3,610,795 A | 10/1971 | Antoine | |
| 5,620,689 A | 4/1997 | Allen et al. | |
| 2004/0033603 A1 | 2/2004 | Zhang | |
| 2006/0241040 A1* | 10/2006 | Visintin | ............... C07K 14/705 424/140.1 |
| 2009/0297521 A1 | 12/2009 | Fey et al. | |
| 2010/0166775 A1 | 7/2010 | Bjork et al. | |
| 2010/0331250 A1* | 12/2010 | Zhou | ..................... C07K 14/71 514/8.1 |
| 2012/0082670 A1 | 4/2012 | Konopitzky et al. | |
| 2012/0251554 A1 | 10/2012 | Bachmann et al. | |

FOREIGN PATENT DOCUMENTS

| | | |
|---|---|---|
| EP | 1736482 | 12/2006 |
| JP | 2009517404 | 4/2009 |
| WO | 9802540 | 1/1998 |
| WO | 2004043344 | 5/2004 |
| WO | 2004063351 | 7/2004 |
| WO | 2007001332 | 1/2007 |
| WO | 2007084253 | 7/2007 |
| WO | 2007146959 | 12/2007 |
| WO | 2008/131908 | 11/2008 |
| WO | 2008157378 | 12/2008 |
| WO | 2012083370 | 6/2012 |

OTHER PUBLICATIONS

Arbour et al. TLR4 mutations are associated with endotoxin hyporesponsiveness in humans. Nature Genetics 25: 187-191, 2000.*
Cull et al. Biotinylation of proteins in vivo and in vitro using small peptide tags. Methods Enzymol 326: 430-440, 2000.*
Osawa et al. De—N-glycosylation or G28S mutation of RAGE sensitizes its interaction with advanced glycation endproducts. Biochim Biophys Acta 1770: 1468-1474, 2007.*
R&D Systems Datasheet for recombinant human RAGE Fc chimera Catalog No. 1145-RG; Feb. 6, 2018.*
UniProtKB/Swiss-Prot Q15109, Nov. 1, 1997; 11 total pages.*
Office Action issued for Canadian Application No. 2,917,485, dated Jul. 2, 2020.
Extended European Search Report issued for European Application No. 20150607.8, dated Jul. 16, 2020.

(Continued)

*Primary Examiner* — Bridget E Bunner
(74) *Attorney, Agent, or Firm* — Meunier Carlin & Curfman LLC

(57) ABSTRACT

Disclosed are compositions and methods for treating disease or condition caused or exacerbated by S100A9 activity, such as myelodysplastic syndromes (MDS) using a composition comprising an effective amount of a CD33/S100A9 inhibitor.

16 Claims, 43 Drawing Sheets

Specification includes a Sequence Listing.

(56) References Cited

OTHER PUBLICATIONS

Examination report No. 1 issued for Australian Application No. 2018205105, dated May 14, 2019.
Office Action issued for Japanese Application No. 2019-171342, dated Aug. 18, 2020. English Translation included.
Brinkman-Van der Linden, E.C. and Varki, A., "New Aspects of Siglec Binding Specificities, Including the Significance of Fucosylation and of the sialyl-Tn Epitope. Sialic Acid-Binding Immunoglobulin Superfamily Lectins", Journal of Biological Chemistry, 275/12, pp. 8625-8632, doi: 10.1074/jbc.275.12.8625., Mar. 24, 2000 (Mar. 24, 2000).
Allampallam, K., et al. 2002. Biological significance of proliferation, apoptosis, cytokines, and monocyte/macrophage cells in bone marrow biopsies of 145 patients with myelodysplastic syndrome. Int J Hematol 75:289-297.
Angata, T., et al., 2006, Discovery of Siglec-14, a novel sialic acid receptor undergoing concerted evolution with Siglec-5 in primates. Faseb J, 20:1964-1973.
Araki, H., et al., 2004, Reprogramming of human postmitotic neutrophils into macrophages by growth factors. Blood 103:2973-2980.
Avril, T., et al., 2004, The membrane-proximal immunoreceptor tyrosine-based inhibitory motif is critical for the inhibitory signaling mediated by Siglecs-7 and -9, CD33-related Siglecs expressed on human monocytes and NK cells. J Immunol 173:6841-6849.
Bandow, K., et al. 2010. Molecular mechanisms of the inhibitory effect of lipopolysaccharide (LPS) on osteoblast differentiation. Biochem Biophys Res Commun 402:755-761.
Bellamy, W.T., et al. 2001. Vascular endothelial cell growth factor is an autocrine promoter of abnormal localized immature myeloid precursors and leukemia progenitor formation in myelodysplastic syndromes. Blood 97:1427-1434.
Blasius, A.L., et al., 2006, Sampling and signaling in plasmacytoid dendritic cells: the potential roles of Siglec-H. Trends Immunol 27:255-260.
Blasius, A.L., et al., 2006, Siglec-H is an IPC-specific receptor that modulates type I IFN secretion through DAP12. Blood 107:2474-2476.
Cannon, J.P., et al., 2008, A bony fish immunological receptor of the NITR multigene family mediates allogeneic recognition. Immunity 29:228-237.
Cannon, J.P., et al., 2011, Construction, expression, and purification of chimeric protein reagents based on immunoglobulin fc regions. Methods Mol Biol 748:51-67.
Cannon, J.P., et al., 2012, Specific lipid recognition is a general feature of CD300 and TREM molecules. Immunogenetics 64:39-47.
Chen, X., et al., 2008, A critical role for DAP10 and DAP12 in CD8+ T cell-mediated tissue damage in large granular lymphocyte leukemia. Blood, 113(14):3226-34.
Cheng, P., et al., 2008, Inhibition of dendritic cell differentiation and accumulation of myeloid-derived suppressor cells in cancer is regulated by S100A9 protein. J Exp Med, 205:2235-2249.
Crocker, P. R., et al., 2007, Siglecs and their roles in the immune system. Nat Rev Immunol 7:255-266.
De Luca, K., et al. 2009. The TLR1/2 agonist PAM(3)CSK(4) instructs commitment of human hematopoietic stem cells to a myeloid cell fate. Leukemia 23:2063-2074.
Dykstra, B., et al. 2011. Clonal analysis reveals multiple functional defects of aged murine hematopoietic stem cells. J Exp Med 208:2691-2703.
Ehrchen, J.M., et al., 2009, The endogenous Toll-like receptor 4 agonist S100A8/S100A9 (calprotectin) as innate amplifier of infection, autoimmunity, and cancer. J Leukoc Biol 86:557-566.
Fang, J., et al. 2012 Cytotoxic effects of bortezomib in myelodysplastic syndrome/acute myeloid leukemia depend on autophagy-mediated lysosomal degradation of TRAF6 and repression of PSMA1. Blood 120:858-867.
Gabrilovich, D.I., et al., 2009, Myeloid-derived suppressor cells as regulators of the immune system. Nat Rev Immunol 9:162-174.
Gondek, L.P., et al., 2008, Chromosomal lesions and uniparental disomy detected by SNP arrays in MDS, MDS/MPD, and MDS-derived AML. Blood 111:1534-1542.
Hamerman, J.A., et al., 2006, Cutting edge: inhibition of TLR and FcR responses in macrophages by triggering receptor expressed on myeloid cells (TREM)-2 and DAP12. J Immunol 177:2051-2055.
Hofmann, W.K., et al., 2002, Characterization of gene expression of CD34+ cells from normal and myelodysplastic bone marrow. Blood 100:3553-3560.
Ikehara, Y. et al., 2004, Negative regulation of T cell receptor signaling by Siglec-7 (p70/AIRM) and Siglec-9. J Biol Chem 279:43117-43125.
International Search Report and Written Opinion, International Application No. PCT/US14/45444, dated Jan. 12, 2015.
Kristinsson, S.Y., et al., 2011, Chronic immune stimulation might act as a trigger for the development of acute myeloid leukemia or myelodysplastic syndromes. J Clin Oncol 29:2897-2903.
Kusmartesev, S., et al., 2006. Role of immature myeloid cells in mechanisms of immune evasion in cancer. Cancer Immunol Immunother 55:237-245.
Lajaunias, F., et al., 2005 Constitutive repressor activity of CD33 on human monocytes requires sialic acid recognition and phosphoinositide 3-kinase-mediated intracellular signaling. Eur J Immunol, 35:243-251.
Lanier, L.L., 2005, NK cell recognition. Annu Rev Immunol, 23:225-274.
Lanier, L.L., et al., 1998, Immunoreceptor DAP12 bearing a tyrosine-based activation motif is involved in activating NK cells. Nature, 391:703-707.
Mantiz, M.P., et al., 2003, Loss of S100A9 (MRP14) results in reduced interleukin-8-induced CD11b surface expression, a polarized microfilament system, and diminished responsiveness to chemoattractants in vitro. Mol Cell Biol, 23:1034-1043.
Maratheftis, C.I., et al. 2007. Toll-like receptor-4 is up-regulated in hematopoietic progenitor cells and contributes to increased apoptosis in myelodysplastic syndromes. Clin Cancer Res 13:1154-1160.
Mirza, N. et al., 2006, All-trans-retinoic acid improves differentiation of myeloid cells and immune response in cancer patients. Cancer Res, 66:9299-9307.
Navas, T., et al. 2008. Inhibition of p38alpha MAPK disrupts the pathological loop of proinflammatory factor production in the myelodysplastic syndrome bone marrow microenvironment. Leuk Lymphoma 49:1963-1975.
Nefedova, Y., et al., 2007, Mechanism of all-trans retinoic acid effect on tumor-associated myeloid-derived suppressor cells. Cancer Res 67:11021-11028.
Nutku, E., et al., 2003, Ligation of Siglec-8: a selective mechanism for induction of human eosinophil apoptosis. Blood 101:5014-5020.
Ostrand-Rosenberg, S., et al., 2009, Myeloid-derived suppressor cells: linking inflammation and cancer. J Immunol 182:4499-4506.
Paul, S.P., et al., 2000, Myeloid specific human CD33 is an inhibitory receptor with differential ITIM function in recruiting the phosphatases SHP-1 and SHP-2. Blood 96:483-490.
Raaijmakers, M.H., et al., 2010, Bone progenitor dysfunction induces myelodysplasia and secondary leukaemia. Nature, 464:852-857.
Ravetch, J.V., et al., 2000, Immune inhibitory receptors. Science 290:84-89.
Raza et al., 1995, Apoptosis in bone marrow biopsy samples involving stromal and hematopoietic cells in 50 patients with myelodysplastic syndromes. Blood 86(1):268-276.
Starczynowski, D.T., et al. 2010, Innate immune signaling in the myelodysplastic syndromes. Hematol Oncol Clin North Am 24:343-359.
Starczynowski, D.T., et al., 2008, High-resolution whole genome tiling path array CGH analysis of CD34+ cells from patients with low-risk myelodysplastic syndromes reveals cryptic copy number alterations and predicts overall and leukemia-free survival. Blood 112:3412-3424.
Starczynowski, D.T., et al., 2010 Identification of miR-145 and miR-146a as mediators of the 5q- syndrome phenotype. Nat Med 16:49-58.

(56) References Cited

OTHER PUBLICATIONS

Stirewalt, D.L., et al. 2008. Tumour necrosis factor-induced gene expression in human marrow stroma: clues to the pathophysiology of MDS? Br J Haematol 140:444-453.
Takizawa, H., et al. 2012. Demand-adapted regulation of early hematopoiesis in infection and inflammation. Blood 119:2991-3002.
Talmadge, J.E., 2007, Pathways mediating the expansion and immunosuppressive activity of myeloid-derived suppressor cells and their relevance to cancer therapy. Clin Cancer Res 13:5243-5248.
Talmadge, J.E., et al., 2007 Inflammatory cell infiltration of tumors: Jekyll or Hyde. Cancer Metastasis Rev 26:373-400.
Turnbull, I.R., et al., 2007, Activating and inhibitory functions of DAP12. Nat Rev Immunol 7:155-161.
Ulyanova, T., et al., 2001, Molecular cloning of MIS, a myeloid inhibitory siglec, that binds protein-tyrosine phosphatases SHP-1 and SHP-2. J Biol Chem, 276:14451-14458.
Verschoor C.P., et al., 2013, Blood CD33(+)HLA-DR(-) myeloid-derived suppressor cells are increased with age and a history of cancer. J Leukoc Biol 93(4):633-7.
Viemann, D., et al. 2007. MRP8/MRP14 impairs endothelial integrity and induces a caspase-dependent and -independent cell death program. Blood 109:2453-2460.
Vogl, T., et al., 2007. Mrp8 and Mrp14 are endogenous activators of Toll-like receptor 4, promoting lethal, endotoxin-induced shock. Nat Med 13:1042-1049.
Von Gunten, S., et al., 2008, Basic and clinical immunology of Siglecs. Ann NY Acad Sci 1143:61-82.
Wei, S. et al., 2009, A critical role for phosphatase haplodeficiency in the selective suppression of deletion 5q MDS by lenalidomide. Proc Natl Acad Sci USA, 106:12974-12979.
Xu, S., et al., 2010, An improved harvest and in vitro expansion protocol for murine bone marrow-derived mesenchymal stem cells. J Biomed Biotechnol, 2010:105940.
Youn, J.I., et al., 2008, Subsets of myeloid-derived suppressor cells in tumor-bearing mice. J Immunol 181:5791-5802.
E.C.M. Brinkman-Van Der Linden et al., "CD33/Siglec-3 Binding Specificity, Expression Pattern, and Consequences of Gene Deletion in Mice", Molecular and Cellular Biology, vol. 23, No. 12, Jun. 15, 2003, pp. 4199-4206.
N. Cheng et al., "Cutting Edge: TLR2 Is a Functional Receptor for Acute-Phase Serum Amyloid A", The Journal of Immunology, vol. 181, No. 1, Jul. 1, 2008, pp. 22-26.
Xianghong Chen, et al., "Induction of myelodysplasia by myeloid-derived suppressor cells", Journal of Clinical Invesitgation, vol. 123, No. 11, Oct. 15, 2013, pp. 4595-4611.
Wei Sheng et al., "Microenvironment Induced Myeoldysplastic Syndrome (MDS) in S100A9 Transgenic Mice Caused by Myeloid-Derived Suppressor Cells (MDSC)", Blood, vol. 118, No. 21, Nov. 2011, p. 358.
Daniel M. Czajkowsky et al., "Fc-fusion proteins: new developments and future perspectives", EMBO Molecular Medicine, vol. 4, No. 10, Jul. 26, 2012, pp. 1015-1028.
European Search Report issued in European Application No. 14819813.8, dated Dec. 9, 2016.
Markowitz et al., "Review of S100A9 biology and its role in cancer.", Biochim Biophys Acta, (2013), vol. 1835, No. 1, pp. 100-109.
Freeman, S. D. et al. "Characterization of CD33 as a New Member of the Sialoadhesin Family of Cellular Interaction Molecules", Blood, 1995, vol. 85, No. 8, pp. 2005-2012.
Examination Report issued in Australian Application No. 2014285079, dated Jul. 13, 2017.
Ebert, B. et al. "An RNA interference model of RPS19 deficiency in Diamond-Blackfan anemia recapitulates defective hematopoiesis and rescue by dexamethasone: identification of dexamethasone-responsive genes by microarray", Blood Jun. 15, 2005;105(12):4620-6.
Ferrajoli, A. et al. "Thrombopoietin stimulates myelodysplastic syndrome granulocyte-macrophage and erythroid progenitor proliferation", Leukemia & Lymphoma (1998) 30:3-4, 279-292.
Narla, A. et al. "Dexamethasone and lenalidomide have distinct functional effects on Erythropoiesis", Blood. Aug. 25, 2011;118(8):2296-304.
Pessina, A et al. "Prevalidation of a model for predicting acute neutropenia by colony forming unit granulocyte/macrophage (CFU-GM) assay", Toxicol In Vitro (2001) 15(6):729-40.
Pessina, A et al. "Application of the CFU-GM assay to predict acute drug-induced neutropenia: an international blind trial to validate a prediction model for the maximum tolerated dose (MTD) of myelosuppressive xenobiotics", Toxicol Sci (2003) 75(2):355-67.
Von Lindern, M. et al. "The glucocorticoid receptor cooperates with the erythropoietin receptor and c-Kit to enhance and sustain proliferation of erythroid progenitors in vitro". Blood (1999) 94(2):550-559.
Zhou, L. et al. "Inhibition of the TGF-beta receptor I kinase promotes hematopoiesis in MDS", Blood (2008) 112(8):3434-43.
Communication Pursuant to Article 94(3) EPC, issued for European Application No. 14819813.8, dated May 29, 2018.
Communication Pursuant to Article 94(3) EPC, issued for European Application No. 14819813.8, dated Jan. 28, 2019.
Basiorka et al., Blood 128(25):2960-2975, 2016.
Bjork et al., PLOS Biology 7(4):800-812, 2009.
Bejar et al. Recent developments in myelodysplastic syndromes. Blood 124(18): 2793-2803, 2014.
Bork, A. Powers and pitfalls in sequence analysis: the 70% hurdle. Genome Res 10: 398-400, 2000.
Bork et al. Go hunting in sequence databases but watch out for the traps. Trends in Genetics. 12(10): 425-427, 1996.
Brenner, S.E. Errors in genome function. Trends in Genetics 15(4): 132-133, 1999.
Doerks et al. Protein annotation: detective work for function prediction. Trends in Genetics 14(6): 248-250, 1998.
Greenberg et al. Myelodysplastic syndromes. J National Comprehensive Cancer Network 11(7): 838-874, 2013.
Malcovati et al. Diagnosis and treatment of primary myelodysplastic syndromes in adults: recommendations from the European Leuekmia Net. Blood 122(17): 2943-2964, 2013.
Marks, Alexandra Jane. Targeting of Cytotoxic Peptides to Haematological Malignancies. Diss. University of London, 2005.
Ngo et al. Computational complexity, protein structure prediction, and the Levinthal paradox. The Protein Folding Problem and Tertiary Structure Prediction, pp. 492-495, 1994.
Skolnick et al. From genes to protein structure and function: novel applications of computational approaches in the genomic era. Trends in Biotech 18(1): 34-39, 2000.
Smith et al. The challenges of genome sequence annotation or "The devil is in the details". Nature Biotech 15: 1222-1223, 1997.
Tchilian, Elma Zaven. Functional Analysis of Myloid Cell Antigens. Diss. University College London, 1994.
Tefferi et al. Myelodysplastic syndromes. N Engl J Med 361: 1872-1885, 2009.
Tokuriki et al. Stability effects of mutations and protein evolvability. Curr Opin Structural Biol 19: 596-604, 2009.
Walter, Roland Bruno. Mechanisms of Endocytosis of CD33/Siglec-33: Role of ITIMs, Tyrosine Phosphorylation, and Monoubiquitylation. Diss. University of Washington, 2006.
Wells. J.A. Additivity of mutational effects in proteins. Biochemistry 29 (37): 8509-8517, 1990.

* cited by examiner

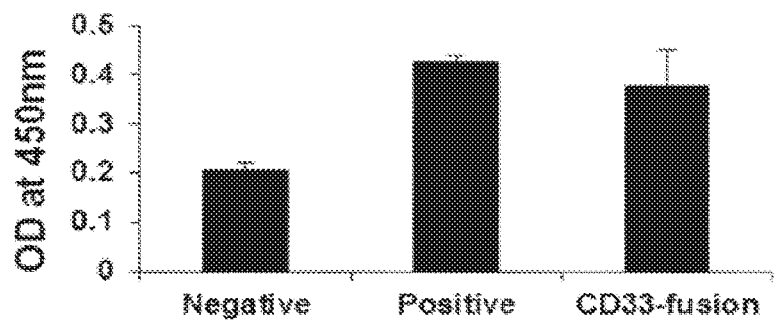
*FIGURE 3C*
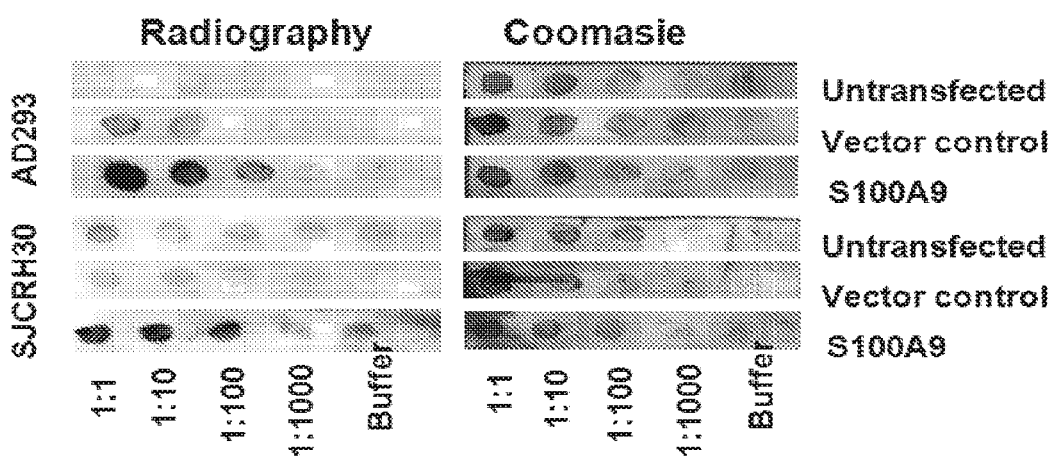
*FIGURE 3D*
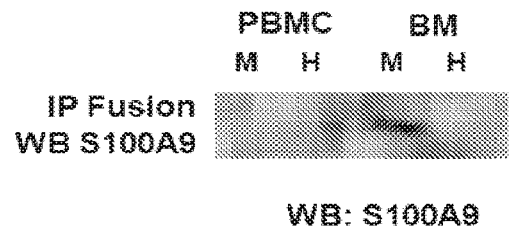
*FIGURE 3E – 3F*

SEQUENCE LISTING

<160> NUMBER OF SEQ ID NOS: 9

<210> SEQ ID NO 1
<211> LENGTH: 242
<212> TYPE: PRT
<213> ORGANISM: Artificial Sequence
<220> FEATURE:
<223> OTHER INFORMATION: Syntethic construct

<400> SEQUENCE: 1

```
Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220
```

```
Ile Phe Pro Gly Asp Gly Ser Gly Lys Gln Glu Thr Arg Ala Gly Val
225                 230                 235                 240

Val His
```

<210> SEQ ID NO 2
<211> LENGTH: 242
<212> TYPE: PRT
<213> ORGANISM: Artificial Sequence
<220> FEATURE:
<223> OTHER INFORMATION: Syntethic construct
<220> FEATURE:
<221> NAME/KEY: MISC_FEATURE
<222> LOCATION: (5)..(5)
<223> OTHER INFORMATION: Xaa is Trp or Arg
<220> FEATURE:
<221> NAME/KEY: MISC_FEATURE
<222> LOCATION: (52)..(52)
<223> OTHER INFORMATION: Xaa is Arg or Gly
<220> FEATURE:
<221> NAME/KEY: MISC_FEATURE
<222> LOCATION: (111)..(111)
<223> OTHER INFORMATION: Xaa is Ser or Asn

<400> SEQUENCE: 2

```
Asp Pro Asn Phe Xaa Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Xaa Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Xaa Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His
```

<210> SEQ ID NO 3
<211> LENGTH: 122
<212> TYPE: PRT
<213> ORGANISM: Artificial Sequence

```
<220> FEATURE:
<223> OTHER INFORMATION: Syntethic construct

<400> SEQUENCE: 3

Pro Asn Phe Trp Leu Gln Val Gln Glu Ser Val Thr Val Gln Glu Gly
1               5                   10                  15

Leu Cys Val Leu Val Pro Cys Thr Phe Phe His Pro Ile Pro Tyr Tyr
            20                  25                  30

Asp Lys Asn Ser Pro Val His Gly Tyr Trp Phe Arg Glu Gly Ala Ile
        35                  40                  45

Ile Ser Arg Asp Ser Pro Val Ala Thr Asn Lys Leu Asp Gln Glu Val
    50                  55                  60

Gln Glu Glu Thr Gln Gly Arg Phe Arg Leu Leu Gly Asp Pro Ser Arg
65                  70                  75                  80

Asn Asn Cys Ser Leu Ser Ile Val Asp Ala Arg Arg Asp Asn Gly
                85                  90                  95

Ser Tyr Phe Phe Arg Met Glu Arg Gly Ser Thr Lys Tyr Ser Tyr Lys
            100                 105                 110

Ser Pro Gln Leu Ser Val His Val Thr Asp
            115                 120

<210> SEQ ID NO 4
<211> LENGTH: 122
<212> TYPE: PRT
<213> ORGANISM: Artificial Sequence
<220> FEATURE:
<223> OTHER INFORMATION: Syntethic construct
<220> FEATURE:
<221> NAME/KEY: MISC_FEATURE
<222> LOCATION: (4)..(4)
<223> OTHER INFORMATION: Xaa is Trp or Arg
<220> FEATURE:
<221> NAME/KEY: MISC_FEATURE
<222> LOCATION: (51)..(51)
<223> OTHER INFORMATION: Xaa is Arg or Gly
<220> FEATURE:
<221> NAME/KEY: MISC_FEATURE
<222> LOCATION: (110)..(110)
<223> OTHER INFORMATION: Xaa is Ser or Asn

<400> SEQUENCE: 4

Pro Asn Phe Xaa Leu Gln Val Gln Glu Ser Val Thr Val Gln Glu Gly
1               5                   10                  15

Leu Cys Val Leu Val Pro Cys Thr Phe Phe His Pro Ile Pro Tyr Tyr
            20                  25                  30

Asp Lys Asn Ser Pro Val His Gly Tyr Trp Phe Arg Glu Gly Ala Ile
        35                  40                  45

Ile Ser Xaa Asp Ser Pro Val Ala Thr Asn Lys Leu Asp Gln Glu Val
    50                  55                  60

Gln Glu Glu Thr Gln Gly Arg Phe Arg Leu Leu Gly Asp Pro Ser Arg
65                  70                  75                  80

Asn Asn Cys Ser Leu Ser Ile Val Asp Ala Arg Arg Asp Asn Gly
                85                  90                  95

Ser Tyr Phe Phe Arg Met Glu Arg Gly Ser Thr Lys Tyr Xaa Tyr Lys
            100                 105                 110

Ser Pro Gln Leu Ser Val His Val Thr Asp
            115                 120
```

-continued

```
<210> SEQ ID NO 5
<211> LENGTH: 608
<212> TYPE: PRT
<213> ORGANISM: Artificial Sequence
<220> FEATURE:
<223> OTHER INFORMATION: Syntethic construct

<400> SEQUENCE: 5

Glu Ser Trp Glu Pro Cys Val Glu Val Val Pro Asn Ile Thr Tyr Gln
1               5                   10                  15

Cys Met Glu Leu Asn Phe Tyr Lys Ile Pro Asp Asn Leu Pro Phe Ser
            20                  25                  30

Thr Lys Asn Leu Asp Leu Ser Phe Asn Pro Leu Arg His Leu Gly Ser
        35                  40                  45

Tyr Ser Phe Phe Ser Phe Pro Glu Leu Gln Val Leu Asp Leu Ser Arg
    50                  55                  60

Cys Glu Ile Gln Thr Ile Glu Asp Gly Ala Tyr Gln Ser Leu Ser His
65                  70                  75                  80

Leu Ser Thr Leu Ile Leu Thr Gly Asn Pro Ile Gln Ser Leu Ala Leu
                85                  90                  95

Gly Ala Phe Ser Gly Leu Ser Ser Leu Gln Lys Leu Val Ala Val Glu
            100                 105                 110

Thr Asn Leu Ala Ser Leu Glu Asn Phe Pro Ile Gly His Leu Lys Thr
        115                 120                 125

Leu Lys Glu Leu Asn Val Ala His Asn Leu Ile Gln Ser Phe Lys Leu
    130                 135                 140

Pro Glu Tyr Phe Ser Asn Leu Thr Asn Leu Glu His Leu Asp Leu Ser
145                 150                 155                 160

Ser Asn Lys Ile Gln Ser Ile Tyr Cys Thr Asp Leu Arg Val Leu His
                165                 170                 175

Gln Met Pro Leu Leu Asn Leu Ser Leu Asp Leu Ser Leu Asn Pro Met
            180                 185                 190

Asn Phe Ile Gln Pro Gly Ala Phe Lys Glu Ile Arg Leu His Lys Leu
        195                 200                 205

Thr Leu Arg Asn Asn Phe Asp Ser Leu Asn Val Met Lys Thr Cys Ile
    210                 215                 220

Gln Gly Leu Ala Gly Leu Glu Val His Arg Leu Val Leu Gly Glu Phe
225                 230                 235                 240

Arg Asn Glu Gly Asn Leu Glu Lys Phe Asp Lys Ser Ala Leu Glu Gly
                245                 250                 255

Leu Cys Asn Leu Thr Ile Glu Glu Phe Arg Leu Ala Tyr Leu Asp Tyr
            260                 265                 270

Tyr Leu Asp Asp Ile Ile Asp Leu Phe Asn Cys Leu Thr Asn Val Ser
        275                 280                 285

Ser Phe Ser Leu Val Ser Val Thr Ile Glu Arg Val Lys Asp Phe Ser
    290                 295                 300

Tyr Asn Phe Gly Trp Gln His Leu Glu Leu Val Asn Cys Lys Phe Gly
305                 310                 315                 320

Gln Phe Pro Thr Leu Lys Leu Lys Ser Leu Lys Arg Leu Thr Phe Thr
                325                 330                 335

Ser Asn Lys Gly Gly Asn Ala Phe Ser Glu Val Asp Leu Pro Ser Leu
            340                 345                 350

Glu Phe Leu Asp Leu Ser Arg Asn Gly Leu Ser Phe Lys Gly Cys Cys
        355                 360                 365
```

-continued

Ser Gln Ser Asp Phe Gly Thr Thr Ser Leu Lys Tyr Leu Asp Leu Ser
        370                 375                 380

Phe Asn Gly Val Ile Thr Met Ser Ser Asn Phe Leu Gly Leu Glu Gln
385                 390                 395                 400

Leu Glu His Leu Asp Phe Gln His Ser Asn Leu Lys Gln Met Ser Glu
                405                 410                 415

Phe Ser Val Phe Leu Ser Leu Arg Asn Leu Ile Tyr Leu Asp Ile Ser
            420                 425                 430

His Thr His Thr Arg Val Ala Phe Asn Gly Ile Phe Asn Gly Leu Ser
        435                 440                 445

Ser Leu Glu Val Leu Lys Met Ala Gly Asn Ser Phe Gln Glu Asn Phe
    450                 455                 460

Leu Pro Asp Ile Phe Thr Glu Leu Arg Asn Leu Thr Phe Leu Asp Leu
465                 470                 475                 480

Ser Gln Cys Gln Leu Glu Gln Leu Ser Pro Thr Ala Phe Asn Ser Leu
                485                 490                 495

Ser Ser Leu Gln Val Leu Asn Met Ser His Asn Asn Phe Phe Ser Leu
            500                 505                 510

Asp Thr Phe Pro Tyr Lys Cys Leu Asn Ser Leu Gln Val Leu Asp Tyr
        515                 520                 525

Ser Leu Asn His Ile Met Thr Ser Lys Lys Gln Glu Leu Gln His Phe
    530                 535                 540

Pro Ser Ser Leu Ala Phe Leu Asn Leu Thr Gln Asn Asp Phe Ala Cys
545                 550                 555                 560

Thr Cys Glu His Gln Ser Phe Leu Gln Trp Ile Lys Asp Gln Arg Gln
                565                 570                 575

Leu Leu Val Glu Val Glu Arg Met Glu Cys Ala Thr Pro Ser Asp Lys
            580                 585                 590

Gln Gly Met Pro Val Leu Ser Leu Asn Ile Thr Cys Gln Met Asn Lys
        595                 600                 605

<210> SEQ ID NO 6
<211> LENGTH: 320
<212> TYPE: PRT
<213> ORGANISM: Artificial Sequence
<220> FEATURE:
<223> OTHER INFORMATION: Syntethic construct

<400> SEQUENCE: 6

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg Val Tyr
                85                  90                  95

Gln Ile Pro Gly Lys Pro Glu Ile Val Asp Ser Ala Ser Glu Leu Thr
            100                 105                 110

```
Ala Gly Val Pro Asn Lys Val Thr Cys Val Ser Glu Gly Ser Tyr
            115                 120                 125

Pro Ala Gly Thr Leu Ser Trp His Leu Asp Gly Lys Pro Leu Val Pro
        130                 135                 140

Asn Glu Lys Gly Val Ser Val Lys Glu Gln Thr Arg Arg His Pro Glu
145                 150                 155                 160

Thr Gly Leu Phe Thr Leu Gln Ser Glu Leu Met Val Thr Pro Ala Arg
                165                 170                 175

Gly Gly Asp Pro Arg Pro Thr Phe Ser Cys Ser Phe Ser Pro Gly Leu
                180                 185                 190

Pro Arg His Arg Ala Leu Arg Thr Ala Pro Ile Gln Pro Arg Val Trp
        195                 200                 205

Glu Pro Val Pro Leu Glu Glu Val Gln Leu Val Val Glu Pro Glu Gly
    210                 215                 220

Gly Ala Val Ala Pro Gly Gly Thr Val Thr Leu Thr Cys Glu Val Pro
225                 230                 235                 240

Ala Gln Pro Ser Pro Gln Ile His Trp Met Lys Asp Gly Val Pro Leu
                245                 250                 255

Pro Leu Pro Pro Ser Pro Val Leu Ile Leu Pro Glu Ile Gly Pro Gln
            260                 265                 270

Asp Gln Gly Thr Tyr Ser Cys Val Ala Thr His Ser Ser His Gly Pro
        275                 280                 285

Gln Glu Ser Arg Ala Val Ser Ile Ser Ile Ile Glu Pro Gly Glu Glu
    290                 295                 300

Gly Pro Thr Ala Gly Ser Val Gly Gly Ser Gly Leu Gly Thr Leu Ala
305                 310                 315                 320

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Gly Leu Asn Asp Ile Phe Glu Ala Gln Lys Ile Glu Trp His Glu
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Asp Ile Glu Gly Arg Met Asp
1               5

<210> SEQ ID NO 9
<211> LENGTH: 8
<212> TYPE: PRT
<213> ORGANISM: Artificial Sequence
<220> FEATURE:
<223> OTHER INFORMATION: Syntethic construct

<400> SEQUENCE: 9

Asp Tyr Lys Asp Asp Asp Asp Lys
1               5
```

SOLUBLE CD33 FOR TREATING MYELODYSPLASTIC SYNDROMES (MDS)

CROSS-REFERENCE TO RELATED APPLICATIONS

This application is divisional application of U.S. application Ser. No. 14/902,719, filed Jan. 4, 2016, which is a national stage application filed under 35 U.S.C. § 371 of PCT/US2014/045444 filed Jul. 3, 2014, which claims benefit of U.S. Provisional Application No. 61/843,274, filed Jul. 5, 2013, U.S. Provisional Application No. 61/930,798, filed Jan. 23, 2014, U.S. Provisional Application No. 61/931,366, filed Jan. 24, 2014, and U.S. Provisional Application No. 61/978,009, filed Apr. 10, 2014, which are hereby incorporated herein by reference in their entirety.

STATEMENT REGARDING FEDERALLY SPONSORED RESEARCH OR DEVELOPMENT

This invention was made with Government Support under Grant No. CA131076 and Grant No. AI056213 awarded by the National Institutes of Health. The Government has certain rights in the invention.

REFERENCE TO SEQUENCE LISTING

The Sequence Listing submitted Nov. 5, 2019, as a text file named "10645-002US2_2019_11_05_ST25.txt," created on Jun. 1, 2018, and having a size of 16,287 bytes is hereby incorporated by reference pursuant to 37 C.F.R. § 1.52(e)(5).

BACKGROUND

Myelodysplastic syndromes (MDS) are hematopoietic stem cell malignancies with a rising prevalence owing to the aging of the American population. MDS comprise a group of malignant hematologic disorders associated with impaired erythropoiesis, dysregulated myeloid differentiation and increased risk for acute myeloid leukemia (AML) transformation. The incidence of MDS is increasing with 15,000 to 20,000 new cases each year in the United States and large numbers of patients requiring chronic blood transfusions. Ineffective erythropoiesis remains the principal therapeutic challenge for patients with more indolent subtypes, driven by a complex interplay between genetic abnormalities intrinsic to the MDS clone and senescence dependent inflammatory signals within the bone marrow (BM) microenvironment. Although three agents are approved for the treatment of MDS in the United States (US), lenalidomide (LEN) represents the only targeted therapeutic. Treatment with LEN yields sustained red blood cell transfusion independence accompanied by partial or complete resolution of cytogenetic abnormalities in the majority of patients with a chromosome 5q deletion (del5q), whereas only a minority of patients with non-del5q MDS achieve a meaningful response, infrequently accompanied by cytogenetic improvement. Although responses in patients with del5q MDS are relatively durable, lasting a median of 2.5 years, resistance emerges over time with resumption of transfusion dependence.

SUMMARY

It is shown herein that CD33+ myeloid-derived suppressor cells (MDSCs) specifically accumulate in the BM of MDS patients and impair hematopoiesis through a mechanism that involves S100A9 as an endogenous ligand for CD33 initiated signaling. Therefore, disclosed are compositions and methods for treating MDS that generally involve administering an effective amount of a CD33/S100A9 antagonist to inhibit activation of MDSCs. For example, the method can involve administering to the subject a therapeutically effective amount of a composition comprising an agent that binds and sequesters S100A9.

In some embodiments, the CD33/S100A9 antagonist binds and sequesters endogenous S100A9 and inhibits its binding to CD33 receptor on MDSCs. Therefore, in some embodiments, the CD33/S100A9 antagonist is a molecule containing a S100A9-binding domain. For example, the CD33/S100A9 antagonist can be a chimeric fusion protein comprising the ectodomain of CD33, Toll like Receptor 4 (TLR4), Receptor for Advanced Glycation End Products (RAGE), or a combination thereof. This ectodomain of CD33, TLR4, and/or RAGE can be any fragment of CD33, TLR4, and/or RAGE capable of binding S100A9. For example, in some cases the CD33 ectodomain contains only the variable region of CD33.

Therefore, disclosed is a recombinant fusion protein comprising an immunoglobulin Fc region; and one, two, three, or more of an extracellular domain of human CD33, extracellular domain of TLR4, extracellular domain of RAGE, or a combination thereof that binds S100A9 protein and is linked by a peptide bond or a peptide linker sequence to the carboxy-terminus of the immunoglobulin Fc region. The fusion protein can further contain a biotin acceptor peptide that can be biotinylated with biotin ligase (BirA) in the presence of biotin and ATP.

In some embodiments, the fusion protein comprises a formula selected from the group consisting of:

eCD33-eTLR4-Fc, eCD33-eRAGE-Fc, eTLR4-eRAGE-Fc, eRAGE-eTLR4-Fc, eCD33-eTLR4-eRAGE-Fc, eCD33-eRAGE-eTLR4-Fc, eTLR4-eCD33-eRAGE-Fc, eRAGE-eCD33-eTLR4-Fc, eTLR4-eRAGE-eCD33-Fc, and eRAGE-eTLR4-eCD33-Fc, wherein "eCD33" is the extracellular domain of human CD33, wherein "eTLR4" is the extracellular domain of TLR4, wherein "eRAGE" is the extracellular domain of RAGE, wherein "Fc" is the immunoglobulin Fc region, and wherein "-" is a peptide linker or a peptide bond.

In some embodiments, the fusion protein comprises a formula selected from the group consisting of:

eCD33-Fc-Avi, eTLR4-Fc-Avi, eRAGE-Fc-Avi, eCD33-eTLR4-Fc-Avi, eCD33-eRAGE-Fc-Avi, eTLR4-eRAGE-Fc-Avi, eRAGE-eTLR4-Fc-Avi, eCD33-eTLR4-eRAGE-Fc-Avi, eCD33-eRAGE-eTLR4-Fc-Avi, eTLR4-eCD33-eRAGE-Fc-Avi, eRAGE-eCD33-Fc-Avi, eTLR4-eRAGE-eCD33Fc-Avi, and eRAGE-eTLR4-eCD33-Fc-Avi wherein "eCD33" is the extracellular domain of human CD33,
wherein "eTLR4" is the extracellular domain of TLR4,
wherein "eRAGE" is the extracellular domain of RAGE,
wherein "Fc" is the immunoglobulin Fc region,
wherein "Avi" is an optional biotin acceptor peptide that can be biotinylated with biotin ligase (BirA) in the presence of biotin and ATP, and
wherein "-" is a peptide linker or a peptide bond.

The S100A9 protein can be present as a monomer or dimer. For example, the S100A9 protein can be in association with S100A8 protein as heterodimer. In these cases, the CD33/S100A9 antagonist binds and sequesters the S100A8/A9 heterodimer complex.

In some cases, the CD33/S100A9 antagonist is multivalent, e.g., it contains at least 2, 3, or more S100A9-binding domains. For example, the CD33/S100A9 antagonist can be a chimeric fusion protein comprising a combination of one or more CD33 ectodomains, one or more TLR4 ectodomains, and/or one or more RAGE ectodomains. The fusion protein can further comprise immunoglobulin heavy chain constant region (Fc), e.g., from IgG4, IgG2 or IgG1.

Multiple copies of the fusion protein can also be combined to form a multivalent complex. Therefore, in some embodiments, two, three, four, five, or more fusion proteins can be linked to a core molecule or particle. For example, the Fc portion can be biotinylated. The biotinylated fusion protein can then be conjugated to a multimeric (e.g., tetrameric) streptavidin. In other embodiments, two or more fusion proteins are conjugated to the surface of a liposome or other microparticle. The multivalent complex can be homogeneous, i.e., containing multiple copies of one type of one fusion protein, or it can be heterogeneous. For example, the multivalent complex can contain combinations of CD33, TLR4, and RAGE fusion proteins. In addition, the multivalent complex can contain multivalent fusion proteins, i.e., at least two fusion protein containing two or more S100A9-binding domains.

In other embodiments, the CD33/S100A9 inhibitor binds and inhibits endogenous CD33 receptor on MDSCs. Therefore, in some embodiments, the CD33/S100A9 antagonist is a molecule containing a CD33 binding domain. For example, the CD33/S100A9 inhibitor can be a recombinant protein that binds CD33 without activating MDSCs and competes for binding of endogenous S100A9. For example, the CD33/S100A9 inhibitor can be a mutant or truncated variant of S100A9, i.e., dominant negative S100A9.

In some embodiments, the CD33/S100A9 inhibitor is an antibody or aptamer that specifically binds CD33 or S100A9 thereby inhibiting endogenous CD33/S100A9 activation.

Also disclosed are methods for treating a disease or condition in a subject that is caused or exacerbated by S100A9 activity, comprising administering to the subject a composition comprising a CD33/S100A9 antagonist disclosed herein.

Also disclosed are methods for identifying an agent for treating MDS. In some embodiments, the methods involve screening candidate agents for the ability to prevent S100A9 binding to CD33. In other embodiments, the methods involve screening candidate agents for the ability to prevent activation of CD33 by S100A9.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows percent of MDSCs in the BM-MNCs of MDS (n=12), age-matched healthy (n=8) and non-MDS cancer specimens (n=8, 4 breast 4 lymphoma, $P<0.0001$).
FIG. 1N shows colony forming ability of unsorted, −MDSC or remixed (+MDSC) MDS BM-MNCs (ratio of 1:3, *, $P<0.005$, **, $P<0.001$).

FIG. 2A shows BM-MNCs from MDS patients (n=12), age matched healthy donors (n=8) and non-MDS cancers (n=8) analyzed for CD33's Mean fluorescence intensity (MFI), *=$P<0.0005$. FIG. 2B shows concentration of IL-10, TGF-β, and VEGF from the supernatant of CD33 (or isotype) cross-linked U937 cells. Bars represent mean±SEM of three wells on three separate experiments. FIG. 2C shows BM-MNCs isolated from healthy donors and infected with an adenoviral vector containing either GFP (Ad-GFP) or CD33 (Ad-CD33) for 72 hours before flow cytometric analysis of the mature myeloid markers, CD11c, CD80, and CCR7, with non-infected cells as a control. FIG. 2D shows results of colony formation assay where after sorting out MDSCs from the BM of MDS patients, the remaining MDSC negative cells were cultured with MDSCs that have been mock infected or infected with lentiviral vector (LV) containing non-targeted shRNA or CD33 shRNA (shCD33) for 14 days. The MDSCs were also cultured for 72 hours after infection with LV containing constructs described above before culturing with MDSC negative BM cells. *, P<0.001, **, P<0.0001, versus cells treated with control shRNA. FIG. 2E to 2G shows IL-10 (FIG. 2E) and TGF-β (FIG. 2F) in the supernatants assayed by ELISA. *, P<0.05, versus cells treated with control shRNA. FIG. 2G shows arginase activity in the shCD33 treated cells. *P<0.05, versus cells treated with control shRNA.

FIG. 3A shows Coomasie blue staining of BM lysates precipitated with either control IgG or CD33-fusion. FIG. 3C shows S100A9 capture ELISA of lysates from un-transfected (negative) or S100A9 transfected cells. Secondary antibody was either anti-S100A9 (positive control) or CD33-fusion, FIG. 3D shows serial dilution of both AD293 and SJCRH30 cell lysates, either un-transfected or transfected with vector or S100A9, onto a PVDF membrane and blotted with CD33-fusion. Coomasie blue staining serves as loading control. FIG. 3E shows S100A9 immunoprecipitation of SJCRH30 CD33/S100A9 co-transfected cell lysate blotted against CD33. FIG. 3F shows PBMC and BM-MNCs from healthy and MDS samples immunoprecipitated with CD33-fusion and blotted for S100A9. FIG. 3O shows BM plasma from either healthy donors (n=3) or MDS-patients (n=3) used to assay SHP-1 recruitment. In all experiments, error bars represent the SEM of three separate experiments.

FIGS. 4A to 4N show S100A9 signaling through CD33 in MDS BM is associated with MDSC activation and suppressive function. FIGS. 4A to 4H show healthy BM cells infected with adenovirus containing GFP or CD33 expression vectors assessed by Q-PCR for the expression of IL-10 (FIG. 4A), TGF-β (FIG. 4C), ARG2 (FIG. 4E) or NOS2 (FIG. 4F), or by ELISA for IL-10 (FIG. 4B) and TGF-β (FIG. 4D). Q-PCR (FIG. 4G) and flow cytometry of GFP expression (FIG. 4H) determined transfection efficiency. FIG. 4K shows silencing S100A8 and S100A9 expression in primary MDS-BM cells using specific shRNA (demonstrated by western blot). FIGS. 4L to 4N show that silencing inhibits the expression of IL-10 (FIG. 4L) and TGF-β (FIG. 4M). *, P<0.01, **, P<0.001, versus cells treated with control shRNA. FIG. 4N shows blocking S100A8 and S100A9 expression by specific shRNA promotes colony formation in BM cells isolated from patients with MDS, *, P<0.05, versus cells treated with control shRNA. In all experiments, error bars represent the SEM of triplicate determination with three separate primary specimens.

FIG. 5A shows Gr1$^+$CD11b$^+$ MDSC accumulation in BM-MNCs isolated from S100A9Tg mice at 6, 18 or 24 weeks, S100A9KO or WT mice at both 6 and 24 weeks.

FIG. 6A shows proportion of MDSC in mice lethally irradiated mice (900 Gy) transplanted with enriched HSCs from either WT, S100A9Tg or a 1:1 mixture of the two at 8 weeks (post-engraftment). Figure representative of 5 transplant experiments. FIG. 6B shows GFP expression of MDSCs in FIG. 6A. FIG. 6C shows percent of LSK HSC, defined as Lineage$^-$cKit$^+$Sca-1$^+$, in lethally irradiated mice after transplant with WT, S100A9Tg or 1:1 mix of enriched HSCs. FIGS. 6D to 6F show proportion and concentration of white blood cells (WBC) (FIG. 6D), hemoglobin (HGB) (FIG. 6E) and RBCs (FIG. 6F) measured weekly by CBC post-transplant. Error bars are the SEM of n=5. FIG. 6G shows percentage of CD34 positive cells in MDSC-depleted MDS-BM specimens treated with or without S100A9 for 48 hours. FIG. 6H shows same experiment as in FIG. 6G, assessing surface expression of Annexin V and PI after treatment with S100A9. FIG. 6I shows healthy human CD34 cells (Lonza Wakersfield) were treated as in FIG. 6H and cultured for 48 hours followed by AnnexinV/PI flow cytometric analysis.

FIGS. 7A to 7B show ATRA decreases MDSCs in the BM of S100A9Tg mice (FIG. 7A) and promotes the expression of myeloid maturation markers (FIG. 7B). FIG. 7C shows BFU colony formation of WT and S100A9Tg mice BM cells treated with ATRA. All of the cultures were duplicates. *, P<0.05, between ATRA treated and vehicle treated S100A9Tg mice. FIG. 7D shows the number of RBC, WBC and platelets from CBC analysis of ATRA treated and untreated mice, *, P<0.0.5, between ATRA treated and vehicle treated S100A9Tg mice. FIG. 7E shows relative expression levels of DAP12 from isolated MDSC from either healthy or MDS specimens by qPCR (n=5). FIG. 7F shows AD293 cells transfected with either vector, WT-DAP12, dominant negative DAP12 (DN) or active DAP12 (P23) for 48 hours and analyzed by western blot for the expression of phosphorylated or total Syk and ERK. This is representative of three independent experiments. MDSC were isolated from the BM of MDS patients and infected with adenoviral vector containing either WT or active DAP12 (P23) for 48 or 72 hours. FIGS. 7G and 7H show surface expression of CD14 or CD15 (FIG. 7G) or the maturation markers CD80, CCR7 and CD11c (FIG. 7H) analyzed by flow cytometry. FIG. 7I shows MDSCs purified from BM-MNCs of MDS patients by FACS sorting and cells infected with LV-WT DAP12 or LV-P23. Colony formation assays were performed in methylcellulose for 14 days. Results are shown as mean±SEM of 7 patients. *, P<0.01, **, P<0.001, versus cells infected with LV-WT.

FIG. 11 illustrates exemplary embodiments of a CD33/S100A9 antagonist.

FIGS. 14A to 14C show erythroid burst-forming units (BFU-E) (FIG. 14B), multipotential colony forming units (CFU-GEMM) (FIG. 14A), and granulocyte/macrophage colony forming units (CFU-GM) (FIG. 14C) in MDS patient specimens treated with IgG, Plasma, or 0.1, 0.5, or 1.0 µg of CD33-IgG chimeric trap.

DETAILED DESCRIPTION

Figure 1A:
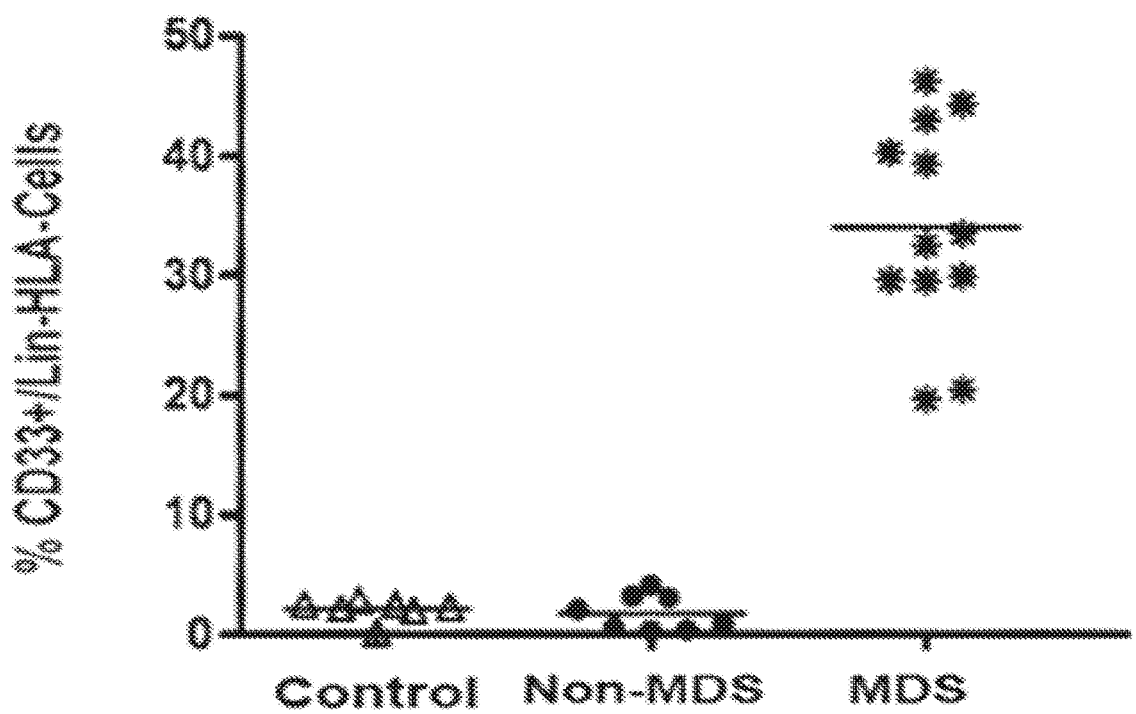
FIGS. 1A to 1N show increased accumulation and function of MDSC in BM cells from
MDS patients.

Immature myeloid-derived suppressor cells (MDSC), known to accumulate in tumor bearing mice and cancer patients, are site-specific inflammatory and T cell immunosuppressive effector cells that contribute to cancer progression (Gabrilovich., D. I., et al. 2009. Nat Rev Immunol 9:162-174; Kusmartsev, S., et al. 2006. Cancer Immunol Immunother 55:237-245). Their suppressive activity is in part driven by inflammation-associated signaling molecules, such as the danger-associated molecular pattern (DAMP) heterodimer S100A8/S100A9 (also known as myeloid-related protein (MRP)-8 and MRP-14, respectively), through ligation of TLR4 (Ehrchen, J. M., et al. 2009. J Leukoc Diol 86:557-566; Vogl, T., et al. 2007. Nat Med 13:1042-1049). Murine CD11b$^+$Gr1$^+$ MDSCs fibrin the basis of the vast majority of the mechanistic studies, however, much less has been reported on their human counterparts. Human MDSCs lack most markers of mature immune cells (LIN⁻, HLA-DR⁻) but possess CD33, the prototypical member of Sialic acid-binding immunoglobulin-like (Ig) super-family of lectins (Siglec) (Gabrilovich, D. I., et al. 2009. Nat Rev Immunol 9:162-174; Talmadge, J. E. 2007. Clin Cancer Res 13:5243-5248; Talmadge, J. E., et al. 2007. Cancer Metastasis Rev 26:373-400; Crocker, P. R., et al. 2007. Nat Rev Immunol 7:255-266). Importantly, while its precise action is unknown, CD33 possesses an immunoreceptor tyrosine-based inhibitory motif (ITIM) that is associated with immune suppression (Crocker, P. R., et al. 2007. Nat Rev Immunol 7:255-266).

It is shown herein that LIN⁺HLA-DR⁻CD33⁺ MDSCs specifically accumulate in the BM of MDS patients (herein referred to as MDS-MDSC) and impair hematopoiesis through a mechanism that involves S100A9 as an endogenous ligand for CD33 initiated signaling. Importantly, using S100A9 transgenic (S100A9Tg) mice, it is shown that sustained activation of this inflammatory pathway leads to the development of MDS, and that this hematologic phenotype is rescued by strategies that suppress CD33 ITIM-signaling. The disclosed finding that S100A9 ligates CD33 to induce MDSC expansion indicates that targeting this pathway can provide a therapeutic approach for the treatment of MDS. Finally, the discovery of this signaling pathway verifies the role of S100A9 as an important initiator of immune-suppression. S100A9Tg mice may therefore serve as a useful model for the study of MDS pathogenesis, treatment and the overall role of MDSC in cancer.

Therefore, disclosed are compositions and methods for treating MDS that involve the use of a CD33/S100A9 inhibitor to inhibit activation of myeloid-derived suppressor cells (MDSCs).

CD33/S100A9 Inhibitor

In some embodiments, the CD33/S100A9 inhibitor binds and sequesters endogenous S100A9 and inhibits its binding to CD33 receptor on MDSCs. Therefore, in some embodiments, the CD33/S100A9 antagonist is a molecule containing a S100A9 binding domain. In other embodiments, the CD33/S100A9 inhibitor binds and inhibits endogenous CD33 receptor on MDSCs. Therefore, in some embodiments, the CD33/S100A9 antagonist is a molecule containing a CD33 binding domain.

Soluble Receptors

For example, the CD33/S100A9 inhibitor can be a soluble CD33 receptor. A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

For example, the CD33/S100A9 antagonist can be a chimeric fusion protein comprising the ectodomain of CD33, Toll like Receptor 4 (TLR4), Receptor for Advanced Glycation End Products (RAGE), or a combination thereof. This ectodomain of CD33, TLR4, and/or RAGE can be any fragment of CD33, TLR4, and/or RAGE capable of binding S100A9.

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide (aka: a 6×his-tag) which can be isolated using nickel or cobalt resins (affinity chromatography).

Amino acid sequences for suitable CD33, TLR4, and RAGE ectodomains are known and adaptable for use in the disclosed compositions and methods. For example, the ectodomain of *Homo sapiens* Myeloid cell surface antigen CD33 (Uniprot P20138 [aa, 18-259] can have the following amino acid sequence:
18-DPN FWLQVQESVT VQEGLCVLVP CTFFHPIPYY DKNSPVHGYW FREGAIISRD SPVATNKLDQ EVQEETQGRF RLLGDPSRNN CSLSINDARR RDNG-SYFFRM ERGSTKYSYK SPQLSVHVTD LTHRPKILIP GTLEPGHSKN LTCSVSWACE QGTPPIFSWL SAAPT-SLGPR TTHSSVILIIT PRPQDHGTNL TCQVKFAGAG VTTERTIQLN VTYVPQNPTT GIFPGDGSGK QETRAGVVH-259 (SEQ ID NO:1), or a fragment or variant thereof, e.g., having an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:1, wherein the fragment or variant is capable of binding S100A9.

There are at least three known single nucleotide polymorphisms ("SNPs") in the ectodomain of CD33 (i.e., W22R, R69G, S128N). Therefore, the extracellular domain of *Homo sapiens* CD33 can have the amino acid sequence of SEQ ID NO:1 with any one or more of these SNPs. For example, the extracellular domain of *Homo sapiens* CD33 can also have the following amino acid sequence:
18-DPN FX$_1$LQVQESVT VQEGLCVLVP CTFFHPIPYY DKNSPVHGYW FREGAHSX$_2$D SPVATNKLDQ EVQEETQGRF RLLGDPSRNN CSLSIVDARR RDNG-SYFFRM ERGSTKYX$_3$YK SPQLSVHVTD LTHRPKILIP GTLEPGHSKN LICSVSWACE QGTPPIFSWL SAAPT-SLGEPR TTHSSVLIIT PRPQDFIGTNL TCQVKEAGAG VITERTIQLN VTYVPQNPTT GIFPGDGSGK QETRAGVVH-259, where X$_1$ is W or R; wherein X$_2$ is R or G; and wherein X$_3$ is S or N (SEQ ID NO:2).

In some cases, the CD33 ectodomain contains only the variable region of CD33 ("vCD33"). For example, in some embodiments, the vCD33 portion has the following amino acid sequence:
19-PN FWLQVQESVI VQEGLCVLVP CIFFHPIPYY DKNSPVHGYW FREGAIISRD SPVATNKLDQ EVQEETQGRF RLLGDPSRNN CSLSIVDARR RDNG-SYFFRM ERGSTKYSYK SPQLSVIIVTD-135 (SEQ ID NO:3), or a fragment or variant thereof, e.g., having an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:3, wherein the fragment or variant is capable of binding S100A9. The vCD33 can also have any one or more of the disclosed SNPs W22R, R69G, S128N). Therefore, in some embodiments, the vCD33 portion has the following amino acid sequence:
19-PN FX$_1$LQVQESVT VQEGLCVLVP CTFFHPIPYY DKNSPVHGYW FREGAIISX$_2$D SPVATNKLDQ EVQEETQGRF RLLGDPSRNN CSLSIVDARR RDNG-SYFFRM ERGSTKYXYK SPQLSVHVTD-135, where X$_1$ is W or R; wherein X$_2$ is R or G; and wherein X$_3$ is S or N (SEQ ID NO:4).

The variable domain of CD33 can be further mutated to create more glycosylation sites in order to enhance binding to S100A9. These mutations can be screened in silico and/or tested in vitro to evaluate S100A9 binding.

N-linked carbohydrates are linked through N-Acetylglucosamine and asparagines. The N-linked consensus sequence is Asn-X$_1$-X$_2$, wherein X$_1$ is any amino acid other than Pro, and X$_2$ is Ser or Thr. Most O-linked carbohydrate covalent attachments involve a linkage between the monosaccharide N-Acetylgalactosamine and the amino acids serine or threonine.

Non-limiting examples of mutant sites will be but not limited at CD33 residues that can be mutated to create more glycosylation sites include Q26N, P40N, L78T, and E84N. Other residues can be identified and tested using routine methods. For example, protein-protein reactions can be assayed using a binding affinity assay, such as an assay that uses surface plasmon resonance (SPR) to detect unlabeled interactants in real time, e.g., using a Biacore™ Sensor Chip (GE Healthcare).

The extraceltular domain of *Homo sapiens* Toll-like receptor 4 (TLR4) (Uniprot O00206 [aa. 24-631]) can have the following amino acid sequence:
24-ESWEPCV EVVPNITYQC MELNFYKIPD NLPFST-KNLD LSFNPLRHLG SYSETSEPEL QVLDLSRCEI QTIEDGAYQS LSHLSTLILT GNPIQSLALG AFSGLSSLQK LVAVETNLAS LENFPIGHLK TLKELN-VAHN LIQSFKLPEY FSNLTNLEHL DLSSNKIQSI YCTDLRVLHQ MPLLNLSLDL SLNPMNFIQP GAFKEI-RLHK LTLRNNFDSL NVMKTCIQGL AGLEVIIRLVL GFERNEGNLE KEDKSALEGL CNUTIEEERL AYLDYYLDDI IDLFNCLTNV SSFSLVNSVTI ERVKDFSYNF GWQHLELVNC KFGQFPILKL KSLKRLTFTS NKGGNAFSEV DLPSLEFLDL SRNGLSFKGC CSQSDFGTTS LKYLDLSFNG VITMSSNFLG LEQLEHLDFQ HSNLKQMSEF SVFLSLRNLI YLDISHTHTR VAFNGIFNGL SSLEVLK-MAG NSFQENFLPD IFTELRNLTF LDLSQCQLEQ LSPTAFNSLS SLQVLNMSHN NFFSLDTFPY KCLNSLQVLD YSLNHIMTSK KQELQHFPSS LAFTNLTQND FACTCEHQSF LQWIKDQRQL LVEV-ERMECA TPSDKQGMPV LSLNITCQMN K-631 (SEQ ID NO:5), or a fragment or variant thereof, e.g., having an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:5, wherein the fragment or variant is capable of binding S100A9.

The ectodoniain of TLR4 has previously been used in a fusion protein with myeloid differentiation factor 2 (MD-2) to function as a lipopolysaccharide (LPS) trap. MD-2 is necessary for TLR4 to bind LPS. However, it is not necessary for TLR4 to bind and trap S100A9. Therefore, in some embodiments, the fusion protein containing TLR4 does not also contain MD-2. In other embodiments, the fusion protein contains both TLR4 and CD33 ectodomains.

The extracellular domain of *Homo sapiens* Receptor for Advanced Glycation End Products (RAGE) (Accession No. NP_001127 [aa. 23-342]) can have the following amino acid sequence: 23-AQNITARI GEPLVLKCKG APKKPPQRLE WKLNTGRTEA WKVLSPQGGG PWDSVARVLP NGS-LETPAVG IQDEGIFRCQ AMNRNGKETK SNYRVRVYQI PGKPEIVDSA SELTAGVPNK VGTCVSEGSY PAGTLSWHLD GKPLVPNEKG VSVKEQTRRH PETGLFTLQS ELMVTPARGG DPRPTFSCSF SPGLPRHRAL RTAPIQPRVW EPVPLEEVQL VVEPEGGAVA PGGTVTLTCE VPAQPSPQIH WMKDGVPLPL PPSPVLILPE IGPQDQGTYS CVATHSSHGP QESRAVSISI IEP-GEEGPTA GSVGGSGLGT LA-342 (SEQ ID NO:6), or a fragment or variant thereof, e.g., having an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:6, wherein the fragment or variant is capable of binding S100A9.

A receptor extracellular domain of CD33, TLR4, and/or RAGE can be expressed as a fusion with immunoglobulin heavy chain constant regions, typically an Fc fragment, which contains two constant region domains and lacks the variable region. Such fusions can be secreted as multimeric molecules wherein the Fc portions are disulfide bonded to each other and two receptor polypeptides are arrayed in close proximity to each other. This chimeric molecule can be produced as fusion protein, which can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced. In particular, the CD33/S100A9 inhibitor can be a chimeric fusion protein comprising the ectodomain of CD33, TLR4, and/or RAGE and an immunoglobulin heavy chain constant region (Fc), e.g., from IgG1.

In some cases, the CD33/S100A9 antagonist is multivalent, e.g., it contains at least 2, 3, or more S100A9-binding domains. In some cases, the antagonist contains at least one CD33 ectodomain and a S100A9-binding domain selected from the group consisting of a TLR4 ectodomain and a RAGE ectodomain.

Multiple copies of the fusion protein can also be combined to form a multivalent complex. Therefore, in some embodiments, two or more fusion proteins can be linked to a core molecule or particle. In its simplest form, a multivalent complex comprises a multimer of two or three or four or more of the disclosed fusion proteins associated (e.g. covalently or otherwise linked) with one another preferably via a linker molecule. Suitable linker molecules include multivalent attachment molecules such as avidin, streptavidin and extravidin, each of which can have four binding sites for biotin.

In some embodiments, the fusion protein can be biotinylated. Once biotinylated, the biotinylated fusion protein can then be conjugated to a tetrameric streptavidin. Proteins can be biotinylated chemically or enzymatically. Chemical biotinylation utilises various conjugation chemistries to yield nonspecific biotinylation of amines, carboxylates, sulfhydryls and carbohydrates. Enzymatic biotinylation results in biotinylation of a specific lysine within a certain sequence by a bacterial biotin ligase. Most chemical biotinylation reagents consist of a reactive group attached via a linker to the valeric acid side chain of biotin. This linker can also mediate the solubility of biotinylation reagents; tinkers that incorporate poly(ethytene) glycol (PEG) can make water-insoluble reagents soluble or increase the solubility of biotinylation reagents that are already soluble to some extent.

Enzymatic biotinylation is most often carried out by genetically linking the protein of interest at its N-terminus, C-terminus or at an internal loop to a 15 amino acid biotin acceptor peptide, also termed AviTag™ or Acceptor Peptide (AP). The tagged protein is then incubated with biotin ligase (BirA) in the presence of biotin and ATP. Enzymatic biotinylation can be carried out in vitro but BirA also reacts specifically with its target peptide inside mammalian and bacterial cells and at the cell surface, while other cellular proteins are not modified. Therefore, the fusion protein can further contain a biotin acceptor peptide that can be biotinylated with BirA in the presence of biotin and ATP. For example, the Fc portion can be enzymatically biotinylated using the AviTag™ system (Avidity, LLC, Aurora, Colo.), which involves incorporating a 15 amino acid peptide sequence into the chimeric fusion protein that can be biotinylated by the BirA enzyme of E. coli. In some embodiments, this biotin acceptor peptide has the amino acid sequence GLNDIFEAQKIEWHE (SEQ ID NO:7).

Oligonucleotides are readily biotinylated in the course of oligonucleotide synthesis by the phosphoramidite method using biotin phosphoramidite. Upon the standard deprotection, the conjugates obtained can be purified using reverse-phase or anion-exchange HPLC.

In other embodiments, two or more fusion proteins are conjugated to the surface of a liposome or other microparticle to form the multivalent complex. A number of reports describe the attachment of antibodies to liposomes. For example, U.S. Pat. No. 5,620,689 discloses so-called "immunoliposomes" in which antibody or antibody fragments effective to bind to a chosen antigen on a B lymphocyte or a T lymphocyte, are attached to the distal ends of the membrane lipids in liposomes having a surface coating of polyethylene glycol chains. In some embodiments, the disclosed multivalent complexes comprising immunoliposomes containing antibodies that specifically bind the disclosed fusion proteins. For example, the antibodies can bind the Fc portion of the fusion protein, or tag on the protein, such as the biotin acceptor peptide.

The multivalent complex can be homogeneous, i.e., containing multiple copies of one type of one fusion protein, or it can be heterogeneous. For example, the multivalent complex can contain combinations of CD33 and TLR4 fusion proteins. In addition, the multivalent complex can contain multivalent fusion proteins, i.e., at least two fusion protein containing two or more S100A9-binding domains.

The disclosed chimeric fusion proteins can also contain a peptide tinker sequences connecting the one or more CD33 and/or TLR4 ectodomains to each other, to the Fc portion, or any combination thereof. For example, the peptide linker can have the amino acid sequence DIEGRMD (SEQ ID NO:8).

In other embodiments, the CD33/S100A9 inhibitor binds and inhibits endogenous CD33 receptor on MDSCs. For example, the CD33/S100A9 inhibitor can be a recombinant protein that binds CD33 without activating MDSCs and competes for binding of endogenous S100A9 (e.g., a mutant or truncated variant of S100A9).

Antibodies

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarily determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Aptamers

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

Nucleic acid aptamers are typically oligonucleotides ranging from 15-50 bases in length that fold into defined secondary and tertiary structures, such as stem-loops or 6-quartets. Nucleic acid aptamers preferably bind the target molecule with a $K_d$ less than $10^{-6}$, $10^{-8}$, $10^{-10}$, or $10^{-12}$. Nucleic acid aptamers can also bind the target molecule with a very high degree of specificity. It is preferred that the nucleic acid aptamers have a $K_d$ with the target molecule at least 10, 100, 1000, 10,000, or 100,000 fold lower than the $K_d$ of other non-targeted molecules.

Nucleic acid aptamers are typically isolated from complex libraries of synthetic oligonucleotides by an iterative process of adsorption, recovery and reamplification. For example, nucleic acid aptamers may be prepared using the SELEX (Systematic Evolution of Ligands by Exponential Enrichment) method. The SELEX method involves selecting an RNA molecule bound to a target molecule from an RNA pool composed of RNA molecules each having random sequence regions and primer-binding regions at both ends thereof, amplifying the recovered RNA molecule via RT-PCR, performing transcription using the obtained cDNA molecule as a template, and using the resultant as an RNA pool for the subsequent procedure. Such procedure is repeated several dines to several tens of times to select RNA with a stronger ability to bind to a target molecule. The base sequence lengths of the random sequence region and the primer binding region are not particularly limited. In general, the random sequence region contains about 20 to 80 bases and the primer binding region contains about 15 to 40 bases. Specificity to a target molecule may be enhanced by prospectively mixing molecules similar to the target molecule with RNA pools and using a pool containing RNA molecules that did not bind to the molecule of interest. An RNA molecule that was obtained as a final product by such technique is used as an RNA aptamer. An aptamer database containing comprehensive sequence information on aptamers and unnatural ribozymes that have been generated by in vitro selection methods is available at aptamer.icmb.utexas.edu.

A nucleic acid aptamer generally has higher specificity and affinity to a target molecule than an antibody. Accordingly, a nucleic acid aptamer can specifically, directly, and firmly bind to a target molecule. Since the number of target amino acid residues necessary for binding may be smatter than that of an antibody, for example, a nucleic acid aptamer is superior to an antibody, when selective suppression of functions of a given protein among highly homologous proteins is intended.

Non-modified nucleic acid aptamers are cleared rapidly from the bloodstream, with a half-life of minutes to hours, mainly due to nuclease degradation and clearance from the body by the kidneys, a result of the aptamer's inherently low molecular weight. This rapid clearance can be an advantage in applications such as in vivo diagnostic imaging. However, several modifications, such as 2'-fluorine-substituted pyrimidines, polyethylene glycol (PEG) linkage, etc. are available to increase the serum half-life of aptamers to the day or even week time scale.

Another approach to increase the nuclease resistance of aptamers is to use a Spiegelmer. Spiegelmers are ribonucleic acid (RNA)-like molecules built from the unnatural L-ribonucleotides. Spiegelmers are therefore the stereochemical mirror images (enantiomers) of natural oligonucleotides. Like other aptamers, Spiegelmers are able to bind target molecules such as proteins. The affinity of Spiegelmers to their target molecules often lies in the pico-to nanomolar range and is thus comparable to antibodies. In contrast to other aptamers, Spiegelmers have high stability in blood serum since they are less susceptible to be cleaved hydrolytically by enzymes. Nonetheless, they are excreted by the kidneys in a short time due to their low molar mass. Unlike other aptamers, Spiegelmers may not be directly produced by the SELEX method. This is because L-nucleic acids are not amenable to enzymatic methods, such as polymerase chain reaction. Instead, the sequence of a natural aptamer identified by the SELEX method is determined and then used in the artificial synthesis of the mirror image of the natural aptamer.

Peptide aptamers are proteins that are designed to interfere with other protein interactions inside cells. They consist of a variable peptide loop attached at both ends to a scaffold. This double structural constraint greatly increases the binding affinity of the peptide aptamer to levels comparable to an antibody.

The variable loop length is typically composed of about ten to twenty amino acids, and the scaffold may be any protein which has good solubility. Currently, the bacterial protein Thioredoxin-A is the most used scaffold protein, the variable loop being inserted within the reducing active site, the two Cysteines lateral chains being able to form a disulfide bridge.

Peptide aptamer selection can be made using different systems, but the most used is currently the yeast two-hybrid system. Peptide aptamer can also be selected from combinatorial peptide libraries constructed by phage display and other surface display technologies such as mRNA display, ribosome display, bacterial display and yeast display. These experimental procedures are also known as biopannings.

Among peptides obtained from biopannings, mimotopes can be considered as a kind of peptide aptamers. All the peptides panned from combinatorial peptide libraries have been stored in a special database with the name MimoDB.

Pharmaceutical Composition

The disclosed compositions can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antirnicmbial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Also disclosed are methods for treating a disease in a subject that is caused or exacerbated by S100A9 activity, comprising administering to the subject a composition comprising a CD33/S100A9 antagonist disclosed herein.

The innate immune system is crucial for initiation and amplification of inflammatory responses. During this process, phagocytes are activated by PAMPs that are recognized by PRRs. Phagocytes are also activated by endogenous danger signals called alarmins or DAMPs via partly specific, partly common PRRs. Two members of the S100 protein family, S100A8 and S100A9, have been identified recently as important endogenous DAMPs. The complex of S100A8 and S100A9 (also called calprotectin) is actively secreted during the stress response of phagocytes. These molecules have been identified as endogenous activators of TLR4 and have been shown to promote lethal, endotoxin-induced shock. Importantly, S100A8/S100A9 is not only involved in promoting the inflammatory response in infections but was also identified as a potent amplifier of inflammation in autoimmunity as well as in cancer development and tumor spread. This proinflammatory action of S100A8/S100A9 involves autocrine and paracrine mechanisms in phagocytes, endothelium, and other cells. As a net result, extravasation of leukocytes into inflamed tissues and their subsequent activation are increased. Thus, S100A8/S100A9 plays a pivotal role during amplification of inflammation.

Diseases that are associated with S100A8/S100A9 activity include, hut are not limited to, rheumatoid arthritis, juvenile idiopathic arthritis, psoriatic arthritis, sepsis, atherosclerosis, acute coronary syndrome/myocardial infarction, diabetes, psoriasis/inflammatory skin disease, inflammatory bowel disease, vasculitis, transplant rejection, SLE/glomerulonephritis, pancreatitis, cancer, dermatomyositis/polymyositis, and hyperzincemia/systemic inflammation. In addition, disease characterized by recurrent infections, hepato-splenomegaly, anemia, vasculopathie, concomitant cutaneous ulcers, and systemic inflammation are defined by extraordinarily high levels of S100A8/S100A9 in extracellular In some embodiments, the method involves treating infection and/or preventing sepsis in a patient in need thereof. Sepsis is caused by the immune system's response to a serious infection, most commonly bacteria, but also fungi, viruses, and parasites in the blood, urinary tract, lungs, skin, or other tissues. There are number of microbial factors which can cause the typical septic inflammatory cascade. An invading pathogen is recognised by its pathogen-associated molecular pattern (PAMP). Examples of PAMPs are lipopolysaccharides (LPS) in Gram-negative bacteria, flagellin in Gram-negative bacteria, muramyl dipeptide in the peptidoglycan cell wall of a Gram-positive bacteria and CpG bacterial DNA. These PAMPs are recognized by the innate immune system's pattern recognition receptors (PRR). There are four families of PRRs: the toll-like receptors, the C-type lectin receptors, the nucleotide oligemerization domain-like receptors and the Rigl-helicases. S100A8/S100A9 acts as an endogenous TLR4 ligand involved in amplification of LPS effects on phagocytes upstream of TNF-α. Although TNF-α is critical for LPS toxicity, blockade of TNF-α had a harmful rather than protective effect in human sepsis. Moreover, in a small study, S100A8/S100A9 levels were demonstrated to decrease in surviving patients during recovery from sepsis, and nonsurvivors were characterized by high S100A8/S100A9 serum levels. Sepsis is usually treated with intravenous fluids and antibiotics. The disclosed CD33/S100A9 antagonist can be used instead of, or in addition to, intravenous antibiotics.

In some embodiments, the method involves treating an inflammatory and/or autoimmune disease in a patient in need thereof. S100A8/S100A9 contributes to the pathogenesis of different types of arthritis. Macrophage-derived S100A8/S100A9 amplifies the inflammatory response in antigen-induced arthritis and also acts as endogenous DAMP in the absence of infection or pathogenic agents. Autoimmunity is the failure of an organism in recognizing its own constituent parts as self, thus leading to an immune response against its own cells and tissues. Any disease that results from such an aberrant immune response is termed an autoimmune or autoinflammatory disease. Autoimmune and autoinflammatory diseases share common characteristics in that both groups of disorders result from the immune system attacking the body's own tissues, and also result in increased inflammation. Prominent examples include Celiac disease, diabetes mellitus type 1 (IDDM), Sarcoidosis, systemic lupus erythematosus (SLE), Sjögren's syndrome, Churg-Strauss Syndrome, Hashimoto's thyroiditis, Graves' disease, idiopathic thrombocytopenic purpura, Addison's Disease, rheumatoid arthritis (RA), gouty arthritis, Polymyositis (PM), Dermatomyositis (DM), graft-versus-host disease, pernicious anemia, Addison disease, scleroderma, Goodpasture's syndrome, inflammatory bowel diseases such as Crohn's disease, colitis, atypical colitis, chemical colitis; collagenous colitis, distal colitis, diversion colitis: fulminant colitis, indeterminate colitis, infectious colitis, ischemic colitis, lymphocytic colitis, microscopic colitis, gastroenteritis, Hirschsprung's disease, inflammatory digestive diseases, Morbus Crohn, non-chronic or chronic digestive diseases, non-chronic or chronic inflammatory digestive diseases; regional enteritis and ulcerative autoimmune hemolytic anemia, sterility, myasthenia gravis, multiple sclerosis, Basedow's disease, thrombopenia purpura, insulin-dependent diabetes mellitus, allergy; asthma, atopic disease; arteriosclerosis; myocarditis; cardiomyopathy; glomerular nephritis; hypoplastic anemia; rejection after organ transplantation and numerous malignancies of lung, prostate, liver, ovary, colon, cervix, lymphatic and breast tissues, psoriasis, acne vulgaris, asthma, autoimmune diseases, celiac disease, chronic prostatits, glomerulonephritis, inflammatory bowel diseases, pelvic inflammatory disease, reperfusion injury sarcoidosis, vasculitis, interstitial cystitis, type 1 hypersensitivities, systemic sclerosis, dermatomyositis, polymyositis, and inclusion body myositis, and allergies. Treatments for autoimmune disease have traditionally been immunosuppressive, anti-inflammatory (steroids), or palliative. Non-immunological therapies, such as hormone replacement in Hashimoto's thyroiditis or Type 1 diabetes mellitus treat outcomes of the autoaggressive response, thus these are palliative treatments. Dietary manipulation limits the severity of celiac disease. Steroidal or NSAID treatment limits inflammatory symptoms of many diseases. MG is used for CIDP and GBS. Specific immunomodulatory therapies, such as the TNFα antagonists (e.g. etanercept), the B cell depleting agent rituximab, the anti-IL-6 receptor tocitizumab and the costimulation blocker abatacept have been shown to be useful in treating RA. Some of these immunotherapies may be associated with increased risk of adverse effects, such as susceptibility to infection. The disclosed CD33/S100A9 antagonist can be used instead of, or in addition to, these existing treatments.

In some embodiments, the method involves treating a neurodegenerative disease or disorder in a patient in need thereof. As used herein, "neurodegenerative disease" includes neurodegenerative disease associated with protein aggregation, also referred to as "protein aggregation disorders", "protein conformation disorders", or "proteinopathies". Neurodegenerative disease associated with protein aggregation include diseases or disorders characterized by the formation of detrimental intracellular protein aggregates (e.g., inclusions in the cytosol or nucleus) or extracellular protein aggregates (e.g., plaques). "Detrimental protein aggregation" is the undesirable and harmful accumulation, oligomerization, fibrillization or aggregation, of two or more, hetero- or homomeric, proteins or peptides. A detrimental protein aggregate may be deposited in bodies, inclusions or plaques, the characteristics of which are often indicative of disease and contain disease-specific proteins. For example, superoxide dismutase-1 aggregates are associated with ALS, poly-Q aggregates are associated with Huntington's disease, and α-synuclein-containing Lewy bodies are associated with Parkinson's disease.

Neurological diseases are also associated with immune failure related to increasing levels of disease-causing factors that exceed the ability of the immune system to contain, or a situation in which immune function deteriorates or is suppressed concomitantly with disease progression, due to factors indirectly or directly related to the disease-causing entity. MDSCs can cause T-cell deficiency by suppressing effector T cell activity, thus promoting neurodegenerative disease associated with immune failure.

Representative examples of Protein Aggregation Disorders or Proteopathies include Protein Conformational Disorders, Alpha-Synucleinopathies, Polyglutamine Diseases, Serpinopathies, Tauopathies or other related disorders. Other examples of neurological diseases or include, but are not limited to, Amyotrophic Lateral Sclerosis (ALS), Huntington's Disease (HD), Parkinson's Disease (PD), Spinal Muscular Atrophy (SMA), Alzheimer's Disease (AD), diffuse Lewy body dementia (DLBD), multiple system atrophy (MSA), dystrophia myotonica, dentatorubro-pallidoluysian atrophy (DRPLA), Friedreich's ataxia, fragile X syndrome, fragile XE mental retardation, Machado-Joseph Disease (MJD or SCA3), spinobulbar muscular atrophy (also known as Kennedy's Disease), spinocerebellar ataxia type 1 (SCA1) gene, spinocerebellar ataxia type 2 (SCA2), spinocerebellar ataxia type 6 (SCA6), spinocerebellar ataxia type 7 (SCA7), spinocerebellar ataxia type 17 (SCA17), chronic liver diseases, familial encephalopathy with neuroserpin inclusion bodies (FENIB), Pick's disease, corticobasal degeneration (CBD), progressive supranuclear palsy (PSP), amyotrophic lateral sclerosis/parkinsonism dementia complex, Cataract, serpinopathies, haemolytic anemia, cystic fibrosis, Wilson's Disease, neurofibromatosis type 2, demyelinating peripheral neuropathies, retinitis pigmentosa, Marfan syndrome, emphysema, idiopathic pulmonary fibrosis, Argyophilic grain dementia, corticobasal degeneration, diffuse neurofibrillary tangles with calcification, frontotemporal dementia/parkinsonism linked to chromosome 17, Hallervorden-Spatz disease, Nieman-Pick disease type C, subacute sclerosing panencephalitis, cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; schizophrenia or psychosis including schizophrenia (paranoid, disorganized, catatonic or undifferentiated), sehizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, postural tremor and intention tremor), chorea (such as Sydenham's chorea, Huntington's disease, benign hereditary chorea, neuroacanthocytosis, symptomatic chorea, drug-induced chorea and herniballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; obesity, bulimia nervosa and compulsive eating disorders; pain including bone and joint pain (osteoarthritis), repetitive motion pain, dental pain, cancer pain, myofacial pain (muscular injury, fibromyalgia), perioperative pain (general surgery, gynecological), chronic pain, neuropathic pain, post-traumatic pain, trigeminal neuralgia, migraine and migraine headache; obesity or eating disorders associated with excessive food intake and complications associated therewith; attention-deficit/hyperactivity disorder; conduct disorder; mood disorders including depressive disorders, bipolar disorders, mood disorders due to a general medical condition, and substance-induced mood disorders; muscular spasms and disorders associated with muscular spasticity or weakness including tremors; urinary incontinence; amyotrophic lateral sclerosis; neuronal damage including ocular damage, retinopathy or macular degeneration of the eye, hearing loss or tinnitus; emesis, brain edema and sleep disorders including narcolepsy, and apoptosis of motor neuron cells. Illustrative examples of the neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. The neuropathic pain includes the pain caused by either central or peripheral nerve damage. And it includes the pain caused by either mononeuropathy or polyneuropathy.

In some cases, the method involves enhancing tumor immune response in a patient in need thereof. S100A8/S100A9 expression is increased in patients with various tumors. Soluble factors secreted from tumor cells are believed to induce overexpression of S100A8/S100A9, resulting in increased generation of MDSCs. These MDSCs can inhibit anti-tumor responses by CD8+ T cells and thus promote tumor growth. The cancer of the disclosed methods can be any cell in a subject undergoing unregulated growth, invasion, or metastasis. In some aspects, the cancer can be any neoplasm or tumor for which radiotherapy is currently used. In some aspects, the cancer can be any tumor that is resistant to standard of care therapy. Thus, Also provided are methods of sensitizing tumors to standard care therapy, comprising administering to the subject an effective amount of a compound or composition as disclosed herein. For example, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. The disclosed CD33/S100A9 antagonist can be used instead of, or in addition to, existing antineoplastic drugs and/or radiation treatments.

As disclosed herein, LIN⁻HLA-DR⁻CD33 MDSCs specifically accumulate in the BM of myelodysplastic syndromes (MDS) patients and impair hematopoiesis through a mechanism that involves S100A9 as an endogenous ligand for CD33 initiated signaling. Therefore, the disclosed method can involve treating MDS in a patient in need thereof. The myelodysplastic syndromes (MDS) are hematological (blood-related) medical conditions with ineffective production (or dysplasia) of the myeloid class of blood cells, in some cases, the MDS patient has a chromosome 5q deletion (del(5q)). However, in other cases, the patient has non-del5q MDS. Although three agents are approved for the treatment of MDS in the United States (US), lenalidomide (LEN) represents the only targeted therapeutic. Therefore, the disclosed CD33/S100A9 antagonist can be used instead of, or in addition to, lenalidomide.

In some embodiments, the method involves treating anemia of chronic disease (including cancer-related anemia) in a patient, comprising administering to the subject an effective amount of a composition as disclosed herein.

Administration

The disclosed. CD33/S100A9 inhibitors may be administered in a therapeutically effective amount to a subject to treat a disease caused or exacerbated by S100A9 activity. The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vagina rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained. See, e.g., U.S. Pat. No. 3,610,795, which is incorporated by reference herein.

The compositions disclosed herein may be administered prophylactically to patients or subjects who are at risk for MDS. Thus, the method can further comprise identifying a subject at risk for MDS prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Screening Methods

Also provided herein is a method of identifying an agent that can be used to treat MDS in a subject. The method can comprise providing a sample comprising CD33 and S100A9 under conditions that allow CD33 and S100A9 to bind, contacting the sample with a candidate agent, detecting the level of CD33/S100A9 binding, and comparing the binding level to a control, wherein a decrease in CD33/S100A9 binding compared to the control identifies an agent that can be used to treat an inflammatory disease.

The binding of S100A9 to CD33 can be detected using routine methods, such as immunodetection methods, that do not disturb protein binding. The methods can be cell-based or cell-free assays. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, get-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, candidate agents can be identified from large libraries of natural products or synthetic (or semi-synthetic extracts or chemical libraries according to methods known in the art. Those skilled in the field of drug discovery and development will understand that the precise source of test extracts or compounds is not critical to the screening procedure(s) used.

Accordingly, virtually any number of chemical extracts or compounds can be screened using the exemplary methods described herein. Examples of such extracts or compounds include, but are not limited to, plant-, fungal-, prokaryotic or animal-based extracts, fermentation broths, and synthetic compounds, as well as modification of existing compounds. Numerous methods are also available for generating random or directed synthesis e.g., semi-synthesis or total synthesis) of any number of chemical compounds, including, but not limited to, saccharide-, lipid-, peptide-, and nucleic acid-based compounds. Synthetic compound libraries are commercially available, e.g., from purveyors of chemical libraries including but not limited to ChemBridge Corporation (16981 Via Taxon, Suite G, San Diego, Calif., 92127, USA, www.chembridge.com); ChemDiv (6605 Nancy Ridge Drive, San Diego, Calif. 92121, USA); Life Chemicals (1103 Orange Center Road, Orange, Conn. 06477); Maybridge (Trevillett, Tintagel, Cornwall PL34 0HW, UK)

Alternatively, libraries of natural compounds in the form of bacterial, fungal, plant, and animal extracts are commercially available from a number of sources, including O2H, (Cambridge, UK), MerLion Pharmaceuticals Pte Ltd (Singapore Science Park II, Singapore 117528) and Galapagos Nev. (Generaal De Wittelaan L11 A3, B-2800 Mechelen, Belgium).

In addition, natural and synthetically produced libraries are produced, if desired, according to methods known in the art, e.g., by standard extraction and fractionation methods or by standard synthetic methods in combination with solid phase organic synthesis, micro-wave synthesis and other rapid throughput methods known in the art to be amenable to making large numbers of compounds for screening purposes. Furthermore, if desired, any library or compound, including sample fbiinat and dissolution is readily modified and adjusted using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect on MDS should be employed whenever possible.

Candidate agents encompass numerous chemical classes, but are most often organic molecules, e.g., small organic compounds having a molecular weight of more than 100 and less than about 2,500 Daltons. Candidate agents can include functional groups necessary for structural interaction with proteins, particularly hydrogen bonding, and typically include at least an amine, carbonyl, hydroxyl or carboxyl group, for example, at least two of the functional chemical groups. The candidate agents often contain cyclical carbon or heterocyclic structures and/or aromatic or polyaromatic structures substituted with one or more of the above functional groups.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

Definitions

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobutin molecules that selectively bind the target antigen.

A "chimeric molecule" is a single molecule created by joining two or more e) ecules that exist separately in their native state. The single, chimeric molecule has the desired functionality of all of its constituent molecules.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes.

The terms "peptide," "protein," and "polypeptide" are used interchangeably to refer to a natural or synthetic molecule comprising two or more amino acids linked by the carboxyl group of one amino acid to the alpha amino group of another.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Microenvironment Induced Myelodysplasia Mediated by Myeloid-Derived Suppressor Cells Methods MDS patients. The majority of patients with MDS were low risk unless otherwise specified. All patients were confirmed by central review and classified in accordance with either the World Health Organization criteria or International Prognostic Scoring System (IPSS). Patients were recruited from the Malignant Hematology clinic at the H. Lee Moffitt Cancer Center & Research Institute and the Radboud University Nijmegen Medical Centre, Department of Hematology in the Netherlands. Bone marrow mononuclear cells (BM-MNC) were isolated from heparinized BM aspirates by Ficoll-Hypaque gradient centrifugation, as previously described (Wei, S., et al. 2009. Proc Natl Acad Sci USA 106:12974-12979). MDSCs were defined and purified by fluorescence activated cell sorting (FACS) of $CD33^+$ cells lacking expression of lineage ($Lin^-$) markers (CD3, CD14, CD16, CD19, CD20, CD56) and HLA-DR.

Mice. All mouse work was approved by the Institutional Animal Care and Use Committee at the University of South Florida. Wild type (WT) FVB/NJ mice were purchased from Jackson Laboratories, and S100A9 knockout mice (KO) and S100A9 transgenic mice (Tg) were generated and used as previously described (Cheng, P., et al. 2008. J Exp Med 205:2235-2249; Manitz, M. P., et al. 2003. Mol Cell Biol 23:1034-1043). S100A9Tg mice were generated from FVB/NJ homozygous mice and bred for more than 15 generations. For the competitive transplant experiment, 18 week old FVB/NJ wild type female mice were irradiated once in a rotating gamma irradiator for a total dose of 900 Gy. Concurrently, BM cells were isolated from the tibias and femurs of age-matched male WT or S100A9Tg mice from which HSCs were then enriched by magnetic cell sorting (MACS, Millitenyi Biotech) following the manufacturer's protocol. Six hours post-irradiation $1 \times 10^7$ enriched HSCs were given by tail vein injection into recipient mice. Mice were then monitored every other day with weight measurements under a sterile hood. Peripheral blood for CBC was collected from the antero-orbital vein by Vivarium staff at the center weekly. By 8 weeks (after which the WT recipients were engrafted, $WBC > 3 \times 10^3$ cells/ml of blood) mice were euthanized by $CO_2$ aspiration at which point peripheral blood was collected by heart puncture followed by dissection of tibias and femurs (as before) and spleen for assessment.

Fluorescence in situ hybridization (FISH). FISH was done at the Cytogenetics Laboratory of Moffitt Cancer Center, and detailed methods have been previously described (Wei, S., et al. 2009. Proc Natl Acad Sci USA 106:12974-12979). Target DNA from MDSC positive (MDS-MDSC) cells and MDSC negative cells was purified from the same patients who were previously confirmed to have del5q or del7q using a commercially available test (Abbott laboratory).

Immunostaining. BM-MNCs were purified from MDS patients, diluted to a concentration of $3 \times 10^5$ cells/ml, cytospinned onto microscope slides and fixed with methanol/acetone (3:1 ratio at −20° C. for 30 min). Washes were done with triton X-100 buffer for 5 min and 50 mM Tris Buffer (pH 7.4) for 10 min prior to blocking for non-specific binding with serum. She slides were stained with the primary antibodies: rabbit anti-CD33 antibody (1:100 dilution, Santa Cruz), mouse anti-granzyme B (1:100 dilution, Fitzgerald Industries) and mouse anti-human CD71 (1:100 dilution, BD Biosciences) followed by their respective secondary antibodies, AlexFluor-594 goat anti-rabbit IgG (Invitrogen), FITC goat anti-mouse (Sigma) and Alexa-350 goat anti-mouse IgG (Molecular Probes). Rat anti-human glycophorin A was pre-conjugated to Alexa-647 using a kit from Molecular Probes) before addition to the sample (1:50 dilution, AbD Serotec) followed by mounting the slides with aqueous medium (Molecular Probes, USA). Immunofluorescence was detected using a Zeiss automated upright fluorescence microscope and images captured by a Nikon camera with the Capture Program AxioVision. Detailed methods for immuno-staining on S100A9 transfected SJCRH30 cells have been published previously (Chen, X., et al, 2008. Blood 113(14):3226-34). Specifically, SJCRH30 cells, which lack detectable expression levels of both CD33 and S100A9, were transfected with either S100A9 or S100A8 (negative control) for 48-72 hours. After incubation with CD33-fusion for 30 min (2 µg/ml), $1 \times 10^4$ cells were cytospinned onto slides and then stained with a secondary anti-human IgG1-APC before analysis by immunofluorescence microscopy. Similarly, SJCRH30 cells, stable-transfected with CD33, were incubated with rhS100A9 tagged with DDK for various time points and stained by the same methodology before analysis.

Suppression assays. To determine whether MDSCs are capable of mediating T cell suppression, $CD45^+$ $CD33^+$ $CD11b^+$ $Lin^-$ cells were sorted from full bone marrow of MDS patients by FACS. The following antibodies were used: CD45-PECy7, CD33-PECy5, CD11b-FITC, CD3-PE, CD14-PE, CD20-PE (all Beckman Coulter, Fullerton, Calif., USA), CD16-PE, CD19-PE (DAKO, Glosnup, Denmark) and CD56-PE (RD Biosciences, San Diego, Calif., USA). T cells were isolated by Magnetic Activated Cell Sorting (MACS) using CD3 microbeads (Miltenyi Biotec, Aubern, Calif., USA) from autologous peripheral blood. 20,000 T cells were seeded in a 96 wells round bottom plate in triplicate in Iscove's modified Dulbecco medium (IMDM;

Invitrogen, Carlsbad, Calif.) supplemented with 10% human serum PAA (PAA Laboratories, Pasching, Austria). Cultures were stimulated with 30 U/ml IL-2 (Chiron, Emeryville, Calif., USA), and anti-CD3/anti-CD28 coated beads (Invitrogen, Carlsbad, Calif., USA) at a 1:2 ratio of T cells to beads. MDSCs were admixed with T cell cultures at ratios of 1:2 and 1:4 and supplemented with 10 ng/ml GM-CSF to support MDSC viability. After 3 days of co-culture, culture supernatants were harvested to measure IFN-γ concentration by ELISA (Pierce Endogen, Rockford, Ill., USA). Subsequently, 0.5 µCi $^3$H-thymidine (Perkin Elmer, Groningen, the Netherlands) was added to each well and, after overnight incubation, $^3$H-thymidine incorporation was measured using a 1205 Wallac Betaplate counter (Perkin Elmer). To determine whether differences in proliferation and IFN-γ production were statistically significant, one-way Anova with Bonferroni post-hoc test was used. Statistical significance was accepted for p values <0.05.

Colony-forming Assay. Cells isolated from either human BM, or from S100A9Tg, S100A9KO or WT tibias and femurs were subjected to ACK for 5 min at room temperature (Sigma) to lyse the red blood cells. Remaining BM cells were then seeded into complete methylcellulose media (MethoCult complete medium with necessary cytokines and growth factors (StemCell Technologies) and the mixture was placed in duplicate gridded 35-mm culture dishes ($2 \times 10^5$ cells/dish) and incubated at 37° C. in 5% $CO_2$ for 7-14 days. After incubation, colonies of BFU-E and CFU-GM were identified manually and counted using an inverted light microscope. For the colony formation assays performed using ATRA treated mice, we administered ATRA at 250 µg (200 µl) or vehicle (Olive oil) orally for five consecutive days before resting two days.

mRNA expression by Real-time Quantitative. RT-PCR and quantitative RT-PCR (qRT-PCR) reactions were performed by means of iQ SYBR Green Supermix (Bio-Rad). The reaction mixture (25 µl total) contained 12.5 µl iQ SYBR green supermix, 0.25 µl forward primer (s GAPDH) (20 µM), 11 µl RNase-free water, and 1.0 µl cDNA. The following cycles were performed 1×3 min at 95° C., 40 amplification cycles (15 s 95° C., 60 s 56° C.), 1×1 min 95° C., 1×1 negative control without cDNA template was run with every assay. The optimal melting point of dsDNA I and min 55° C., and a melting curve (80×10 s 55° C. with an increase of 0.5° C. per 10 seconds). The efficiency of the reaction was optimized beforehand. Transcript copy number per individual was calculated by normalization to GAPDH expression. The relative level of gene expression for each patient was calculated by normalization to the average expression level observed in five controls. CD33 transfected and un-transfected SJCRH 30 cells were treated with 1 µg of rhS100A9 for 20 min and the expression measured by Q-PCR for the presence of IL10 and TGFβ from total RNA and calculated by the ΔΔCt method where rhS100A9 untreated cells were the experimental control and the housekeeping gene GAPDH was the internal control. Error bars represent the SEM of three separate experiments.

Preparation of the CD33/Siglec 3 chimeric fusion protein. Recombinant soluble fusion of CD33/Siglec 3 ectodomain were constructed as described previously (Cannon, J. P., et al. 2012. Immunogenetics 64:39-47; Cannon, J. P., et al. 2011. Methods Mol Biol 748:51-67; Cannon, J. P., et al. 2008. Immunity 29:228-237). Specifically, cDNA fragments encoding CD33/Siglec 3 ectodomain were amplified by PCR and inserted into a vector that encodes the human Fcγ followed by a c-terminal recognition site for *E. coli* biotin ligase. This vector has been engineered to facilitate the fusion of gene segments encoding extracellular Ig-type domains to the Fc region of human IgG1. The recombinant proteins were expressed in 293T cells post-transfection, using Lipofectamine (Invitrogen), with three successive harvests of 25 ml OPTI-MEM I serum-free medium. The harvests were pooled, centrifuged at 500 g for 10 min to remove debris and stored at 4° C. in 0.02% sodium azide. Concentrations of CD33-fusions in culture supernatants were determined by Bradford assay (Biorad, Carlsbad, Calif.).

Mass spectrometry. Following in-gel tryptic digestion, peptides were extracted and concentrated under vacuum centrifugation. A nanoflow liquid chromatograph (EasynLC, Proxeon, Odense, Denmark) coupled to an electrospray ion trap mass spectrometer (LTQ, Thermo, San Jose, Calif.) was used for tandem mass spectrometry peptide sequencing experiments. The sample was first loaded onto a trap column (BioSphere C18 reversed-phase resin, 5 µm, 120 Å, 100 µm ID, NanoSeparations, Nieuwkoop, Netherlands) and washed for 3 minutes at 8 ml/minute. The trapped peptides were eluted onto the analytical column, (BioSphere C18 reversed-phase resin, 150 mm, 5 µm, 120 Å, 100 µm ID, NanoSeparations, Nieuwkoop, Netherlands). Peptides were eluted in a 60 minute gradient from 5% B to 45% B (solvent A: 2% acetonitrile±0.1% formic acid; solvent B: 90% acetonitrile±0.1% formic acid) with a flow rate of 300 nl/min. Five tandem mass spectra were collected in a data-dependent manner following each survey scan. Sequences were assigned using Mascot (www.matrixscience.com) searches against human IPI entries. Carbamidomethylation of cysteine, methionine oxidation, and deamidation of asparagine and glutamine were selected as variable modifications, and as many as 2 missed tryptic cleavages were allowed. Precursor mass tolerance is set to 2.5 and fragment ion tolerance to 0.8. Results from Mascot were compiled in Scaffold, which was used for manual inspection of peptide assignments and protein identifications.

Identifications of specific binding of S100A9 to CD33/Siglec 3. ELISA assay for CD33-fusion binding cell lysate of S100A9 transfected SJCRH 30 cells. Ninety-six well flat-bottom ELISA plates were coated overnight with 1 ug/ml of monoclonal anti-S100A9, as per the manufacturer's suggestions. After washing with 1×PBS-T, 50 µl of lysates from un-transfected cells (negative) or S100A9 transfected cells was added to the wells. Secondary antibody was either a S100A9 polyclonal antibody (positive control) or CD33-fusion as indicated followed by ELISA HRP reaction analysis at 440 nm.

Preparation of adenoviral vector expressing CD33. CD33 plasmid (GeneCopeia) was subcloned into a pShuttle-IRES-hrGFP-1 vector (containing the CMV promoter and hrGFP). The PmeI-digested shuttle vectors were then co-transformed into electro-competent BJ5183 bacteria with pAdEasy-1 (containing the viral backbone) and selected on Kanamycin LB plates. The plasmid in the bacteria was amplified and purified using a plasmid maxiprep system (Qiagen). The complete adenoviral vector was linearized by PacI digestion and then transfected into AD293 cells using Lipofectamine (Invitrogen). All recombinant adenoviruses were amplified in AD293 cells. Viral stocks were obtained by amplification of the AD293 cells followed by standard two-step CsCl gradient ultracentrifugation, dialysis, and storage in a glycerol stock (10% volume/volume) at −80° C., The titer of each viral stock was routinely tested to be $10^{11}$-$10^{12}$ pfu by plaque forming assay using AD293 cells.

Preparation of shRNA lentiviral vectors. SureSilencing™ shRNA Plasmid for Human S100A8, S100A9 and CD33 and negative control (non-target) were purchased from SABiosciences. 293T cells were transfected using transfection reagent (SABiosciences,) according to manufacturer's instructions. Following 6 hours of incubation, the transfection reagent was removed and replaced with fresh DMEM supplemented with 10% fetal bovine serum. Virus containing medium was collected 24-48 hr later. Plasmids, pcDNA3 wild-type DAP12 and P23-DAP12 were cut with HindIII and XhoI (Promega), and DNA Polymerase I Large (KlenowI) (New England Biolabs Inc.) was used to fill in recessed 3' ends of DNA fragments. pWPI, which contains a GFP expression cassette (Addgene Organization), was digested using PMEI (New England Biolabs Inc.). After cutting DNA and vector, pWPI were purified by Strata Prep PCR purification kit (Qiagen), DNAs were ligated (Takara DNA ligation kit, Fisher) into vector pWPI and STBL2 competent cells were transformed (Invitrogen). 293T cells were transfected with pWPI lentivirus vector, the packaging plasmid, psPAX2, and the envelope plasmid, pMD2.G (Addgene Organization) using the Lipofectemine-2000 (Invitrogen) at a ratio of 4:3:1 according to standard protocols. Following 6 hours of incubation, the transfection reagent was removed and replaced with fresh DMEM supplemented with 10% fetal bovine serum. Virus containing medium was collected 24-18 hr later. Cell infection was performed as described above. Four days after the first infection, transduced cells were isolated by FACS sorting GFP$^+$ cells with >99% purity.

Infection of MDSC from MDS patients. MDSCs isolated from MDS patients were infected three times using virus-containing infection medium at 24 hr intervals in the presence of 8 µg/ml polyberene. For each infection, cells were plated in 12-well dishes at $1 \times 10^6$ cells/well. Four days after the first infection, cells were harvested and used for real time PCR, Western blot analysis, flow cytometry, or colony formation assays.

Flow cytometry. BM-MNCs were stained with appropriate specific conjugated antibodies in PBS with 2% BSA buffer. For MDSC sorting, FITC anti-CD3 and FITC anti-HLA-DR were used as positive controls and isotype IgG were used for negative control and to detect non-specific staining. Cells were gently mixed and incubated for 30 min at 4° C. in the dark. Samples were washed with PBS and centrifuged at 500 g for 5 min. For cells used in phenotypic analysis only, 0.5 ml of 1% paraformaldehyde in PBS was added prior to analysis.

Cells were washed in PBS and then stained with PE-conjugated mAbs specific to CD40, CD80, CD83, CD86, CCR7, CD11c, CD14, HLA-DR, TLR2, or TLR4 and relevant isotype controls (eBioscience) for 30 min in the dark, on ice. The cells were then washed with PBS containing 0.5% BSA. Live cells were gated based on negative staining for 7-AAD. Samples were acquired on a FACSCalibur flow cytometer and the analysis was performed using Flowjo 6.3.4 software.

Arginase activity. Arginase activity was measured in cell lysates as previously described (Youn, J. I., et al. 2008. J Immunol 181:5791-5802). In brief, cells were lysed for 30 min with 100 µl of 0.1% Triton X-100. Subsequently, 100 µl of 25 mM Tris-HCl and 10 µl of 10 mM MnCl$_2$ were added, and the enzyme was activated by heating for 10 min at 56° C. Arginine hydrolysis was conducted by incubating the lysate with 100 µl of 0.5 M L-arginine (pH 9.7) at 37° C. for 120 min. The reaction was stopped with 900 µl of H$_2$SO$_4$ (96%)/H$_3$PO$_4$ (85%)/H$_2$O (1/3/7, v/v/v). Urea concentration was measured at 540 nm after addition of 40 µl of α-isonitrosopropiophenone (dissolved in 100% ethanol), followed by heating at 95° C. for 30 min.

NO production. Equal volumes of culture supernatants (100 µl) were mixed with Greiss reagent solution (1% sulfanilamide in 5% phosphoric acid and 0.1% N-1-naphthylethylenediamine dihydrochloride) in double-distilled water and incubated for 10 min at room temperature. Absorbance of the mixture was measured at 550 nm using a microplate plate reader (Bio-Rad). Nitrite concentrations were determined by comparing the absorbance values for the test samples to a standard curve generated by serial dilution of 0.25 mM sodium nitrite.

Western Blot analysis. Cell lysates were prepared by resuspending cell pellet in 1% NP-40, 10 mM Tris, 140 mM NaCl, 0.1 mM PMSF, 10 mM iodoacetamide, 50 mM NaF, 1 mM EDTA, 0.4 mM sodium orthovanadate, 10 µg/ml leupeptin, 10 µg/ml pepsatin, and 10 µg/ml aprotinin and lysing on ice for 30 mM. Cell lysates were centrifuged at 12,000 g for 15 min to remove nuclei and cell debris. The protein concentration of the soluble extracts was determined by using the Bio-Rad (Bradford) protein assay. 50 µg of protein (per lane) was separated on a 10% SDS-polyacrylamide gel by electrophoresis then transferred to a PVDF membrane. Membranes were probed for indicated antibody: anti-S100A8 or anti-S100A9 (MRP8 or calgranulin A and anti-MRP14 or calgranulin B respectively, Santa Cruz); anti-S100A8/A9 (Santa Cruz); anti-phospho Erk, anti-total Erk, anti-phospho Syk, and anti-total Syk (Cell Signaling). Proteins were detected with the enhanced chemiluminescence detection system (ECL, Amersham). Lysate from S100A9 un-transfected, empty vector and S100A9 transfect SJCRH30 or AD293 cells was serially-diluted (as indicated in the figure) with the first lysate, starting at 50 µg, followed by loading onto a nitrocellulose membrane and blocked overnight at 4° C. in 5% milk. Following incubation with CD33-fusion for 2 hours at room temperature, and staining with an anti-human IgG HRP-conjugated secondary, the membrane was washed and used for radiograph analysis to demonstrated specific S100A9 binding to CD33. The membrane was afterwards used for Coomassie blue staining to show the relative equal loading of proteins on each dot in the nitrocellulose membrane.

Complete peripheral blood cell counts (CBC). CBC was performed by animal core laboratory pathological personnel in the vivarium at the Moffitt Cancer Center. The mouse blood parameters were determined as described in Table 1 with a Heska Hematrue Hematology Analyzer.

Figure 5A:
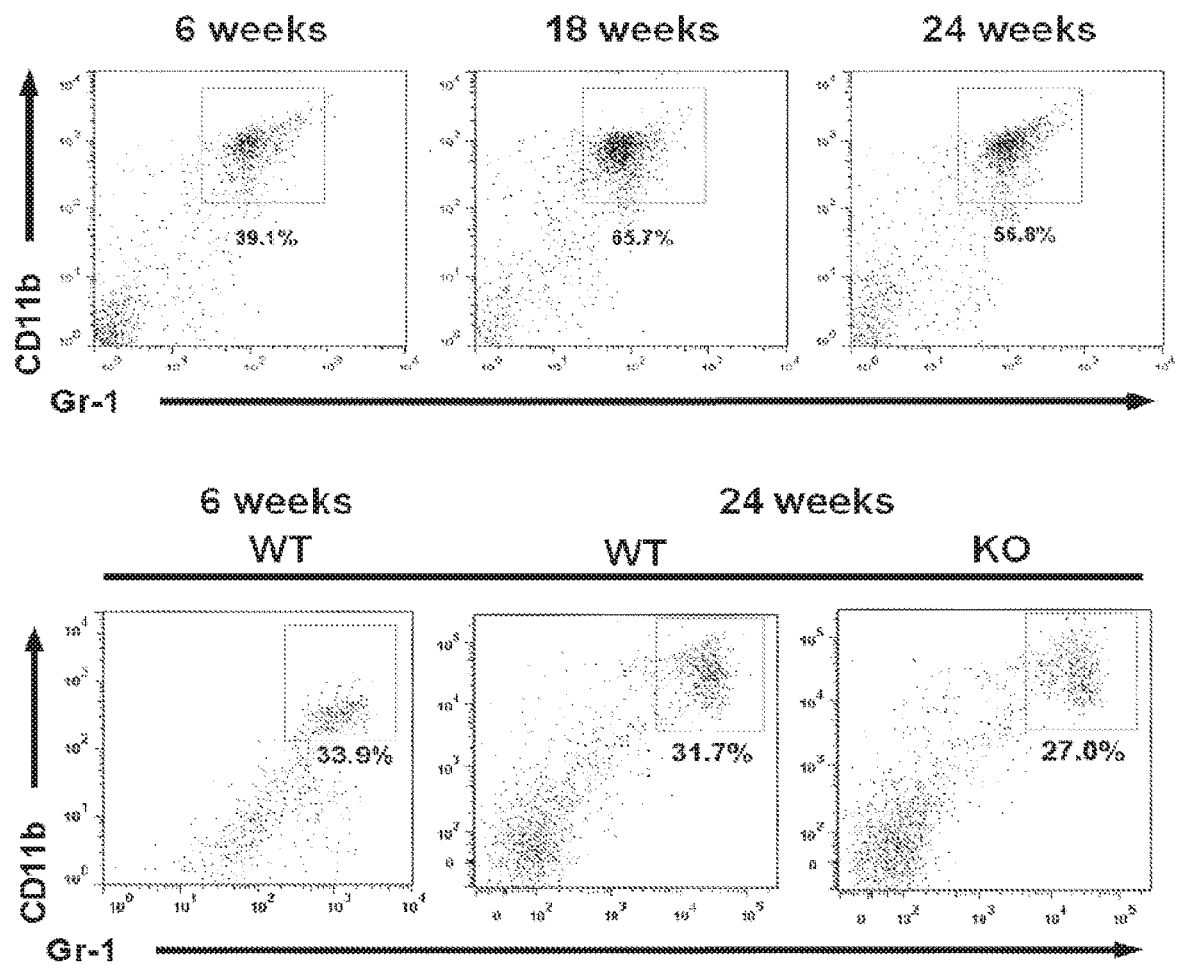
FIGS. 5A to 5P show S100A9Tg mice have increased accumulation and activation of MDSC and display dysplastic features that recapitulate human MDS pathology.
Figure 5B:
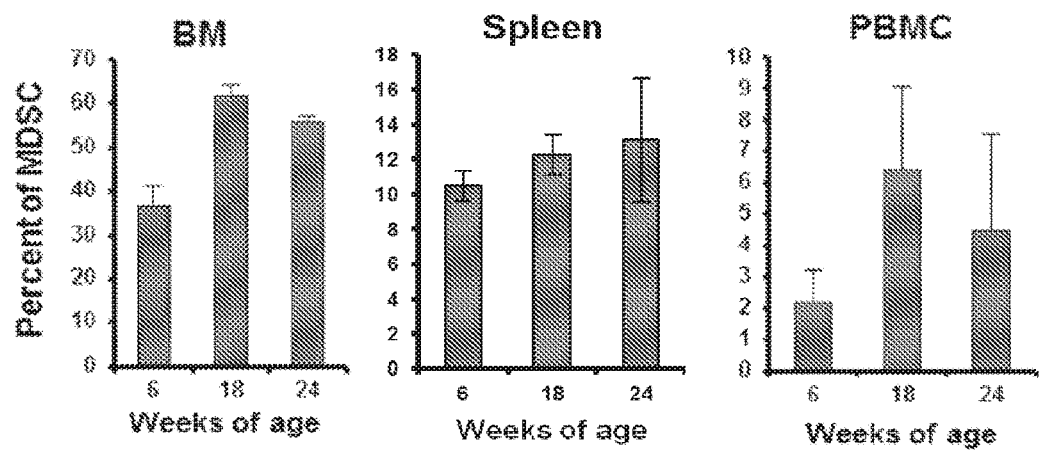
FIG. 5B shows percent of MDSC front BM, spleen and PBMC of S100A9Tg mice at 6, 18 and 24 weeks of age by flow cytometry.
Figures 5C, 5D:
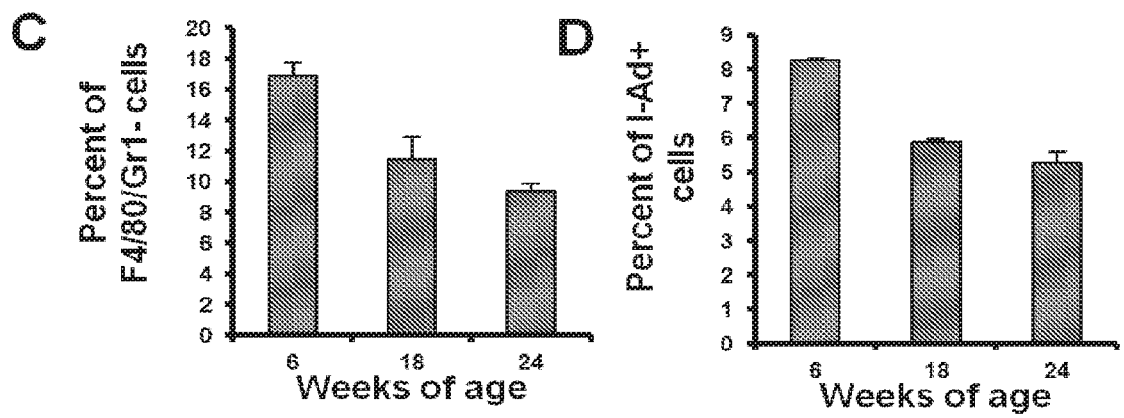
FIGS. 5C to 5D show spleen cells assayed against the maturation markers F4/80$^+$Gr1$^-$ (FIG. 5C) and I-Ad$^+$ (FIG. 5D).
Figures 5E, 5F:
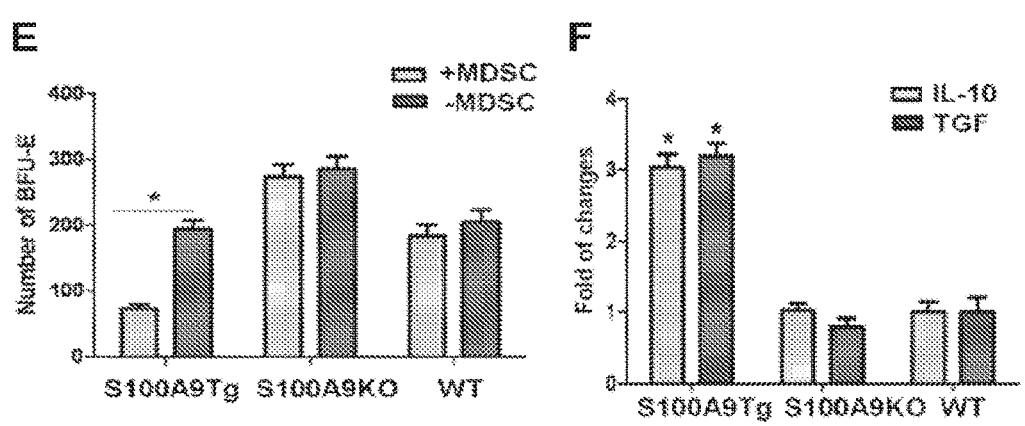
FIG. 5E shows FACS sorted Gr-1$^+$CD11b$^-$ cells (+MDSC) from the BM of mice described in FIG. 5A remixed back with autologous 1×10$^5$ MDSC-negative population (containing HSPC, −MDSC) at 1:1 ratio for 14 days before evaluating colony formation. An MDSC-negative population was used as the control.
FIG. 5F shows MDSCs from WT, S100A9Tg and S100A9 KO mice FACS sorted and incubated in a 96-well plate for 24 hrs after which IL-10 and TGF-β production were measured by ELISA.
Figures 5G, 5H, 5I, 5J, 5K, 5L, 5M, 5N:
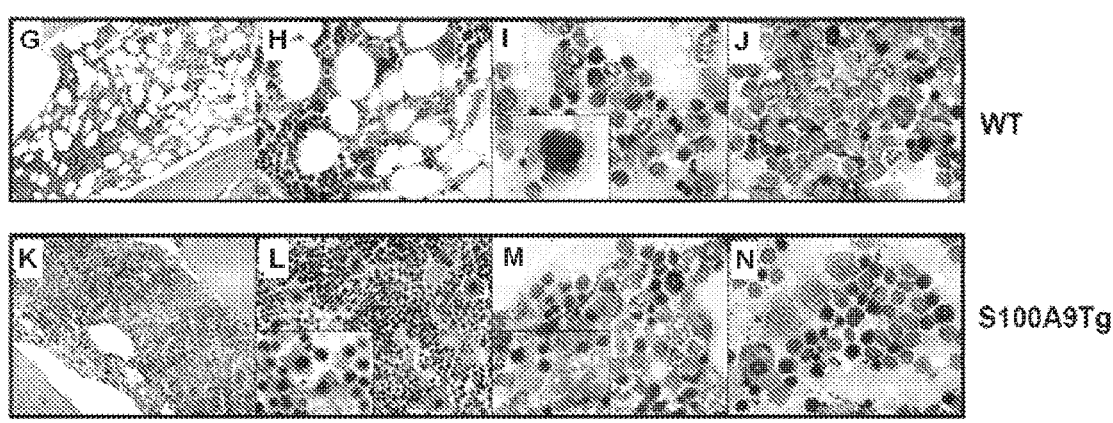
FIGS. 5G to 5N show comparison of the hematopathological analysis of WT (FIGS. 5G-5J) and S100A9Tg mice (FIGS. 5K-5N). MDS-BM primary specimens were tested for the location of S100A9 in CD33 positive cells (FIG. 5O) and CD34 positive cells (FIG. 5P). Flow figures representative of triplicate experiments.

Pathological examination of spleen and BM biopsy from wet and S100A9Tg mice. Bone marrow cells were obtained from bilateral tibiae and femura from 6 month old S100A9Tg and wt control mice as previously described (Xu, S., et al. 2010. J Biomed Biotechnol 2010:105940). Touch prints of murine splenocytes were prepared as described (Ioachim, H. L., et al. 2008. Iochim's lymph node pathology. Chapter 3. cytopathology. Wolters Kluwer/Lippincott Williams & Wilkins, p 21-22). Bone marrow aspirates and touch-imprints were stained using Wright-Giemsa stain. Sections of bone marrow and spleen were fixed in 10% phosphate-buffered neutral formalin, decalcified (only applied to bone marrow) and embedded in paraffin by routine procedures. Sections were cut at 4 µm and stained with hematoxylin and eosin (H&E) and periodic acid Schiff (PAS). The presence of myelodysplastic features characteristic of MDS was evaluated by experienced hematopathologist. BM core biopsy shows 50% cellularity with maturing trilineage hematopoiesis (H&E, 200×). FIG. 5E shows a high power view of the BM biopsy that demonstrates normal appearing megakaryocytes with normal lobation. Mixed myeloid and erythroid precursors are normally distributed with estimated M:E ratio of 2:1 (H&E, 600×). Wright-Giernsa stained BM aspirate exhibits full maturation in all three lineages without dysplastic features (Wright-Giemsa, 1000×). Inlet shows a normal lobated megakaryocyte (FIG. 5F). Touch imprint of mouse spleen displays predominance of small and mature appearing lymphocytes intermingled with occasional erythropoietic precursors (Wright-Giemsa, 1000×) (FIG. 5G). BM core biopsy reveals hypercellularity, approximately 95% with increased megakaryocytes, especially in small forms (H&E, 200×) (FIG. 5H). High power magnification highlights dysplastic megakaryocytes with single or hypolobated, or disjointed nuclei and markedly increased in number (H&E, 600×) (insert) (FIG. 5I). Inlet includes two markedly dysplastic micromegakaryocytes with hypolobation. BM aspirates exhibits mildly increased blasts admixed with myeloid and erythroid precursors. The latter demonstrates slightly irregular nuclear contour and minimal megaloblastoid changes (Wright-Giemsa, 1000×) (FIG. 5J). Inlet contains two blasts showing delicate or fine chromatin, prominent nucleoli, high N:C ratio, and scant basophilic cytoplasm. Touch preparation of transgenic mouse spleen show increased erythroid precursors; some of them displaying enlarged size with abnormal nuclearity and occasional nuclear bridge (Wright-Giemsa, 1000×) (FIG. 5K).

Statistics. All data was presented as means±SEM. Statistical calculations were performed with Microsoft Excel or GraphPad Prism analysis tools. Differences between individual groups were analyzed by paired t-test. P values of <0.05 were considered to be statistically significant.

Results

Lin⁻HLA-DR⁻CD33⁺ MDSC are expanded in MDS primary BM specimens and direct suppression of autologous erythroid precursors. Bone marrow mononuclear cells (BM-MNC) were isolated from MDS BM aspirates (n=12), age-matched healthy BM (n=8), or non-MDS cancer patients (4 breast and 4 lymphoma) and analyzed for the presence of LIN⁻HLA-DR⁻ CD33⁺ MDSCs by flow cytometry. MDS patients exhibited markedly higher numbers of MDSCs (median 35.5%, P<0.0001) compared to healthy donors or non-MDS cancer patients (less than 5%, FIG. 1A). To determine if MDS-MDSCs are derived from the malignant MDS clone, LIN⁻HLA-DR⁻CD33⁺ MDSCs were sorted from MDS specimens with chromosome 5q [del(5q)] or 7q[del(7q)] deletion and analyzed by fluorescence in situ hybridization (FISH) with specific probes.

Figure 1B:
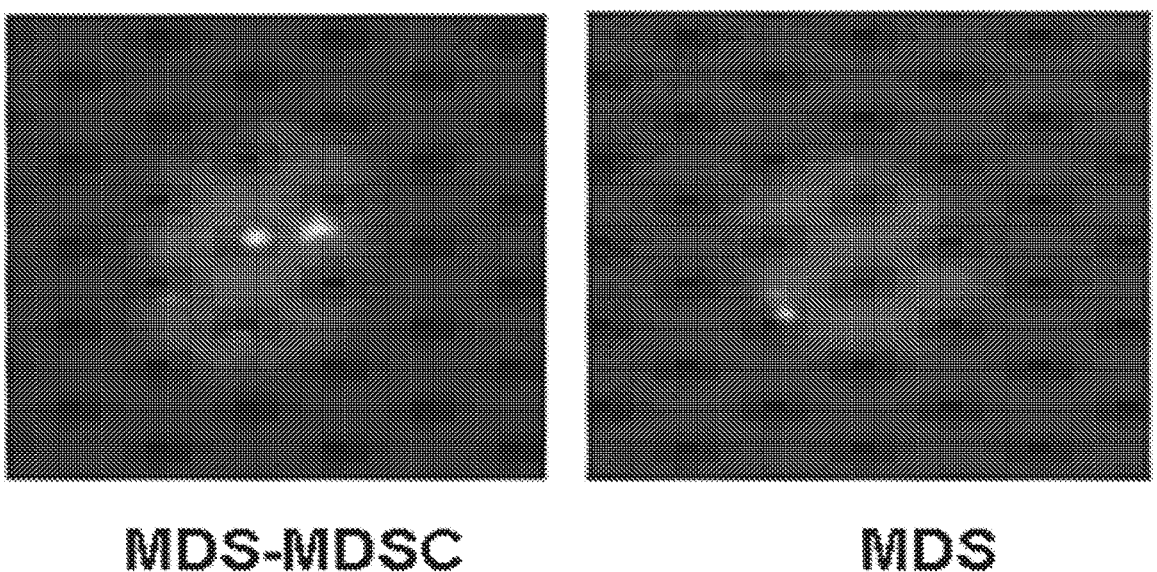
FIG. 1B shows chromosome 7 FISH of sorted MDSC or non-MDSC from MDS BM-MNC (n=5, CEP7 and 7q31).

Cytogenetically abnormal cells harboring del(5q) or del (7q) were restricted to the non-MDSC population, whereas LIN⁻HLA-DR⁻CD33⁺ MDSCs displayed a corresponding normal chromosome complement (FIG. 1B). Exome sequencing studies have shown that clonal somatic gene mutations are demonstrable in the vast majority of MDS specimens lacking chromosome abnormalities by metaphase karyotyping. To further evaluate the relationship between MDSC and the MDS clone, a QPCR array of the most common gene mutations in MDS (Qiagen) was performed in purified MDSC and non-MDSC populations from primary bone marrow MDS specimens. Mutations involving CBL, EZH2, IDH1/2, N-RAS, SRSF2, U2A535 and RUNXI genes were detected in the MDS specimens, however, all mutations were restricted to the MDSC-depleted fraction (Table 1), indicating that LIN⁻HILA-DR⁻C33⁺ MDSC are distinct from the malignant clone.

TABLE 1 qBiomarker ™ Somatic Mutation PCR Array Human Myelodysplastic Syndromes (n = 6)

| Gene | COSMIC ID | nt change | AA change | NON-MDSC | | | | | | MDSC |
| | | | | Pt 1 | Pt 2 | Pt 3 | Pt 4 | Pt 5 | Pt 6 | N = 6 |
|---|---|---|---|---|---|---|---|---|---|---|
| ASXL1 | 36166 | c.1772_1773insA | p.Y591fs*1 | − | − | − | − | − | − | − |
| ASXL1 | 41716 | c.1888_1909del22 | p.H630fs*66 | − | − | − | − | − | − | − |
| ASXL1 | 41717 | c.2302C > T | p.Q768* | − | − | − | − | − | − | − |
| ASXL1 | 52930 | c.2324T > G | p.L775* | − | − | − | − | − | − | − |
| ASXL1 | 41715 | c.3202C > T | p.R1068* | − | − | − | − | − | − | − |
| CBL | 34052 | c.1111T > C | p.Y371H | − | − | − | − | − | − | − |
| CBL | 34055 | c.1139T > C | p.L380P | − | + | + | + | + | + | − |
| CBL | 34057 | c.1150T > C | p.C384R | − | + | + | + | − | + | − |
| CBL | 34077 | c.1259G > A | p.R420Q | − | − | − | − | + | − | − |
| DNMT3A | 53042 | c.2644C > T | p.R882C | − | − | − | − | − | − | − |
| DNMT3A | 87007 | c.2711C > T | p.P904L | − | − | − | − | − | − | − |
| EZH2 | 37031 | c.1936T > A | p.Y646N | − | + | + | + | − | + | − |
| EZH2 | 37029 | c.1937A > C | p.Y646S | − | + | + | + | − | + | − |
| EZH2 | 37028 | c.1937A > T | p.Y646F | − | + | + | + | + | + | − |
| IDH1 | 28748 | c.394C > A | p.R132S | − | − | − | − | − | − | − |
| IDH1 | 28749 | c.394C > G | p.R132G | − | + | + | + | + | + | − |
| IDH1 | 28747 | c.394C > T | p.R132C | − | + | + | − | + | + | − |
| IDH1 | 28746 | c.395G > A | p.R132H | − | + | + | + | − | − | − |
| IDH1 | 28750 | c.395G > T | p.R132L | − | + | + | + | + | + | − |
| IDH2 | 41877 | c.418C > T | p.R140W | − | + | + | + | − | − | − |
| IDH2 | 41590 | c.419G > A | p.R140Q | + | − | − | − | + | + | − |
| IDH2 | 41875 | c.419G > T | p.R140L | − | + | + | + | + | + | − |
| IDH2 | 34039 | c.514A > T | p.R172W | + | + | + | + | + | + | − |
| IDH2 | 33733 | c.515G > A | p.R172K | − | + | + | + | + | + | − |
| IDH2 | 33732 | c.515G > T | p.R172M | − | + | + | + | − | + | − |
| IDH2 | 34090 | c.516G > T | p.R172S | − | − | + | − | − | − | − |
| NRAS | 580 | c.181C > A | p.Q61K | − | + | + | + | + | + | − |
| NRAS | 584 | c.182A > G | p.Q61R | − | + | + | + | − | + | − |
| NRAS | 583 | c.182A > T | p.Q61L | − | − | − | − | − | − | − |
| NRAS | 586 | c.183A > C | p.Q61H | − | + | + | + | + | + | − |
| NRAS | 585 | c.183A > T | p.Q6IH | − | − | − | − | + | − | − |

TABLE 1-continued qBiomarker ™ Somatic Mutation PCR Array Human Myelodysplastic Syndromes (n = 6)

| Gene | COSMIC ID | nt change | AA change | NON-MDSC Pt 1 | Pt 2 | Pt 3 | Pt 4 | Pt 5 | Pt 6 | MDSC N = 6 |
|---|---|---|---|---|---|---|---|---|---|---|
| NRAS | 563 | c.34G > A | p.G12S | − | + | − | − | − | + | − |
| NRAS | 562 | c.34G > T | p.G12C | − | + | + | + | + | − | − |
| NRAS | 564 | c.35G > A | p.G12D | − | − | + | − | + | + | − |
| NRAS | 565 | c.35G > C | p.G12A | − | + | − | + | + | + | − |
| NRAS | 566 | c.35G > T | p.G12V | − | + | + | + | + | + | − |
| NRAS | 569 | c.37G > C | p.G13R | − | + | + | + | + | + | − |
| NRAS | 570 | c.37G > T | p.G13C | − | + | + | + | + | + | − |
| NRAS | 573 | c.38G > A | p.G13D | − | − | − | − | − | − | − |
| NRAS | 574 | c.38G > T | p.G13V | − | + | − | + | + | + | − |
| RUNX1 | 24756 | c.167T > C | p.L56S | − | + | + | − | − | + | − |
| RUNX1 | 24736 | c.319C > T | p.R107C | − | + | + | + | − | + | − |
| RUNX1 | 24769 | c.496C > T | p.R166* | − | − | − | − | − | − | − |
| RUNX1 | 24721 | c.592G > A | p.D198N | − | − | − | − | − | − | − |
| RUNX1 | 24799 | c.593A > G | p.D198G | − | − | − | − | + | − | − |
| RUNX1 | 24805 | c.602G > A | p.R201Q | − | + | − | + | − | − | − |
| RUNX1 | 24731 | c.611G > A | p.R204Q | − | − | − | + | + | − | − |
| SF3B1 | 110693 | c.1866G > T | p.E622D | − | − | − | − | − | − | − |
| SF3B1 | 110695 | c.1874G > T | p.R625L | − | − | − | − | − | − | − |
| SF3B1 | 131560 | c.1984C > G | p.H662D | − | − | − | − | − | − | − |
| SF3B1 | 130416 | c.1986C > A | p.H662Q | − | − | − | − | − | − | − |
| SF3B1 | 110692 | c.1986C > G | p.H662Q | − | − | − | − | − | − | − |
| SF3B1 | 110694 | c.1996A > G | p.K666E | − | − | − | − | − | − | − |
| SRSF2 | 98000028 | c.284C > A | P95H | − | + | + | + | + | + | − |
| SRSF2 | 98000029 | c.284C > T | P95L | − | + | + | + | − | − | − |
| SRSF2 | 98000030 | c.284C > G | P95R | − | + | + | + | + | + | − |
| TET2 | 41644 | c.1648C > T | p.R550* | − | + | + | − | − | − | − |
| TET2 | 43417 | c.2746C > T | p.Q916* | − | − | − | − | − | − | − |
| TP53 | 10648 | c.524G > A | p.R175H | − | − | − | − | − | − | − |
| TP53 | 10662 | c.743G > A | p.R248Q | − | + | + | + | − | − | − |
| TP53 | 10660 | c.818G > A | p.R273H | − | − | − | + | − | − | − |
| TP53 | 10656 | c.742C > T | p.R248W | − | − | − | − | − | − | − |
| TP53 | 10659 | c.817C > T | p.R273C | − | − | − | + | − | − | − |
| TP53 | 10704 | c.844C > T | p.R282W | − | − | − | − | − | − | − |
| TP53 | 10817 | c.747G > T | p.R249S | − | + | + | + | + | + | − |
| TP53 | 6932 | c.733G > A | p.G245S | − | − | − | − | + | − | − |
| TP53 | 10758 | c.659A > G | p.Y220C | − | + | + | − | + | − | − |
| TP53 | 10654 | c.637C > T | p.R213* | − | − | − | − | − | − | − |
| TP53 | 10670 | c.469G > T | p.V157F | − | − | − | + | − | − | − |
| TP53 | 10705 | c.586C > T | p.R196* | − | − | − | + | − | + | − |
| TP53 | 10645 | c.527G > T | p.C176F | − | − | + | + | − | − | − |
| TP53 | 10889 | c.536A > G | p.H179R | − | + | + | + | − | + | − |
| TP53 | 10808 | c.488A > G | p.Y163C | − | + | + | + | − | − | − |
| TP53 | 10722 | c.853G > A | p.E285K | − | + | − | − | − | + | − |
| TP53 | 43606 | c.734G > A | p.G245D | − | + | + | + | + | − | − |
| TP53 | 10779 | c.818G > T | p.R273L | − | + | + | + | + | − | − |
| TP53 | 10725 | c.701A > G | p.Y234C | + | + | + | + | − | + | − |
| U2AF35 | 98000031 | c.470A > C | Q157P | + | + | + | + | − | + | − |
| U2AF35 | 98000032 | c.470A > G | Q157R | − | + | + | + | − | + | − |
| U2AF35 | 98000033 | c.101C > T | S34F | − | − | − | − | − | − | − |
| U2AF35 | 98000034 | c.101C > A | S34Y | + | + | + | + | − | + | − |
| DNMT3A | 99000100 | copy_number | copy_number | − | − | − | − | − | − | − |

Sample was fresh and sorted prior to genomic DNA isolation. According to the manufacturer's analysis description: the raw CT for a given mutation assay in a test sample is compared with a predefined CT cutoff. Based on the difference, the mutation can be considered as "Present" (+), "Borderline" (−/+), or "Absent" (−).

Figure 1C:
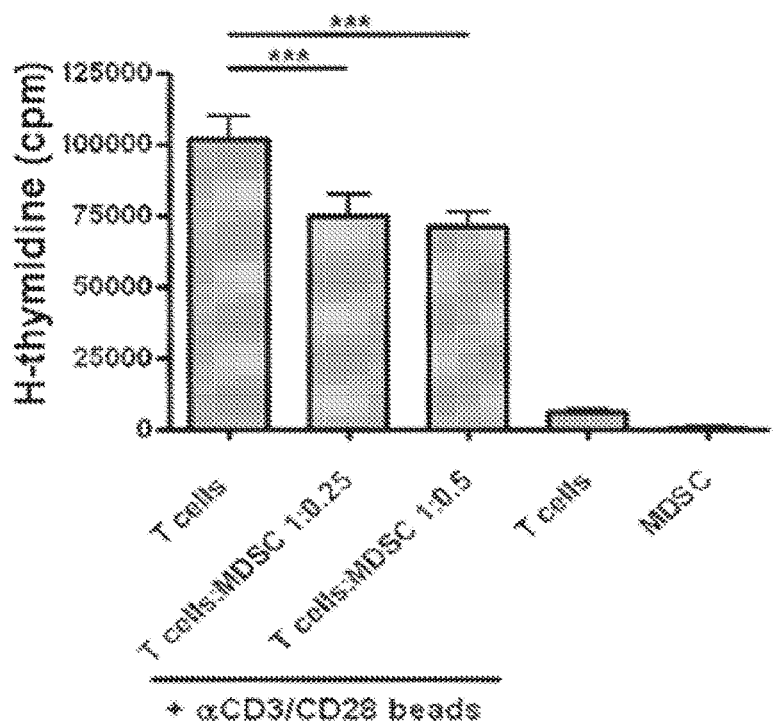
FIGS. 1C and 1D show $^3$H-thymidine incorporation (FIG. 1C) and IFN-γ ELISA (FIG. 1D) of stimulated autologous T cells co-cultured with sorted MDS-MDSCs at 1:0.25 and 1:0.5 ratios (T cells:MDSC). Error bars denote standard deviation of three separate patient samples tested in triplicate.
Figure 1D:
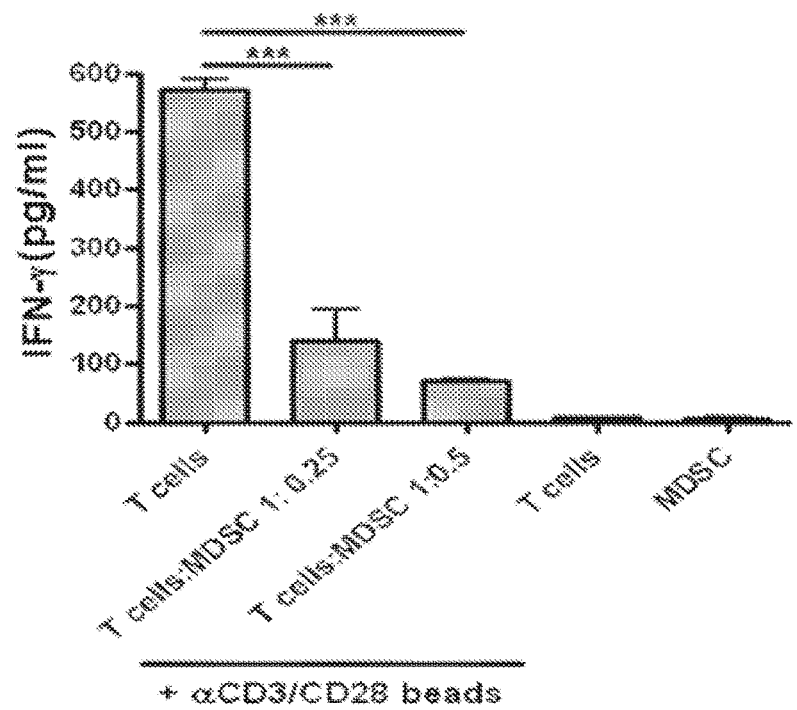
Figure 1E:
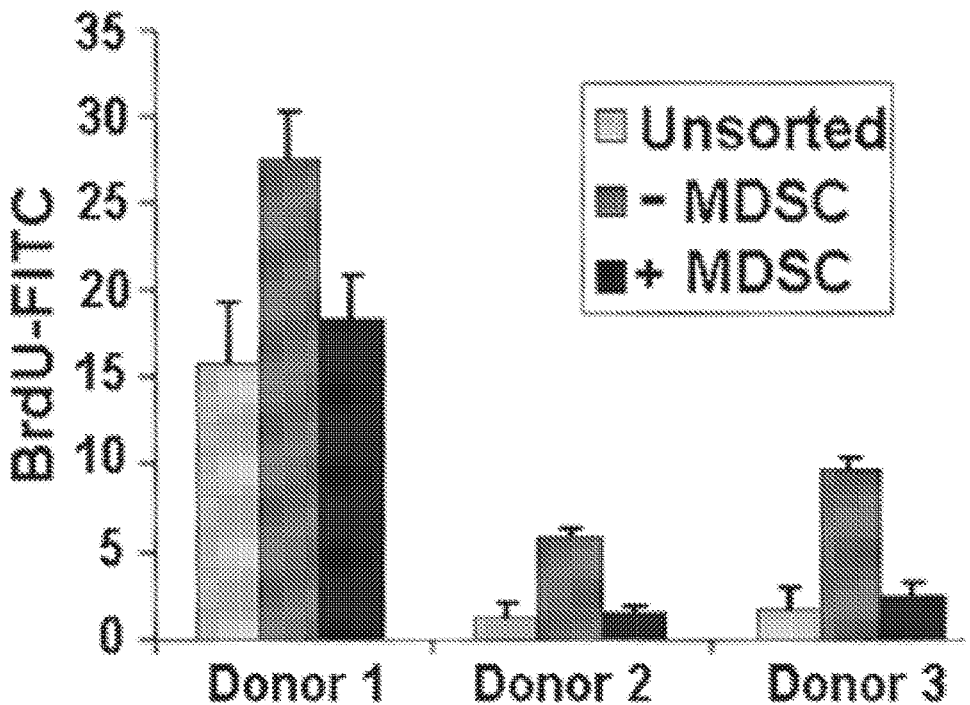
FIG. 1E shows BrDu incorporation of stimulated T cells after admixing with autologous unsorted. MDSCs depleted (−MDSC) or remixed (+MDSC) BM-MNCs.
Figures 1F, 1G, 1H, 1I:
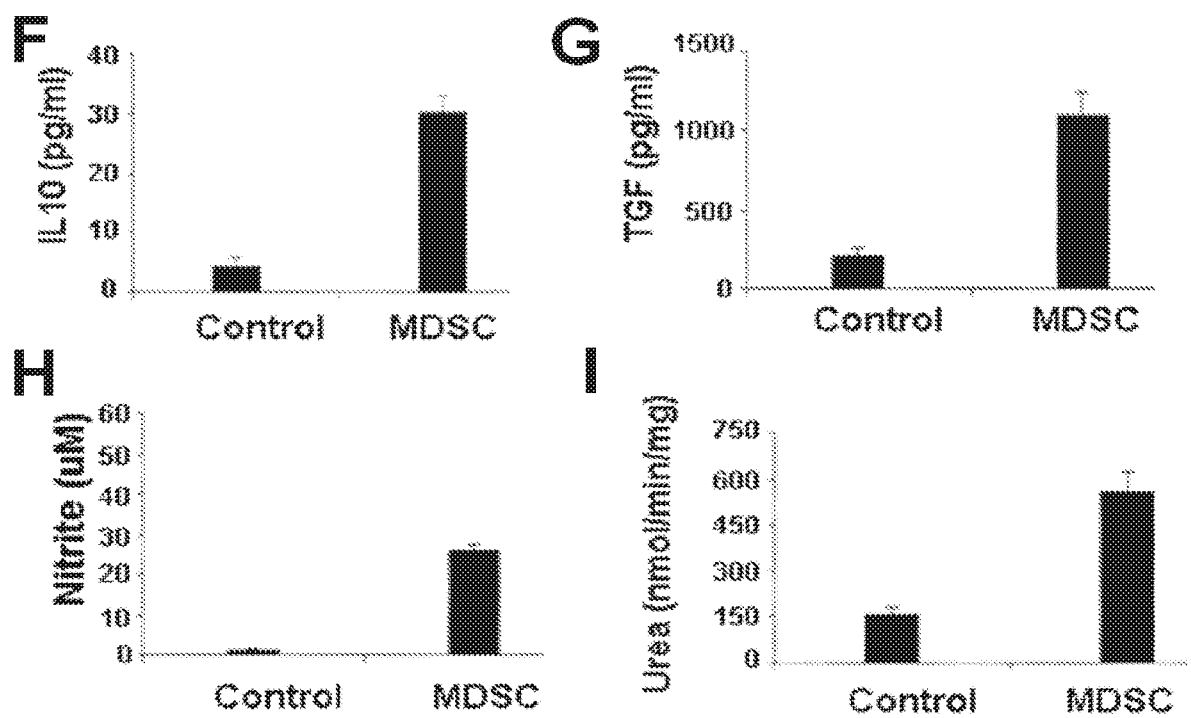
FIGS. 1F to 1I show sorted MDSCs from MDS or healthy donor BM tested for IL-10 (FIG. 1F), TGFβ (FIG. 1G), arginase (FIG. 1H) and NO (FIG. 1I) production by ELISA after 24 hours of culture.

Recognized functional properties of MDSC include suppression of antigen stimulated or CD3 stimulated T cell proliferation and interferon-gamma (IFN-γ) production (Gabrilovich, D. I., et al. 2009. Nat Rev Immunol 9:162-174; Ostrand-Rosenberg, S., et al, 2009. J Immunol 182:4499-4506). T cells purified from the BM of MDS patients showed reduced T cell proliferation (FIG. 1C) and IFN-γ production (FIG. 1D) after co-culture with autologous MDS-MDSC, demonstrating the expected suppressive activity of these cells. To further validate these findings, MDSCs were depleted from MDS BM specimens prior to anti-CD3/anti-CD28 stimulation and then the MDSC were added back to the control group. MDSC-depletion significantly improved T cell responses compared to the MDSC-supplemented group (FIG. 1E), thereby linking the observed impaired T cell responsiveness to the actions of BM-derived MDSCs. In addition, suppressive MDS-MDSC overproduced suppressive cytokines such as IL-10 and TGF-β (FIGS. 1F & G), as well as nitric oxide (NO) and arginase compared to MDSCs isolated from healthy donors (FIGS. 1H & I). Collectively, these data demonstrate that LIN⁻HLA-DR⁻CD33⁺ MDSC are a unique and functional cellular subset supporting a pro-inflammatory microenvironment and immune tolerance in the BM of MDS patients.

Figure 1J:
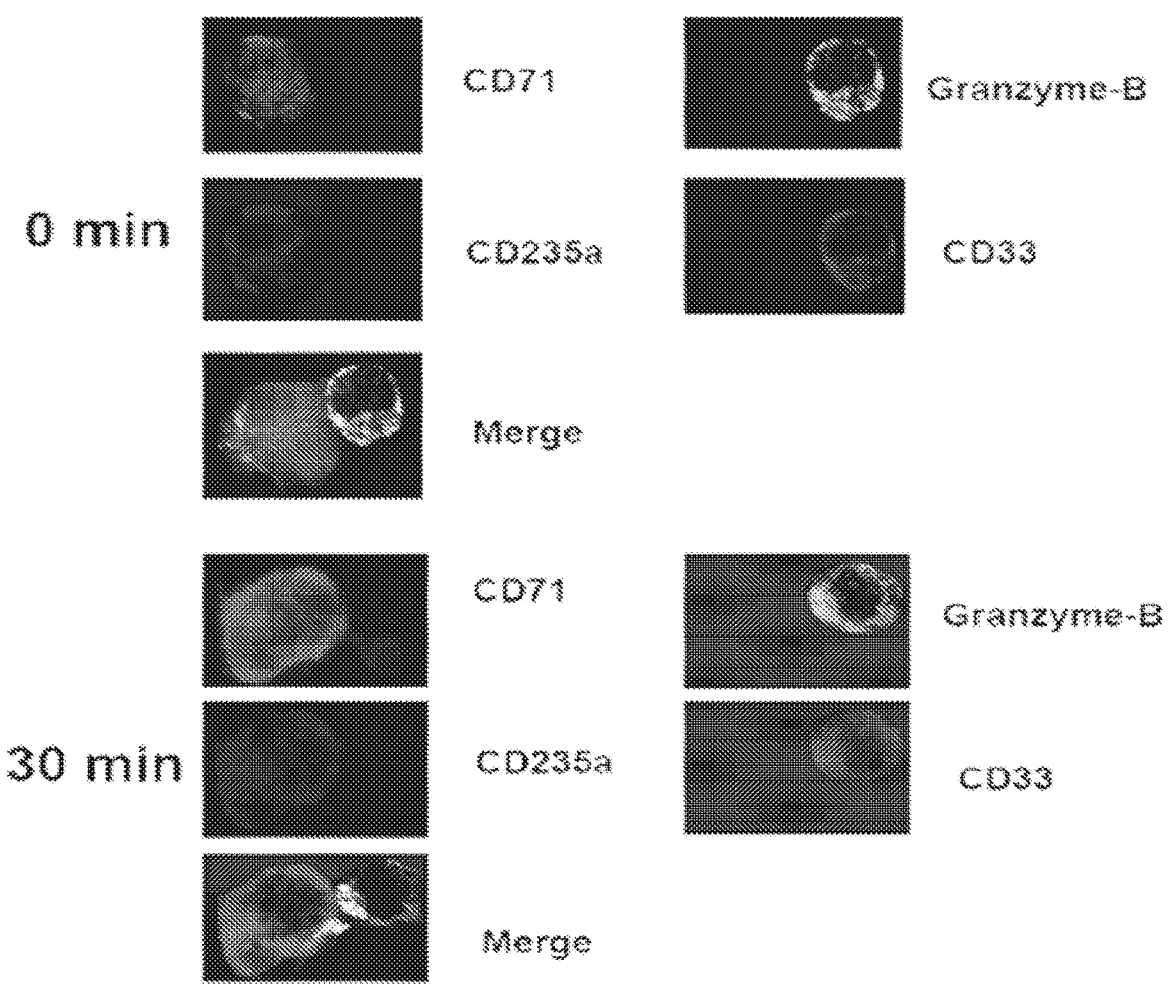
FIG. 1J shows MDSC:erythroid precursor contact zone of admixed sorted MDS-MDSC and autologous erythroid precursors at a ratio of 1:3 (MDSC: erythroid precursor) by microscopy at 0 and 30 minutes. Cells were stained for CD71, glycophorin A, CD33 and granzyme B.
Figure 1K:
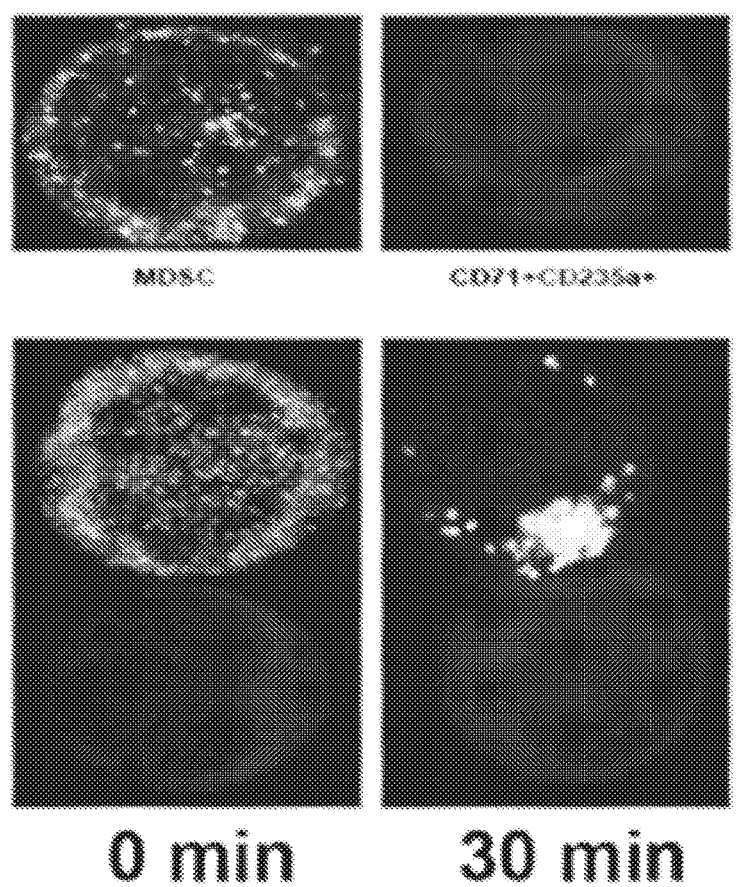
FIG. 1K shows sorted MDSCs from MDS or healthy donors labeled with CD33 and granzyme B co-incubated with purified autologous erythroid precursors (0 or 30 min) and monitored by microscopy. (L) Counts of MDSC-HPC conjugate mobilized granules.
Figure 1L:
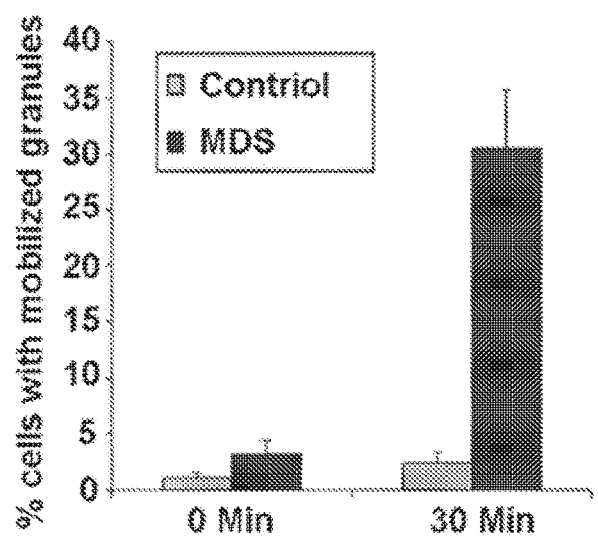
FIG. 1M shows Annexin V exposure on erythroid precursors (CD71$^+$ CD235a$^+$) incubated with or without sorted autologous MDS-BM MDSC.
Figure 1M:
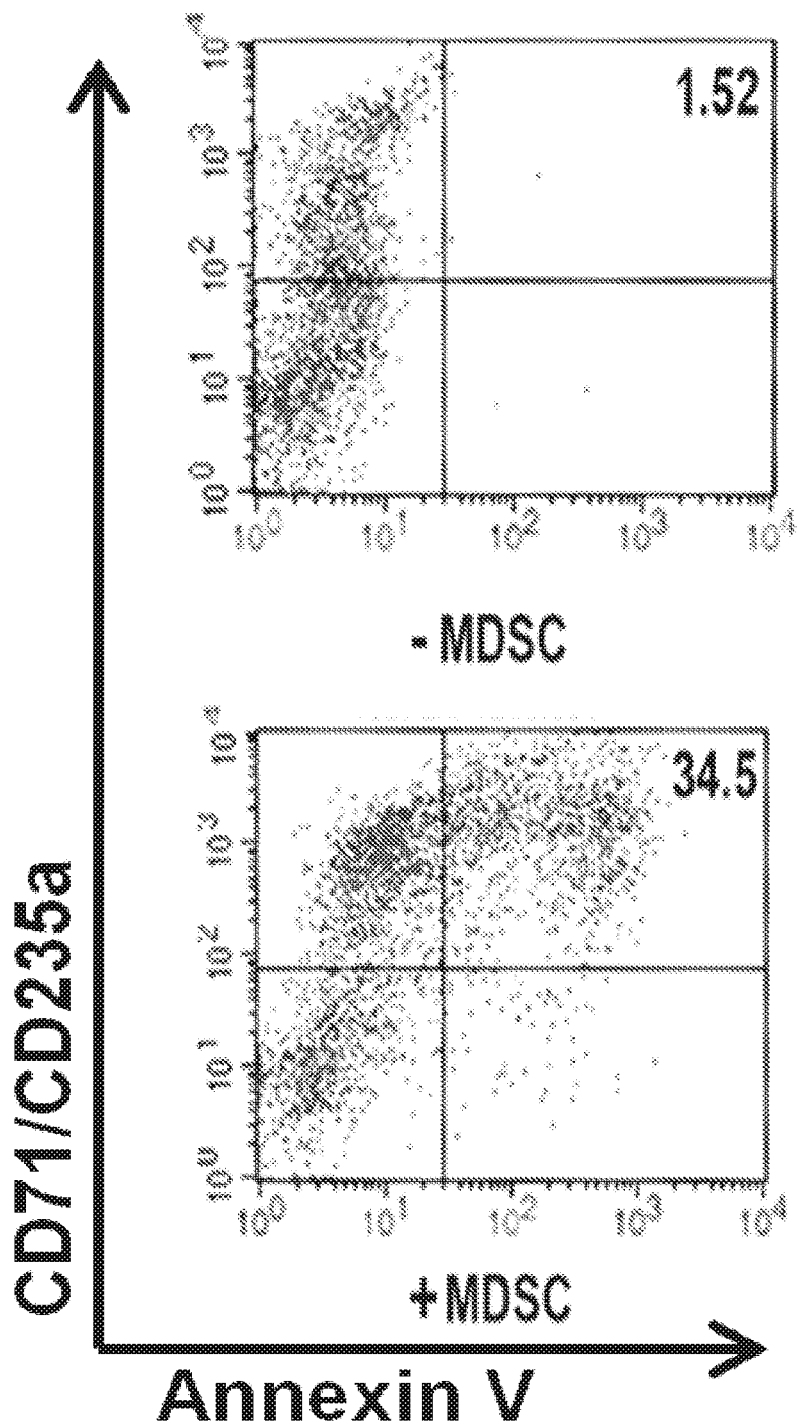
Figure 1N:
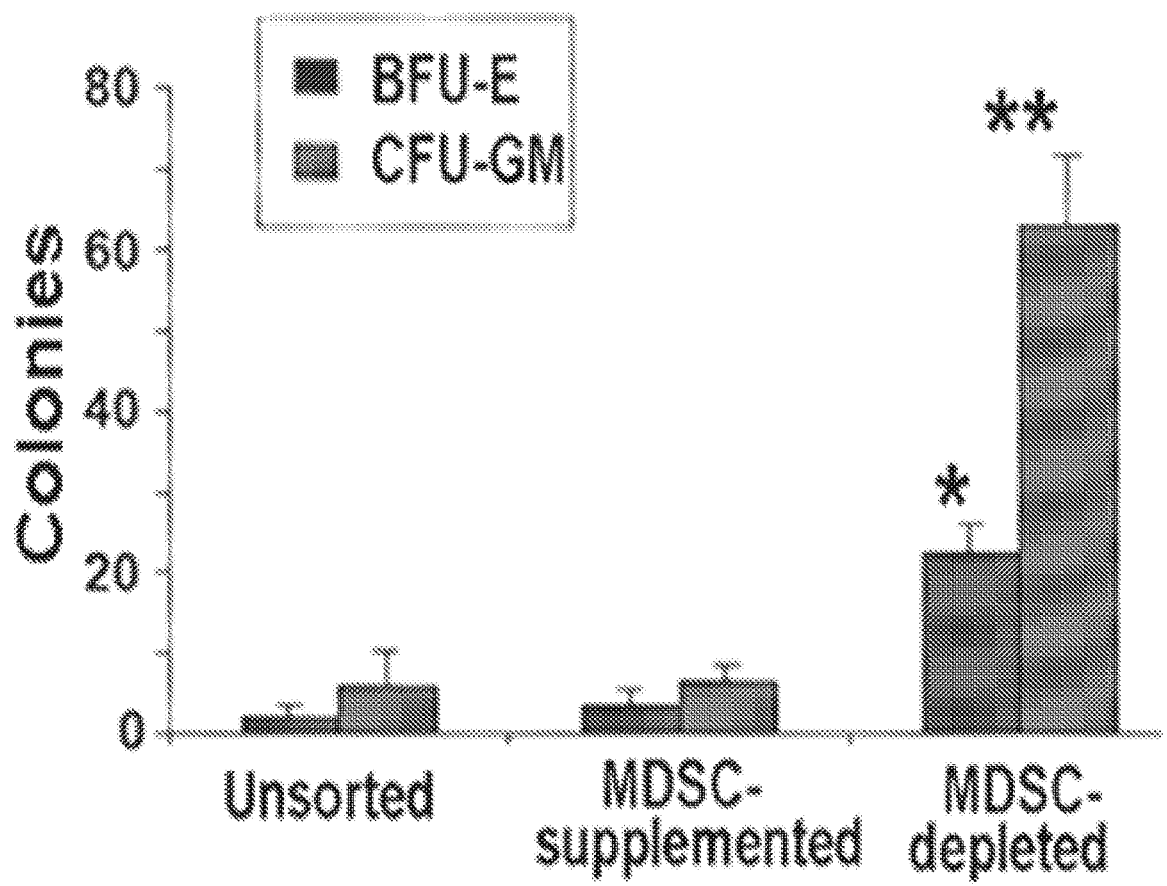

MDSC-mediated suppressive and cytotoxic effector functions require direct contact with target cells. One mechanism utilized by cytotoxic effectors is the mobilization of pore-forming granules and the release of caspase-activating effector proteases, such as granzyme B, to the site of effector: target contact thereby inducing apoptosis of the target cell (Chen, X., et al. 2008. Blood 113(14):3226-34). Since MDSC reside in close proximity with hematopoietic progenitor cells (HPCs) that in MDS display an increased apoptotic rate, MDSC-mediated cytostatic activity may contribute to HPC death. To address this, MDS-MDSC granule mobilization and release of granzyme B were examined using four-color immunofluorescence staining. MDS-MDSCs exhibited strong granzyme B polarization at the site of cell contact with CD235a$^+$ (glycophorin A)/CD71$^+$ autologous erythroid precursors (FIG. 1J). After 30 minutes incubation, the frequency of such effector-target conjugates in MDS patient specimens was significantly higher (34%) than in samples from healthy donors (5% P<0.001, FIGS. 1K & L). These cellular interactions resulted in apoptosis of targeted erythroid precursors (FIG. 1M) demonstrating that in addition to known MDSC-mediated immune suppressive functions, there is an unrecognized MDSC-mediated hematopoietic suppressive capacity. To corroborate this finding, the effects of MDSC on the proliferative capacity of HPCs were examined in MDS-MDSC-depleted, HSPC enriched, BM patient specimens in a methylcellulose colony formation assay. Burst-forming unit-erythroid (BFU-E) and colony forming unit-granulocyte/macrophage (CFU-GM) colony formation was significantly higher in MDSC-depleted specimens compared to both MDSC-supplemented and unsorted samples (FIG. 1N), demonstrating that MDSC have a direct suppressive role on erythroid and myeloid progenitor cell development.

Figure 2A:
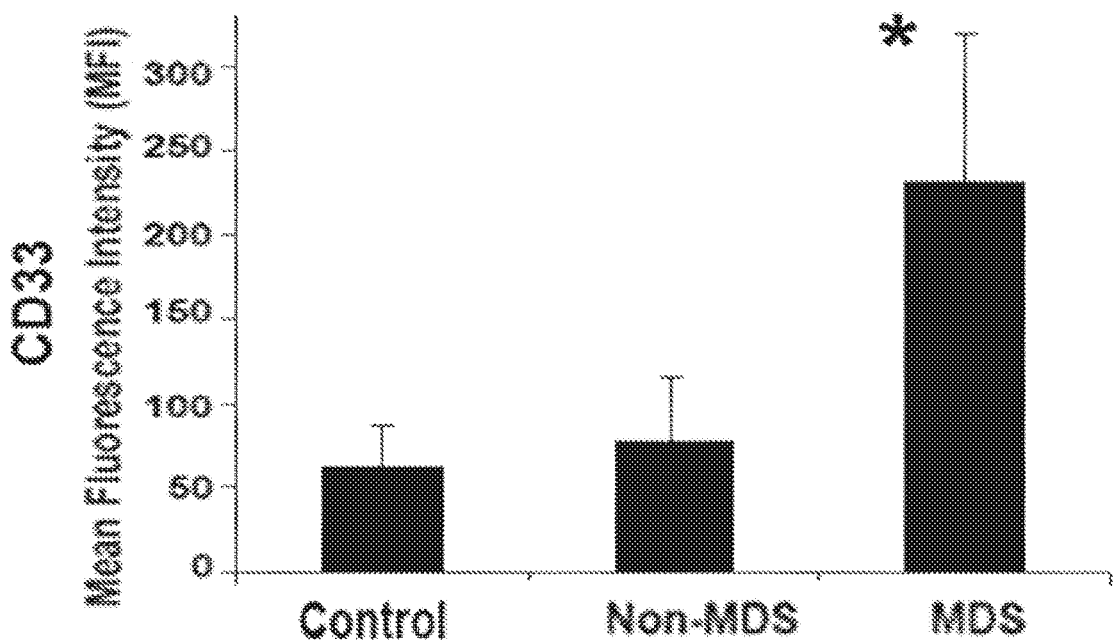
FIGS. 2A to 2G show CD33 signals to enhance MDSC suppressive functions.
Figure 2B:
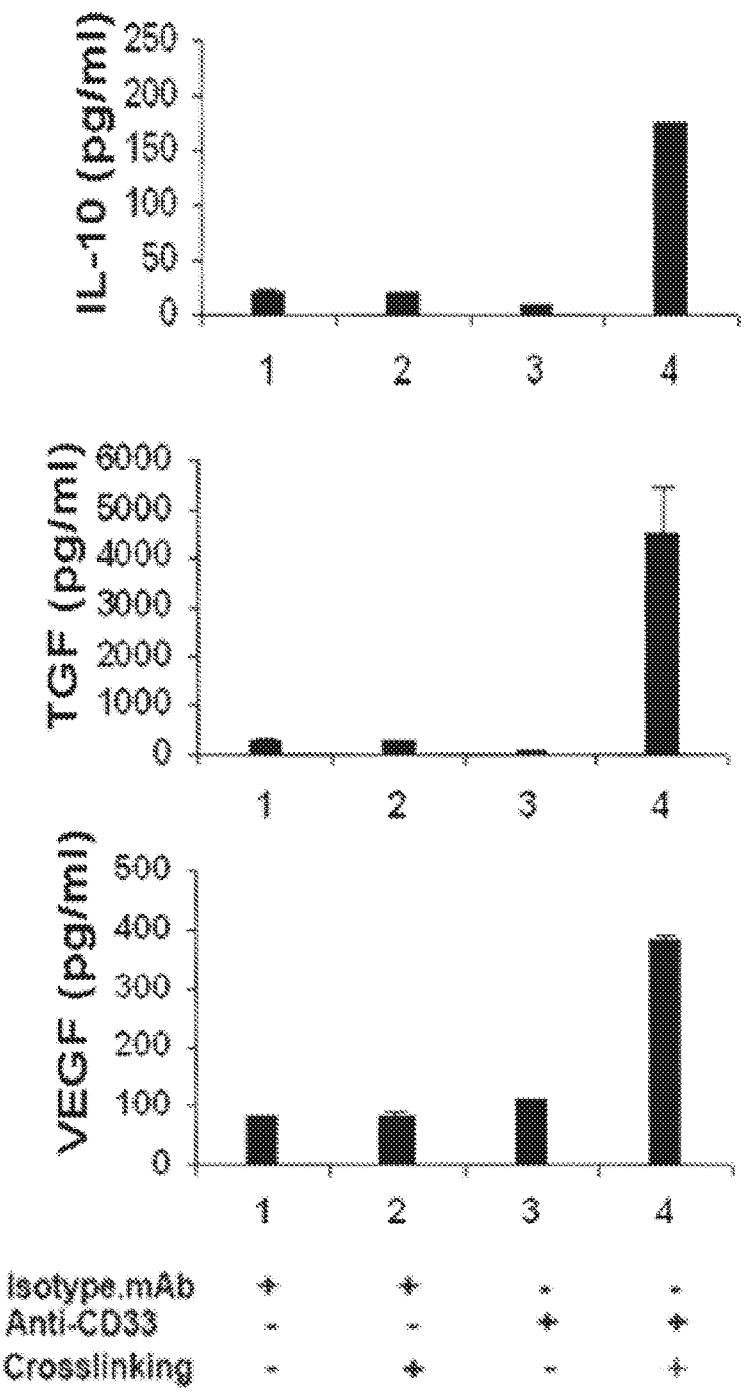
Figure 2C:
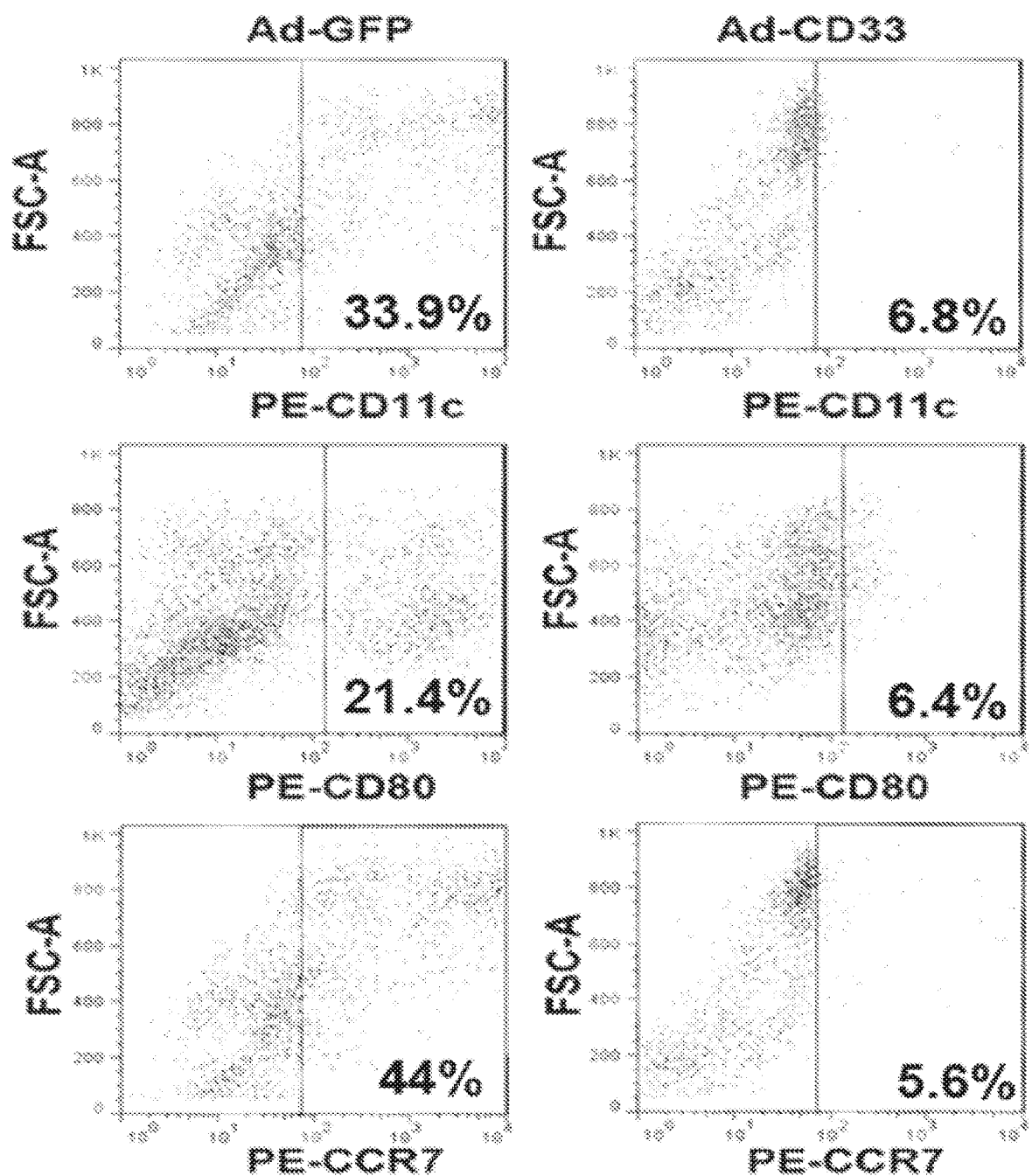
Figure 2D:
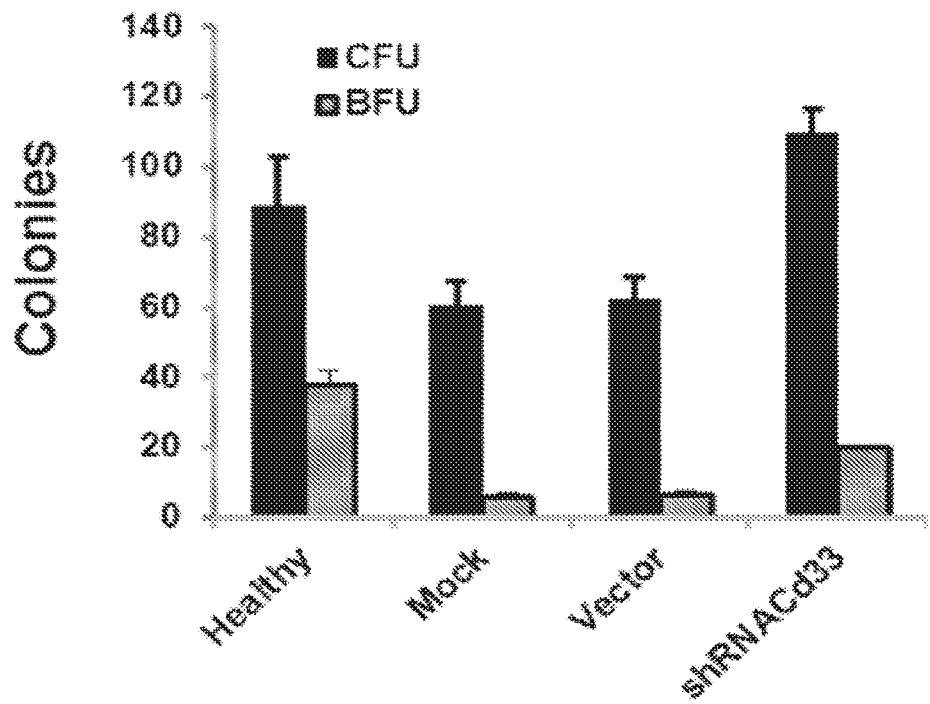
Figure 2E:
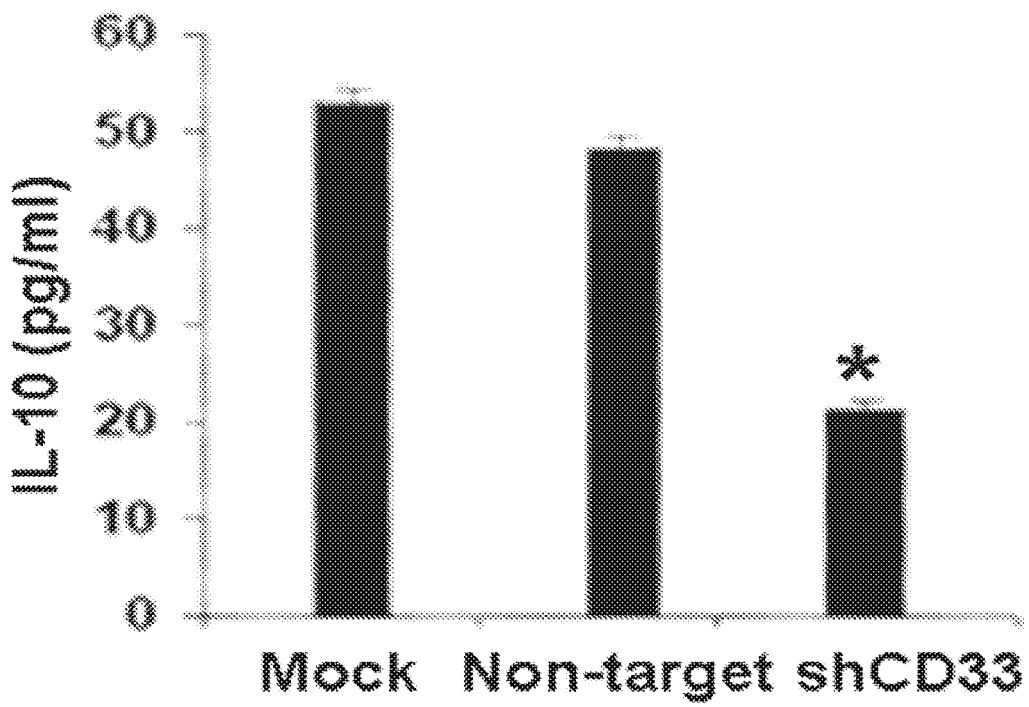
Figure 2F:
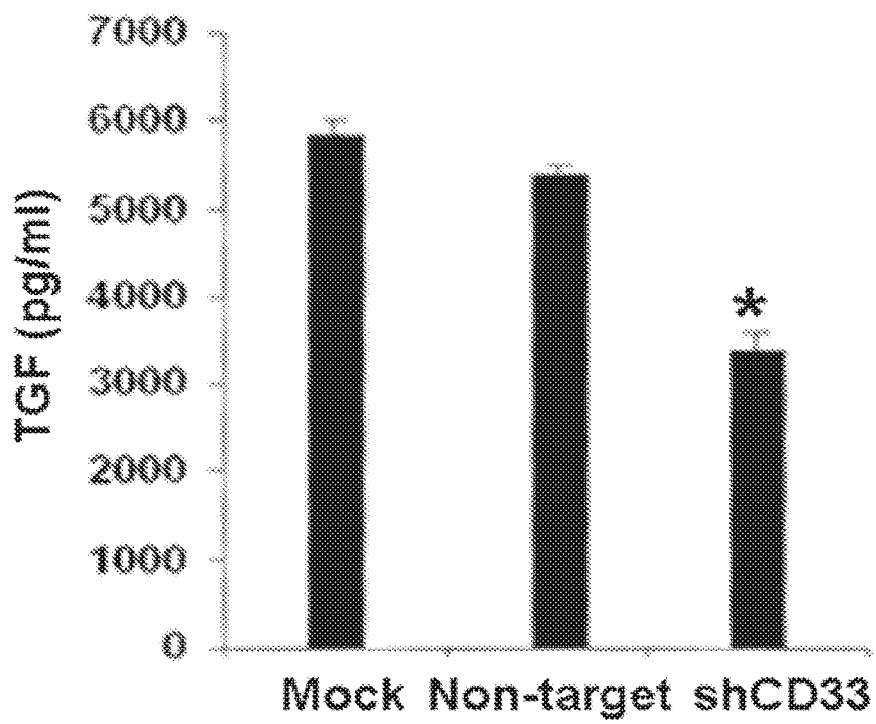
Figure 2G:
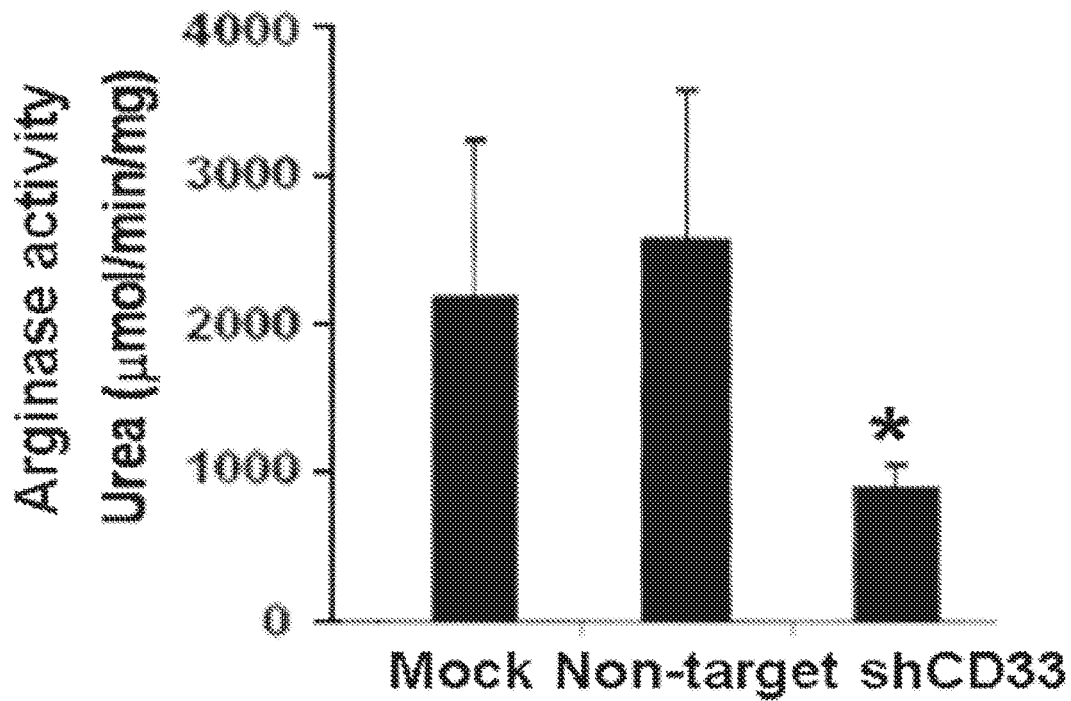

Increased CD33 expression and signaling contribute to MDSC suppressive functions and hematopoietic impairment. MDSCs in humans characteristically express the surface transmembrane glycoprotein CD33, a Siglec 3 receptor that along with other members of this family, have prominent roles in inflammation (Crocker, P. R., et al. 2007. Nat Rev Immunol 7:255-266; Blasius, A. L., et al., 2006. Blood 107:2474-2476; Blasius, A. L., et al. 2006. Trends Immunol 27:255-260; Lajaunias, F., et al. 2005. Eur J Immunol 35:243-251; Nutku, E., et al. 2003. Blood 101: 5014-5020; von Gunten, S., et al. 2008. Ann N Y Acad Sci 1143:61-82; Paul, S. P., et al. 2000. Blood 96:483-490; Ulyanova, T., et al. 2001. J Biol Chem 276:14451-14458; Avril, T., et al. 2004. J Immunol 173:6841-6849; Ikehara, Y., et al. 2004. J Biol Chem 279:43117-43125). However, the involvement of CD33 in myelopoiesis remains unexplored. Hence, the relationship between CD33 membrane expression density on MDS-MDSC and their activation and maintenance in MDS BM was investigated. These cells were found to robustly express CD33 at levels higher than LIN⁻ HLA-DR⁻CD33 cells isolated from non-MDS-associated cancer patients and healthy donor BM cells (FIG. 2A). To explore the functional consequences of CD33 engagement, CD33 was cross-linked in U937 cells (a human rnonocytic cell line with high CD33 expression), which triggered IL-10, TGF-β and VEGF secretion (FIG. 2B). To examine whether CD33 can promote MDSC accumulation and/or activation, CD33 was overexpressed with an adenovirus vector in BM-MNC from healthy donors, which significantly suppressed myeloid cell development as evidenced by reduced expression of the maturation markers CD11c, CD80, and CCR7 (FIG. 2C). To further establish the role of CD33 in MDSC-mediated BM suppression, CD33 was knocked down in MDS-MDSC using a lentiviral vector (LV) containing CD33-specific-shRNA. Co-culture of autologous HPCs with CD33 shRNA-treated MDS-MDSCs resulted in a 2-3 fold increase in BFU-E and CFU-GM colony recovery compared to those cultured with scrambled shRNA-treated and non-transduced MDS-MDSCs and healthy donor BM MDSCs (FIG. 2D). Moreover, production of IL-10, TGF-β, and arginase was reduced in CD33 snRNA-treated MDS-MDSC compared to control cells (FIG. 2E, F, G). Collectively, these data delineate a role for CD33 in MDSC activation and expansion in MDS and directing hematopoietic impairment.

Figure 3A:
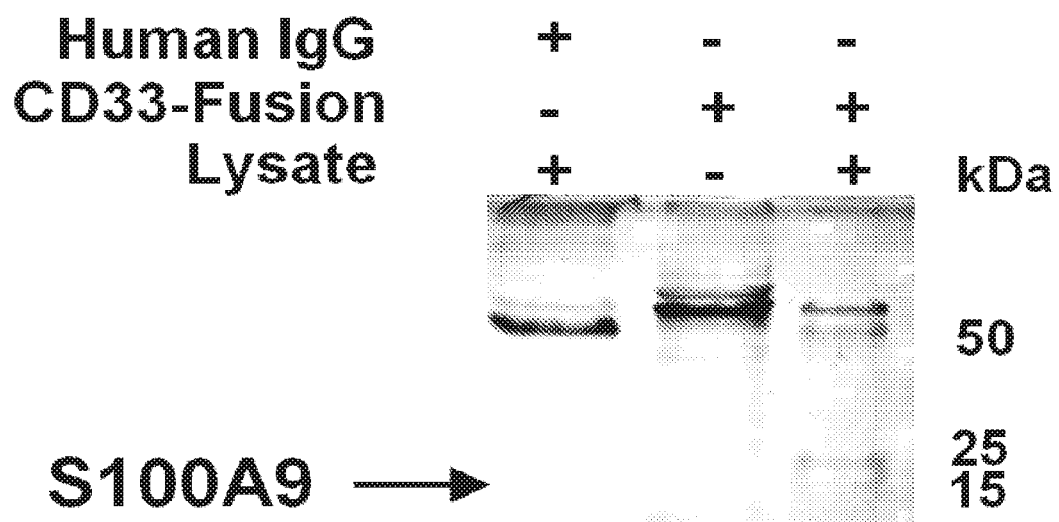
FIGS. 3A to 3O show identification of S100A9 as a native ligand for CD33.
Figure 3B:
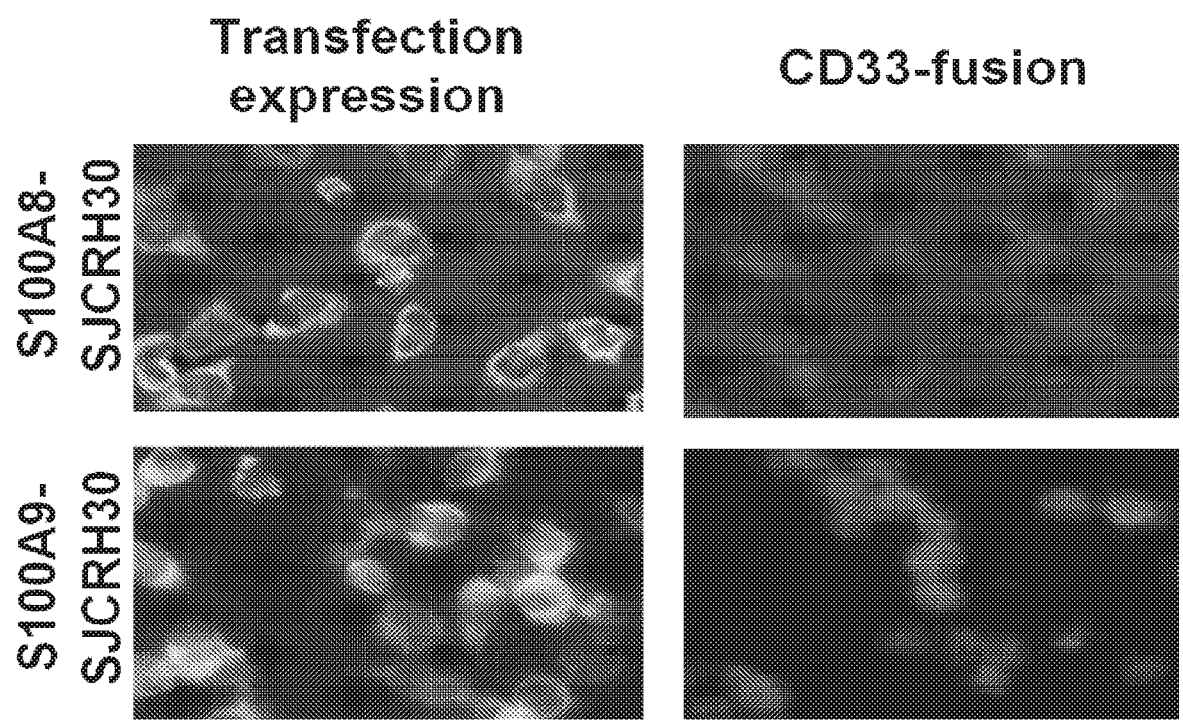
FIG. 3B shows transfected SJCRH30 cells (S100A8 on top left and S100A9 lower left) stained with CD33-fusion (APC).
Figure 3G:
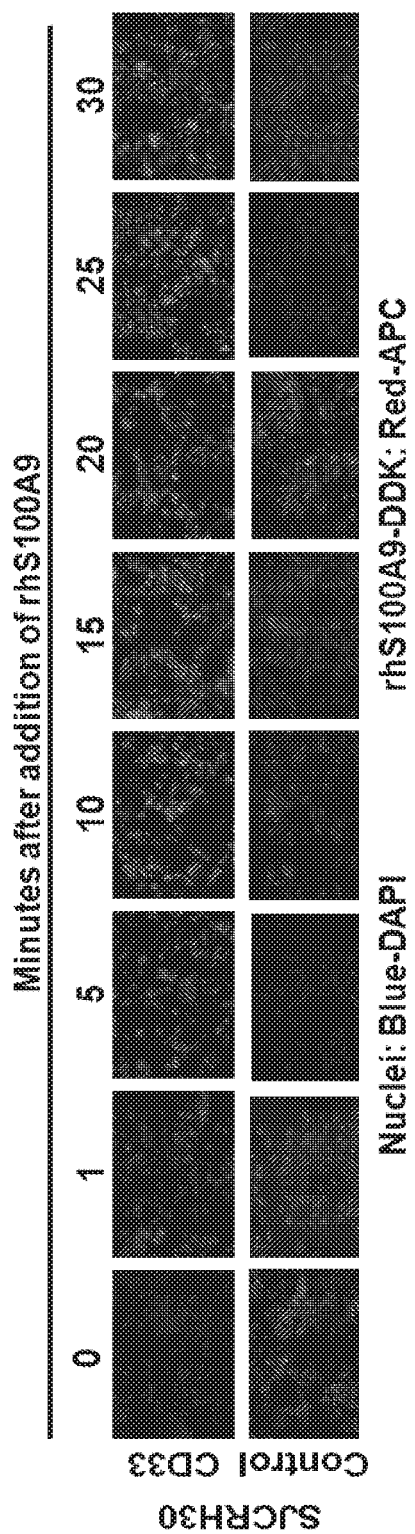
FIG. 3G shows immunofluorescence staining of recombinant human S100A9-DDK incubated with either CD33-transfected (top panel) or vector-transfected (lower panel) SJCRH30 cells at indicated time points. DAPI=nuclei, APC-DDK=rhS100A9.
Figures 3H, 3I:
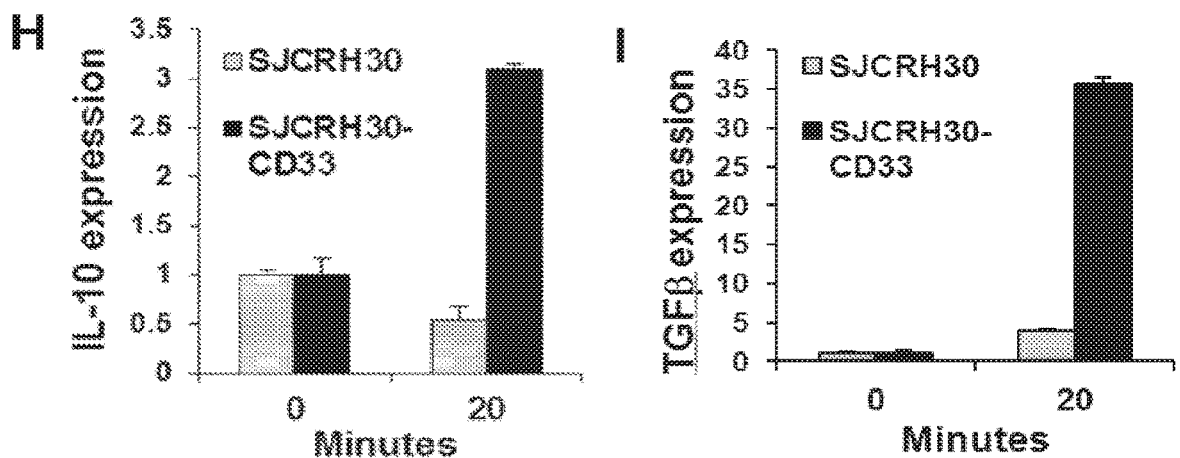
FIGS. 3H to 3I show treatment of SJCRH30-CD33 cells with rhS100A9 induced IL-10 (FIG. 3H) and TGF-β expression (FIG. 3I).
Figures 3J, 3K, 3L:
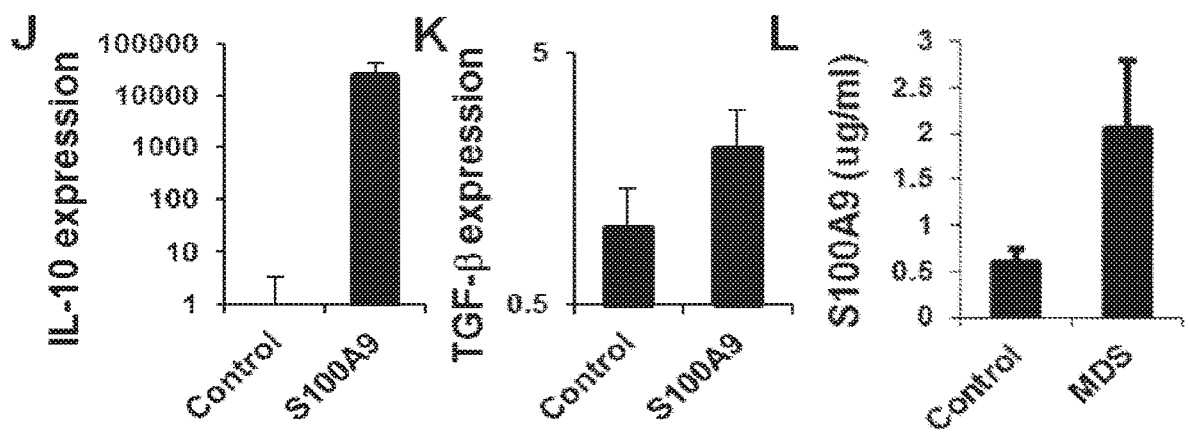
FIGS. 3J to 3K show treatment of U937 cells (high CD33 expression myeloid cell line) with rhS100A9 also induces IL-10 (FIG. 3J) and TGFβ expression (FIG. 3K).
FIG. 3L shows S100A9 protein concentration in the plasma of MDS patients (n=6) measured by ELISA.
Figure 3M:
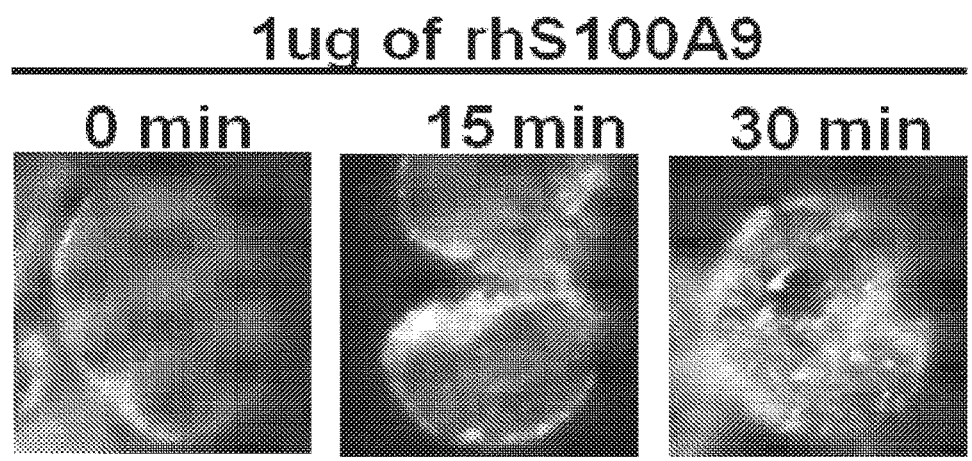
FIGS. 3M to 3N show MDS-MDCS treated with 1 μg of rhS100A9 stained for CD33-FITC and anti-DDK-APC (FIG. 3M) and immunoprecipitated with anti-CD33 antibody followed by blotting with anti-SHP-1 (FIG. 3N).
Figures 3N, 3O:
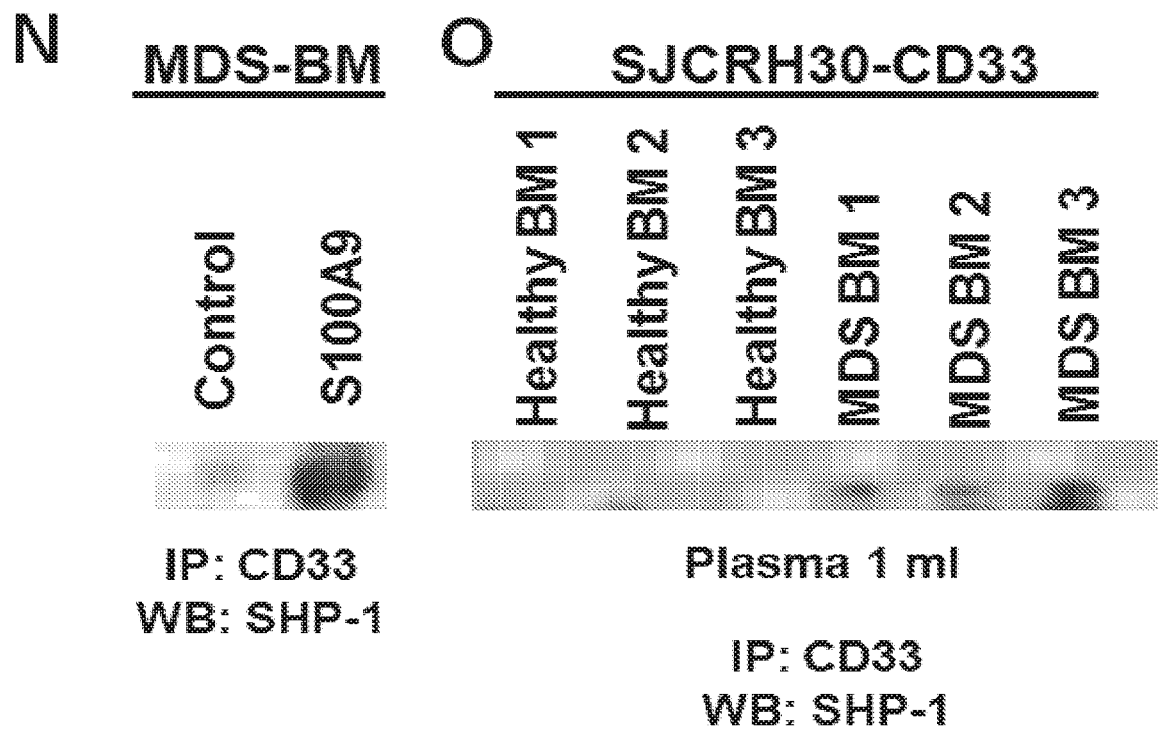

S100A9 is a native ligand for CD33. Although these investigations showed that CD33/Siglec 3 is a key receptor involved in functional activation of MDSC, its native ligand was unknown. Therefore, to identify potential ligand(s) for this receptor, a chimeric fusion protein with the ectodomain of CD33 and the Fc portion of human IgG (here on referred to as CD33-fusion) was produced. BM cell lysates from MDS patients were immunoprecipitated with the CD33-fusion followed by high throughput mass-spectrometric analysis on associated peptides. S100A9, an inflammatory signaling molecule known to activate MDSC, was among the most prominent protein bands identified (FIG. 3A). To confirm the specificity of the binding of this DAMP to CD33 both S100A8 and S100A9 transfectants were prepared in the rhabdomyosarcoma cell line SJCRH30, which lacks detectable expression of endogenous CD33, S100A8 or S100A9. The CD33-fusion (APC) stained only S100A9 transfected cells, but not S100A8 transfected cells, confirming binding specificity (FIG. 3B. Transfectants were stained with FITC and specific binding by the CD33-fusion was stained with APC, (nuclei were stained with DAPI). Direct binding of S100A9 to CD33 was confirmed further in a sandwich ELISA where the capture antibody was anti-S100A9 (FIG. 3C) as well as by dot blot analysis of transfected cell lysates with CD33-fusion (FIG. 3D), demonstrating the specificity of the interaction. To fully corroborate the binding of this pair, a reverse immune-precipitation was performed on CD33 transfected cells showing that S100A9 co-precipitated with CD33 only in S100A9 co-transfected cells (FIG. 3E). To validate clinically the ligand specificity in MDS patients, the pull-down was compared with CD33-fusion from healthy PBMC and BM as well as MDS patients. As expected, the highest amount of S100A9 was precipitated from the BM of MDS patient specimens (FIG. 3F). Next, to understand the kinetics of S100A9 and CD33 interactions, SJCRH30 cells were transfected with either vector or CD33 and incubated with recombinant human (rh) S100A9 tagged with DDK (DYKDDDDK (SEQ. ID. No. 9) epitope, same epitope as Flag). This resulted in a time-dependent increase in binding of rhS100A9 to stable SJCRH30-CD33 cells but no binding to vector transfected cells (FIG. 3G). To demonstrate the functionality of this ligation pair, rhS100A9 was added to SJCRH30-CD33 cells which triggered CD33 mediated up-regulation of IL10 and TGFβ expression (FIGS. 3H and I). To confirm that rhS100A9 can recapitulate these observation of the secretion of these cytokines after cross-linking CD33, the experiments were repeated in U937 cells with rhS100A9 and an increase in production of both cytokines was again found (FIGS. 3J and K). Importantly, BM plasma concentration of S100A9 was significantly increased in MDS patients compared to BM plasma from healthy donors (FIG. 3L). Moreover, the engagement of CD33 with rhS100A9 in MDS-MDSC from patient BM resulted in a time-dependent co-localization of this ligand/receptor pair in primary MDS-BM cells (FIG. 3M). It is well recognized that CD33 signals through phosphorylation of ITIMs that recruit SHP-1 (Src homology region 2 domain-containing phosphatase-1). rhS100A9 ligation correspondingly increased the recruitment of SHP-1 confirming that CD33 signals through its ITIM after S100A9 ligation in MDS-BM (FIG. 3N). In addition, directly treating CD33- transfected SJCRH30 with the BM plasma of MDS patients triggered the recruitment of SHP-1 to ITIM when compared to cells treated with the plasma of healthy donors, suggesting that increased secretion of S100A9 in the local BM microenvironment may have a role in the activation of CD33-ITIM signaling (FIG. 3O).

Figures 4A, 4B:
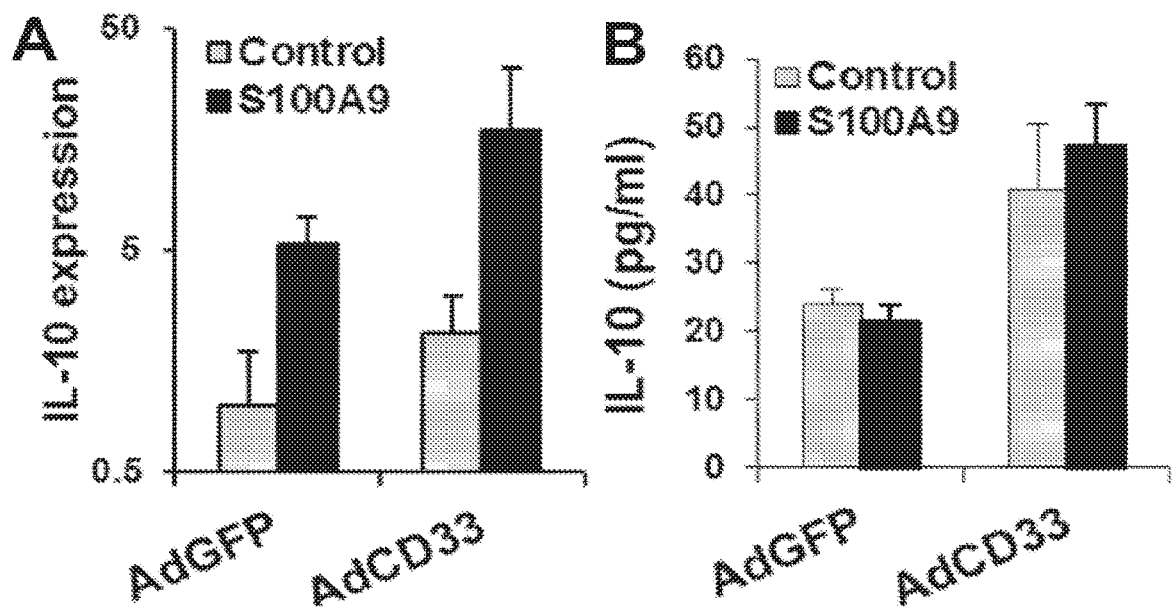
Figures 4C, 4D:
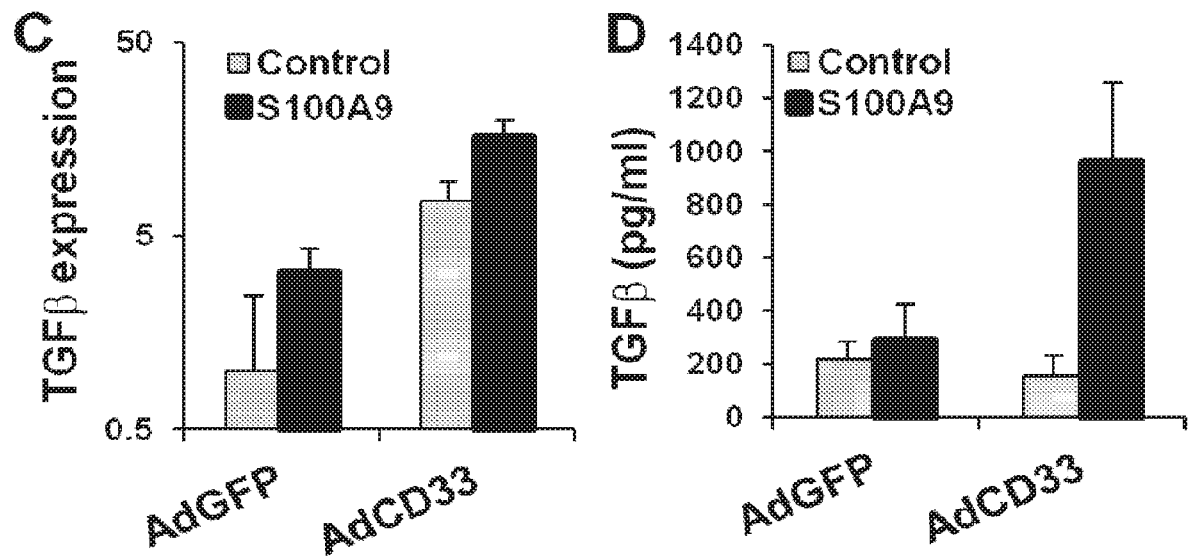
Figures 4E, 4F:
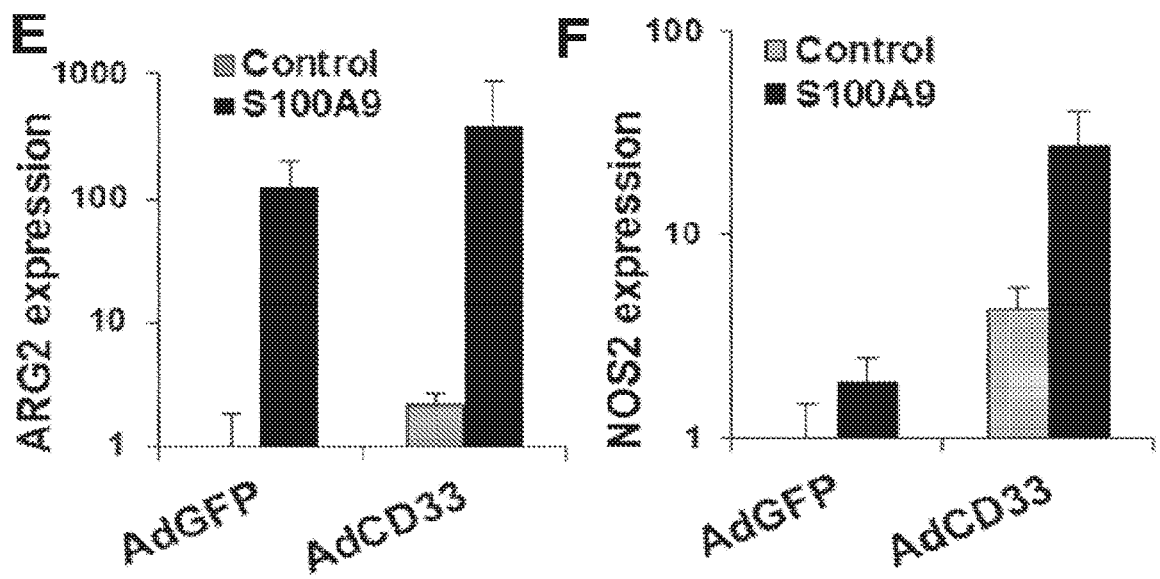
Figures 4G, 4H:
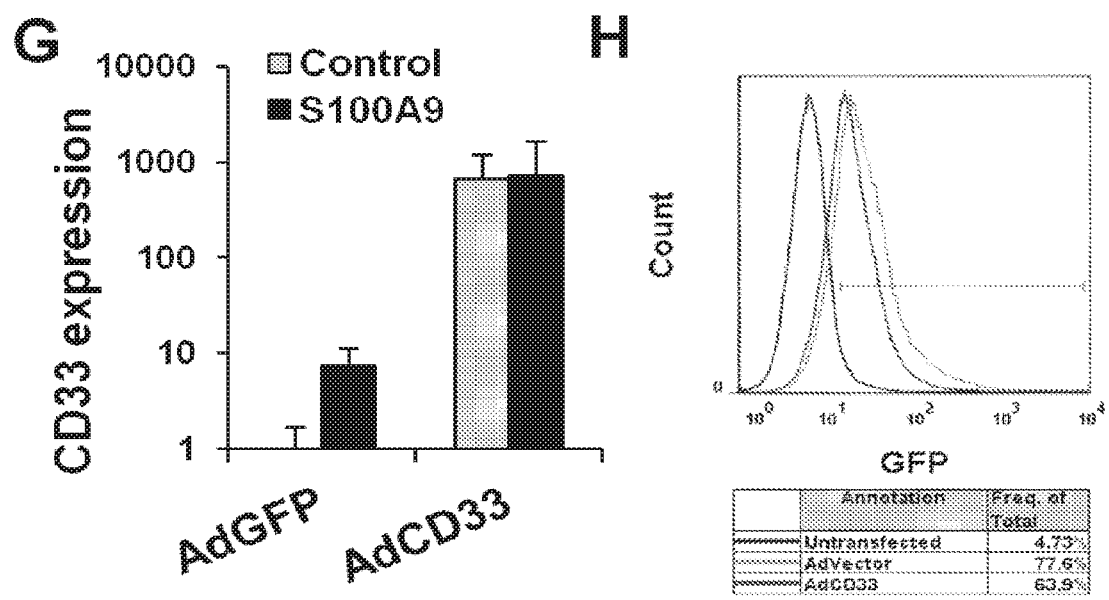

S100A8/S100A9 engagement of CD33 triggers MDS-MDSC activation. Having established S100A9 and CD33 as a functional ligand/receptor pair, the role of this interaction in replicating the functional responses observed with receptor crosslinking was explored. CD33 overexpression was again induced in healthy BM cells through adenovirus transfection and their immunosuppressive properties with or without the addition of rhS100A9 was studied. Forced expression of CD33 induced a parallel increase in gene expression and secretion of the suppressive cytokines, IL-10 and TGFβ (light grey bars, FIG. 4A-D), which was greatly increased by the addition of rhS100A9 (black bars). Secretion of the suppressive cytokine TGFβ was only observed after rhS100A9 treatment of CD33 transfected cells (FIG. 4D), accompanied by an increase in the expression of NOS2 and ARG2, consistent with the suppressive cytokine profile (FIGS. 4E and F). FIG. 4G-H demonstrates the transfection efficiency of the CD33 adenovirus at both the gene and protein expression level measured by QPCR and GET by flow cytometry, respectively.

Figure 4I:
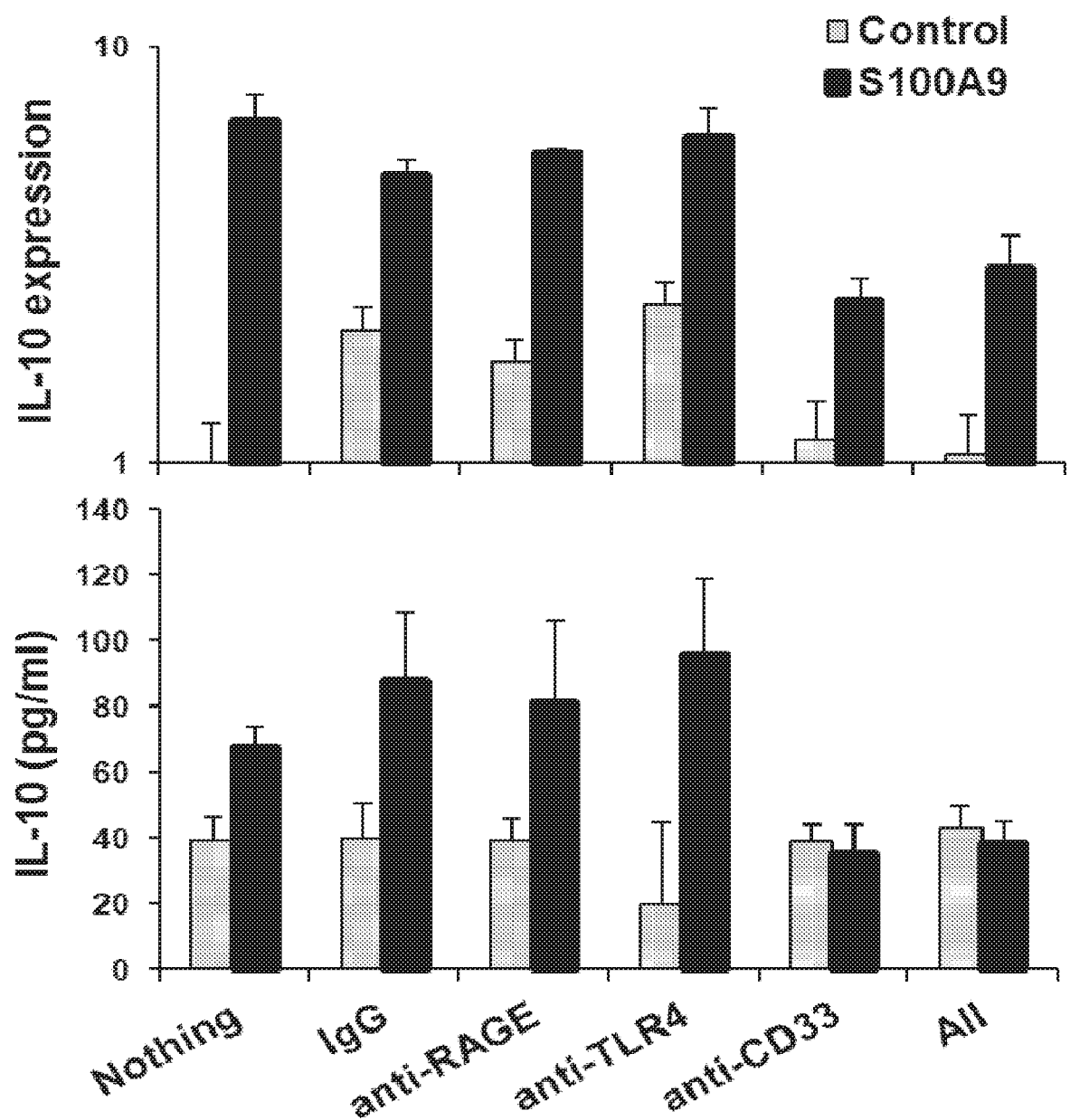
FIGS. 4I and 4J show healthy BM cells' RAGE, TLR4, CD33 or their combination blocked prior to culturing cells by themselves or with 1 ug of S100A9 for 48 hours to determine IL-10 gene and protein expression (Q-PCR and ELISA, (FIG. 4I)) or TGF-β gene and protein expression (FIG. 4J).
Figure 4J:
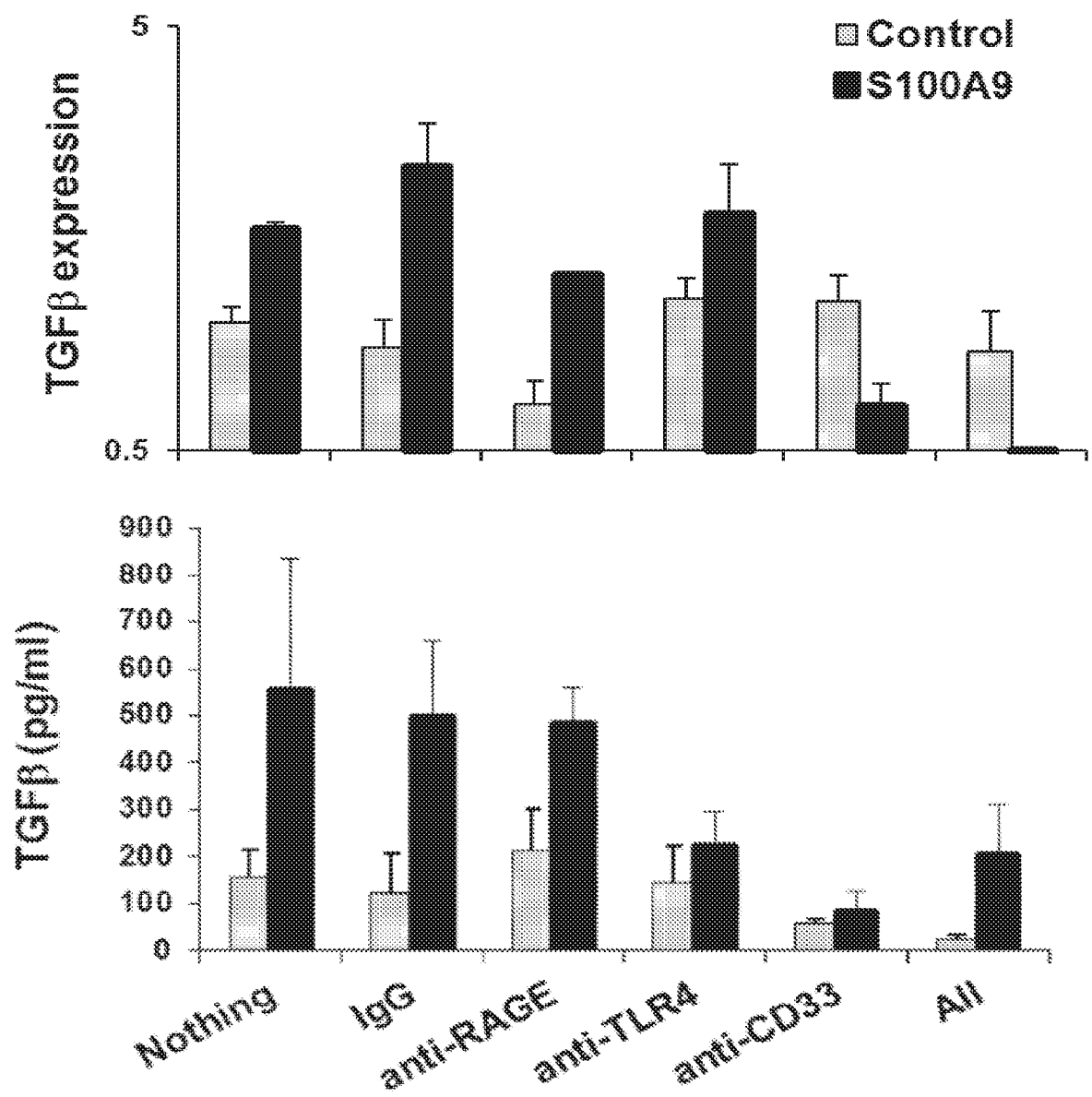
Figures 4K, 4L:
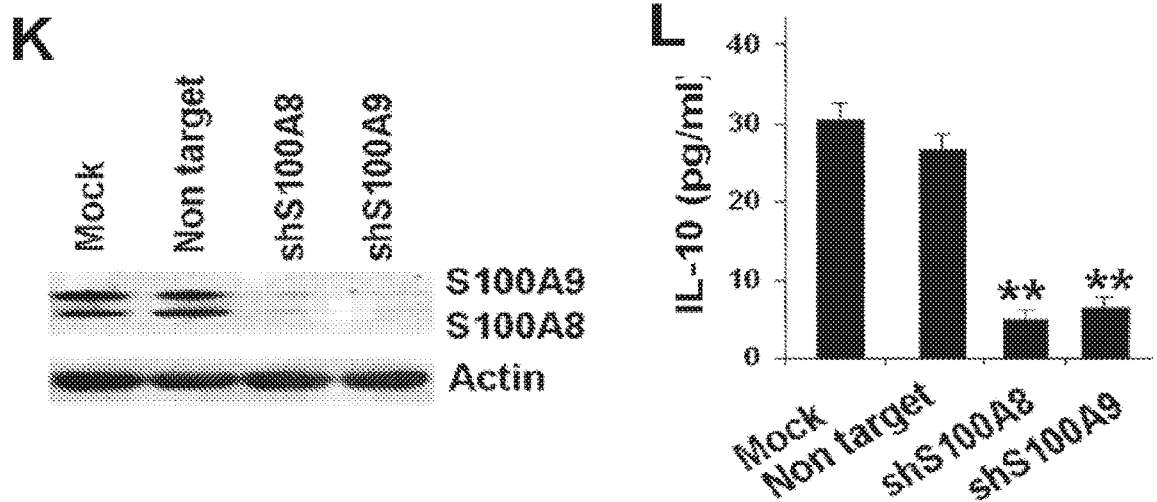
Figures 4M, 4N:
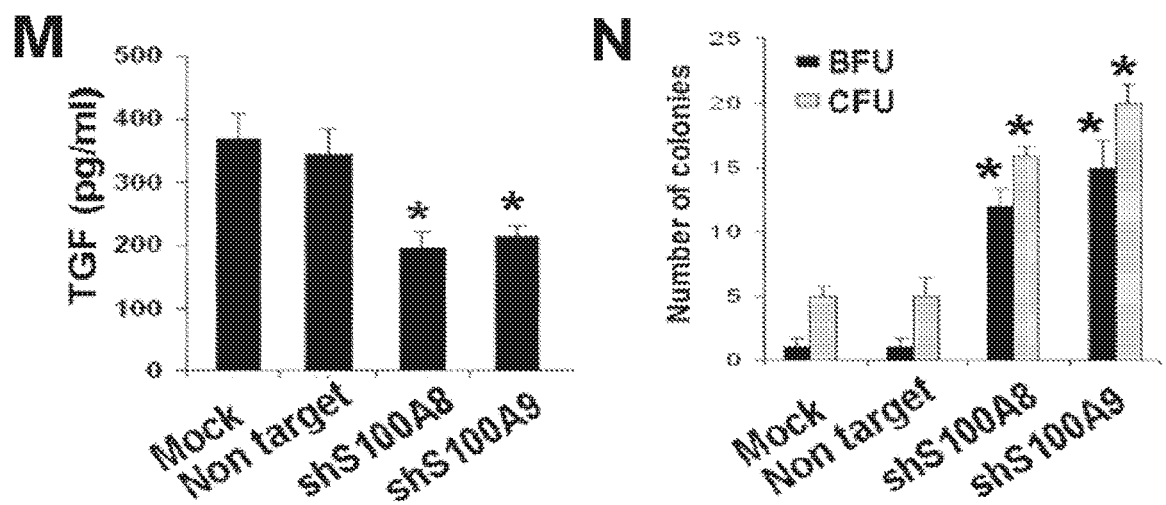

To further delineate the specific role of S100A9's ligation with CD33 compared to its other ligands, RAGE, TLR4, CD33 as well as each pair were blocked with antibodies before treating healthy BM cells with rhS100A9. These data show that blockade of CD33 reduced both IL-10 and TGFβ production, while treatment with anti-RAGE and anti-TLR4 had no significant effects on IL-10 production but displayed modest suppression of TGFβ secretion and expression (FIGS. 4I and J). These findings suggest that although CD33 plays a critical role in the secretion of both cytokines, other receptors associated with local bone marrow inflammation may also have a contribution. To confirm that S100A9 expression contributes to inflammation in the BM microenvironment, S100A8 and S100A9 were knocked down in MDS-MDSC using gene specific shRNAs (FIG. 4K). Given that S100A9 usually pairs with S100A8 as a heterodimer and are concomitantly regulated, it was not surprising that there was reciprocal changes in gene expression with downregulation in expression of the alternate protein. Importantly, reduction of S100A8/S100A9 expression profoundly attenuated IL-10 and TGF-β production (FIGS. 4L and M) and rescued autologous BFU-E and CFU-GM colony formation (FIG. 4N). These data show that inflammation-associated S100A8/S100A9 signaling plays a critical role in the activation of MDS-MDSC and suppress normal hematopoiesis.

S100A9 transgenic mice recapitulate features of human MDS. Given the findings that S100A8/S100A9 triggers CD33/Siglec 3 signaling and is involved in MDSC activation (Ehrchen, J. M., et al. 2009. J Leukoc Biol 86:557-566; Vogl, T., et al. 2007, Nat Med 13:1042-1049; Cheng, P., et al. 2008. J Exp Med 205:2235-2249), S100A9 transgenic mice (S100A9Tg) were generated to study MDSC-associated inflammation (Cheng, P., et al. 2008. J Exp Med 205:2235-2249). Since MDS is an age-associated disease, changes in the proportion of BM MDSC (Gr1$^+$CD11b$^+$ cells) with age were analyzed in S100A9Tg compared to S100A9 knockout (S100A9KO)(Manitz, M. P., et al. 2003. Mol Cell Biol 23:1034-1043) or wild-type (WT) mice at 6, 18 or 24 weeks of age. This resulted in a marked age-dependent accumulation of MDSC in the BM of S100A9Tg mice, but not in S100A9KO or WT mice, that reached its maximum by 24 weeks (FIG. 5A). Similarly, the proportion of MDSC in PBMC and spleen also increased with age (FIG. 5B). Although changes in the proportion of MDSC in the spleen was comparatively less than in the BM, it was accompanied by a decrease in the proportion of mature cells (FIGS. 5C and 5D), effectively increasing the ratio of immature to mature cells in this hematopoietic organ. Functionally, only the MDSC from 24-week old S100A9Tg mice, but not S100A9KO or WT mice, significantly inhibited BFU-E (FIG. 5E) and CFU-GM formation, which was rescued after depletion of MDSC in the S100A9Tg group (FIG. 5E). Importantly, as further evidence of the role of S100A9 as an essential inflammatory factor regulating MDSC expansion and suppressive activity, IL-10 and TGF-β secretion was significantly increased in S100A9Tg mice compared to KO or wild-type animals (FIG. 5F).

Figures 5O, 5P:
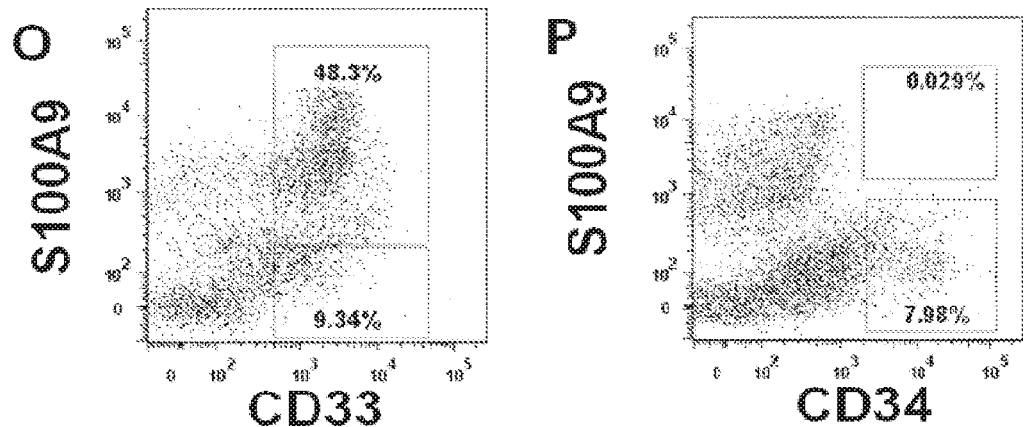

To evaluate the in vivo consequences of S100A9 overexpression on hematopoiesis, serial complete blood counts (CBC) were analyzed from WT and S100A9Tg mice at 6, 18 and 24 weeks of age. S100A9Tg mice developed progressive muitilineage cytopenias characterized by decreasing hemoglobin (Hgb), red blood cell (RBC) number, neutrophil and platelet counts evident as early as 6 weeks of age. By 18 weeks, S100A9Tg mice exhibited severe anemia and thrombocytopenia with a greater than 22.0% decrease in RBC, 20.1% decrease in Hgb, and 77.8% decrease in platelets (Table 2). Histological examination of BM aspirates and biopsy sections from WT mice displayed normal morphology and cytological features (FIG. 5G-J). In contrast, the BM of S100A9Tg mice was hyper-cellular (95% cellularity) accompanied by tri-lineage cytological dysplasia (FIG. 5K-N). Megakaryocyte morphology recapitulated the dysplastic features characteristic of human MDS, with a preponderance of mononuclear or hypolobated forms. Erythroid precursors displayed megaloblastoid maturation with abnormal hemoglobination and occasional binucleation. Nuclear budding and bizarre mitotic forms were also apparent (FIG. 5K-N). Cytopenias worsened with age and by 24 weeks S100A9Tg mice developed severe pan-cytopenia (detailed descriptions summarized in the figure legend). Although this model closely replicates the inflammatory milieu observed in human MDS, HSPC from S100A9Tg mice also express the S100A9 protein. Given that the provenance of this protein in human MDS is not known, cellular expression of S100A9 in MDS BM-MNC was investigated by flow cytometry. S100A9 intracellular staining was detected in CD33$^+$ cells, whereas CD34$^+$ HSCs had no demonstrable S100A9 expression (FIGS. 5O and 5P). S100A9 expression was not detected in other immune cells such as CD3$^+$ lymphocytes, CD19$^+$ B cells or CD56$^+$ NK cells.

TABLE 2

Complete peripheral blood count of S100A9Tg and wt-mice

| Test | Units | 6 weeks WT | 6 weeks S100A9-Tg | 18 weeks WT | 18 weeks S100A9-Tg | 24 weeks WT | 24 weeks S100A9-Tg |
|---|---|---|---|---|---|---|---|
| WBC | 10$^3$/μl | 5.4 ± 0.5 | 4.2 ± 1.5 | 6.0 ± 1.4 | 2.9 ± 0.2* | 6.3 ± 0.8 | 3.0 ± 0.4* |
| LYM | 10$^3$/μl | 3.9 ± 0.5 | 2.6 ± 1.2 | 4.7 ± 1.1 | 2.4 ± 0.1* | 4.8 ± 0.7 | 2.5 ± 0.3* |
| MONO | 10$^3$/μl | 0.4 ± 0.1 | 0.3 ± 0.2 | 0.4 ± 0.1 | 0.2 ± 0.1* | 0.4 ± 0.1 | 0.2 ± 0.1* |

TABLE 2-continued

Complete peripheral blood count of S100A9Tg and wt-mice

| | | 6 weeks | | 18 weeks | | 24 weeks | |
|---|---|---|---|---|---|---|---|
| Test | Units | WT | S100A9-Tg | WT | S100A9-Tg | WT | S100A9-Tg |
| GRAN | $10^3/\mu l$ | 1.1 ± 0.6 | 1.2 ± 1.2 | 0.9 ± 0.3 | 0.3 ± 0.2* | 1.1 ± 0.4 | 0.3 ± 0.1** |
| HCT | % | 48.1 ± 3.2 | 42.4 ± 2.1 | 45.7 ± 0.7 | 35.5 ± 3.0** | 45.4 ± 3.5 | 32.1 ± 2.7** |
| MCV | fl | 51.4 ± 1.6 | 49.8 ± 2.0 | 50.3 ± 0.5 | 50.0 ± 1.2 | 50.0 ± 1.3 | 50.0 ± 1.6 |
| RDWa | fl | 35.0 ± 0.7 | 33.2 ± 2.2 | 34.0 ± 1.3 | 32.5 ± 1.7 | 33.3 ± 1.4 | 32.2 ± 1.5 |
| RDW % | % | 16.3 ± 0.7 | 15.9 ± 0.1 | 16.3 ± 0.5 | 15.5 ± 0.5 | 16.0 ± 0.5 | 15.4 ± 0.6 |
| HGB | g/dl | 14.2 ± 0.8 | 13.0 ± 0.7 | 13.9 ± 0.3 | 11.1 ± 0.7** | 13.7 ± 0.6 | 10.3 ± 0.5** |
| MCHC | g/dl | 29.5 ± 1.1 | 30.6 ± 1.3 | 30.4 ± 0.4 | 31.5 ± 0.9 | 30.3 ± 1.0 | 32.3 ± 1.1 |
| MCH | pg | 15.1 ± 0.3 | 15.2 ± 0.1 | 15.3 ± 0.1 | 15.8 ± 0.3 | 15.2 ± 0.2 | 16.2 ± 0.4 |
| RBC | $10^6/\mu l$ | 9.4 ± 0.7 | 8.5 ± 0.4 | 9.1 ± 0.1 | 7.1 ± 0.6** | 9.1 ± 0.3 | 6.4 ± 0.2*** |
| PLT | $10^3/\mu l$ | 555.7 ± 96.6 | 412.0 ± 124.0 | 431.3 ± 33.9 | 95.7 ± 35.0*** | 437.0 ± 41.9 | 61.0 ± 23.5*** |

Figure 6A:
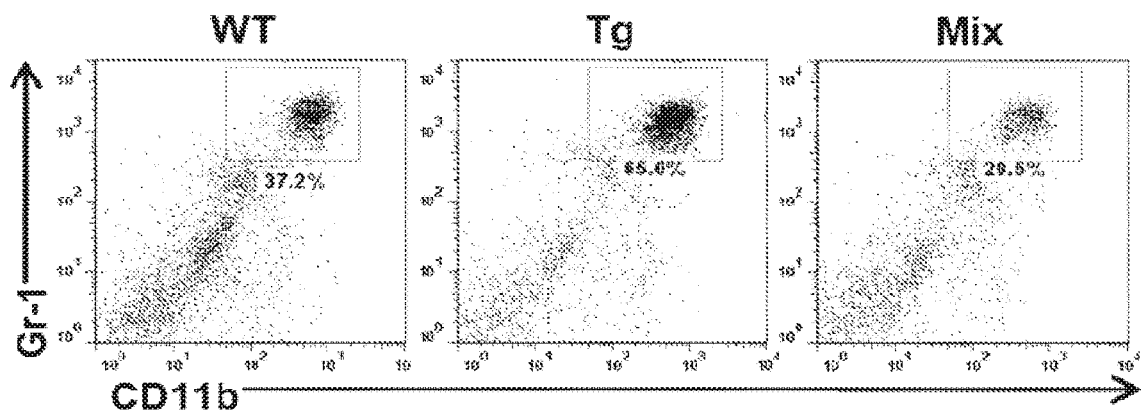
FIGS. 6A to 6I show mix transplant of S100A9 enriched HSC and WT HSC continues effects on hematopoiesis.
Figure 6B:
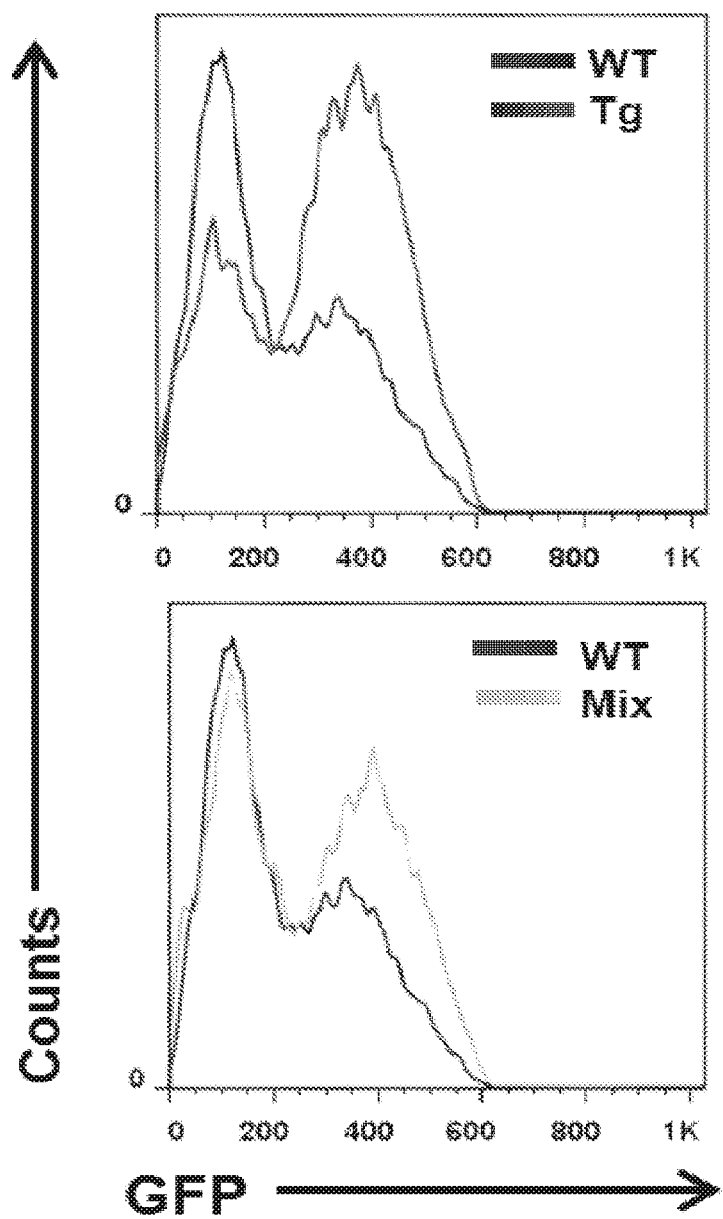
Figure 6C:
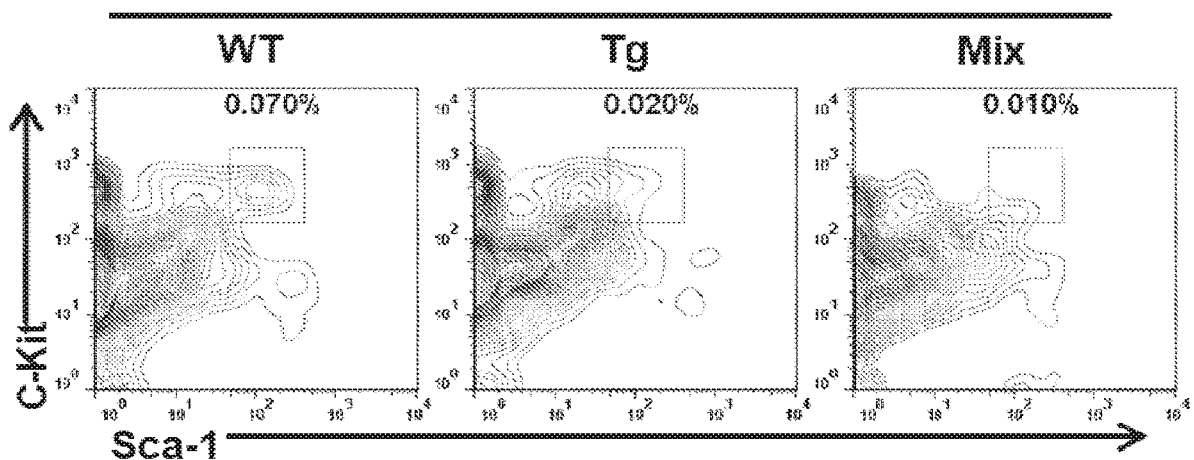
Figure 6D:
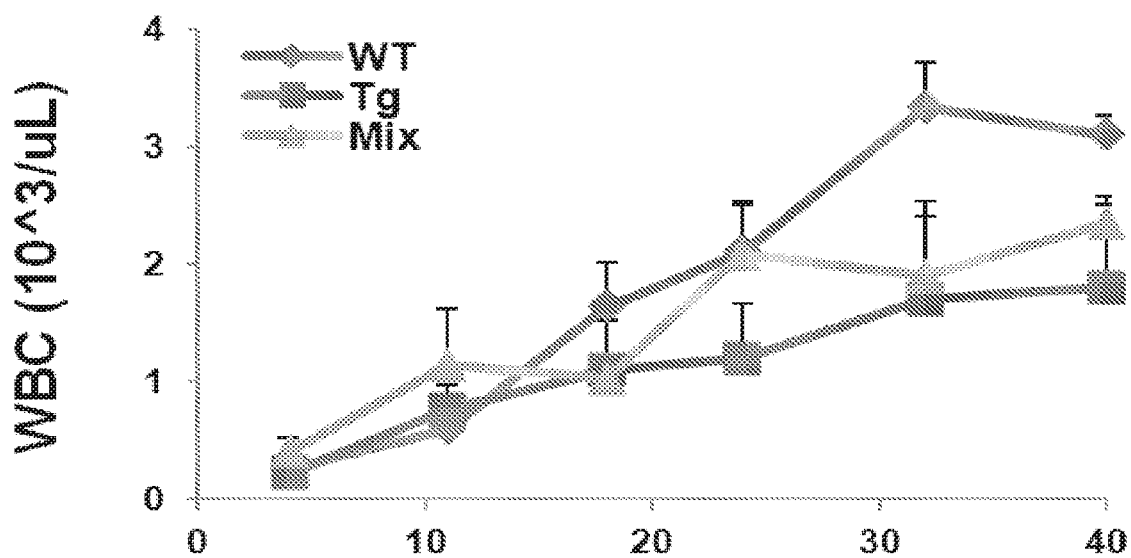
Figure 6E:
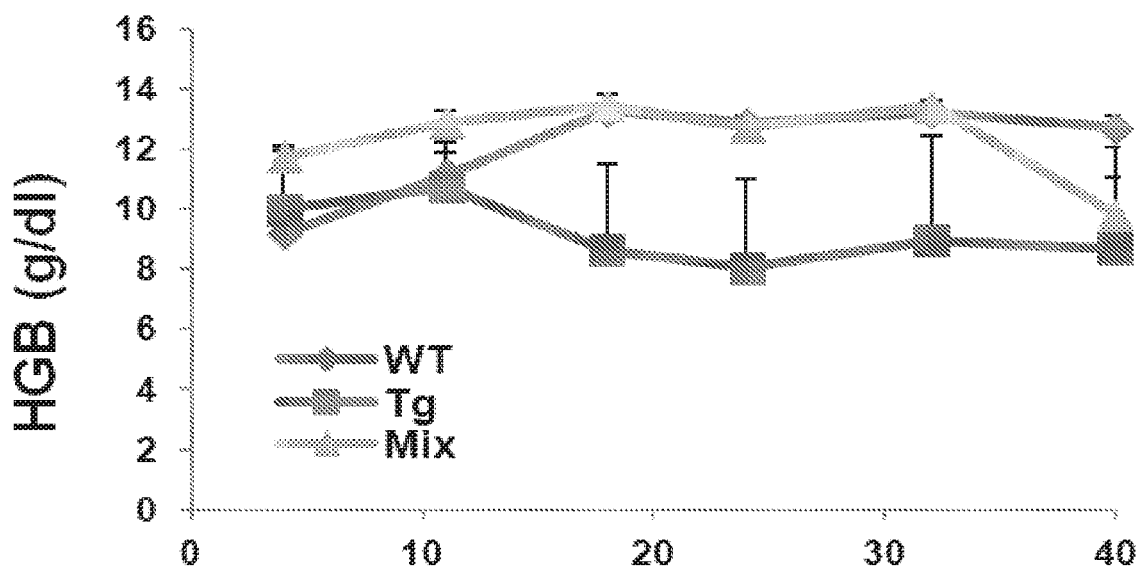
Figure 6F:
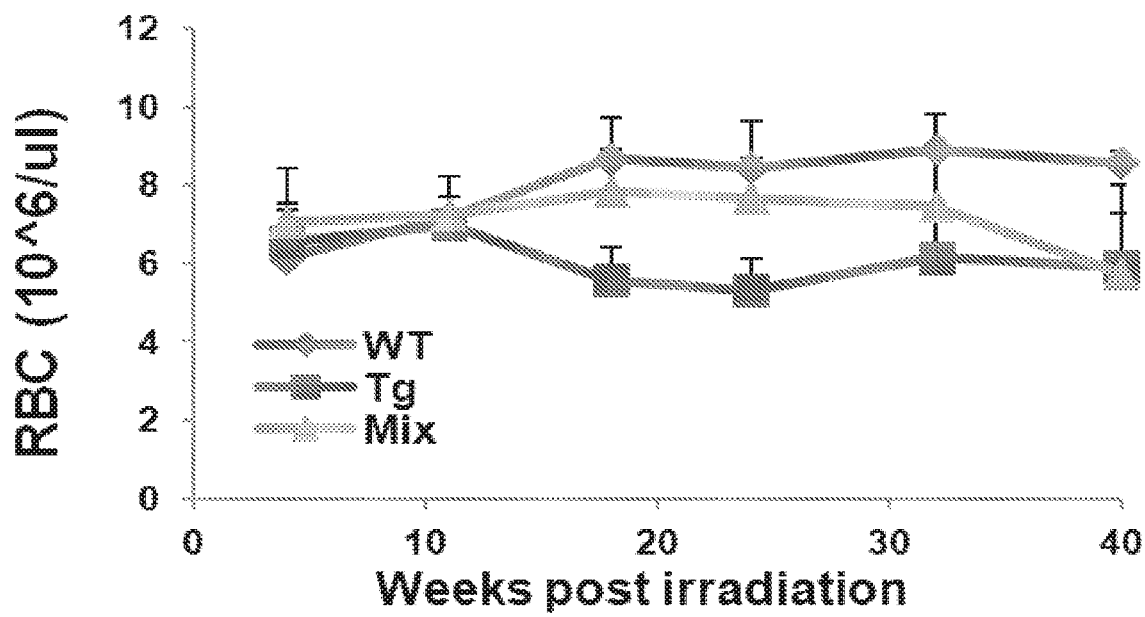
Figure 8:
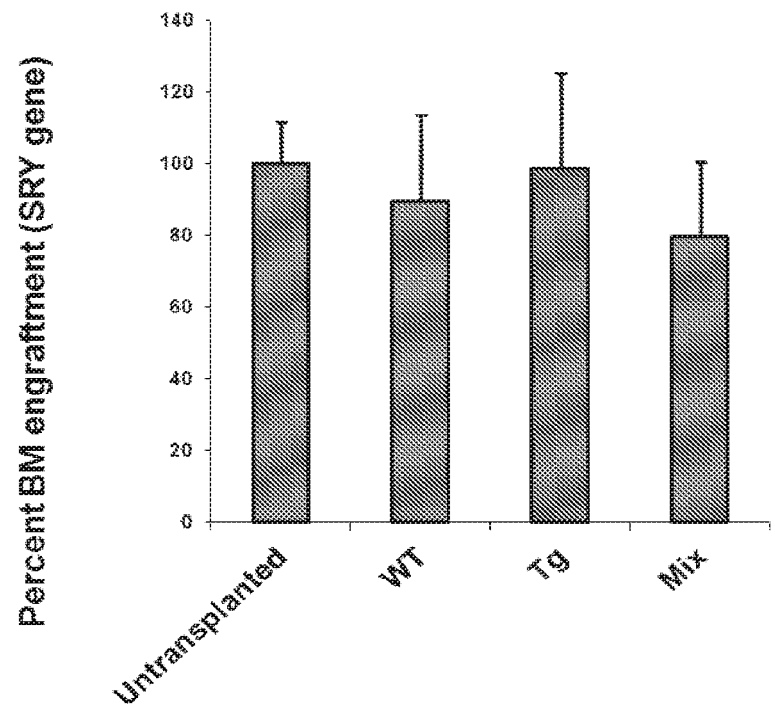
FIG. 8 shows percent engraftment in transplanted mice. Wild type female FVB/NJ mice were transplanted with enriched HSC from either WT, S100A9Tg or a 1:1 ratio of WT:Tg male cells. The percent of engraftment was assessed by measuring the expression of the SRY gene by qPCR normalized against un-transplanted male mice BM cells. GAPDH serves as the internal control.

All data are means ± SEM (n = 3-5 mice).
Peripheral blood samples were prepared from both S100A9Tg and control (WT) mice in ages of 6, 18 and 24 weeks and analyzed on a Hema True Hematology Analyzer (Heska).
*p < 0.05;
**p < 0.01;
***p < 0.001 vs wt-mice Analysis of the role of MDSC by adoptive transfer of enriched HSC from S100A9Tg mice. To more accurately delineate the role of MDSC from S100A9Tg mice in hematopoiesis, competitive adoptive transfer was performed of enriched HSCs into lethally irradiated (900 cGy) female FVB/NJ mice with age-matched WT HSC, S100A9Tg HSC or an admixture (1:1 ratio) of enriched BM HSCs from male mice. Using a male to female SRY gene expression PCR approach to monitor engraftment, all mice experienced greater than 80% engraftment (FIG. 8). After engraftment (defined as WBC>$3\times10^3$ cells/uL in WT recipients at 8 weeks), recipients of WT HSC had proportions of both BM derived Gr1$^+$Cd11b$^+$ and HSCs (FIGS. 6A and C) that were comparable to levels un-transplanted WT mice (FIG. 5A). In contrast, adoptive transfer with S100A9Tg enriched HSCs generated a high proportion of GFP expressing Gr1$^+$Cd11b$^+$ MDSCs (FIG. 6B) accompanied by a reduced proportion of HSCs, findings analogous to our observations in older transgenic mice (FIG. 6C). However, mice that received the admixed HSC population had a proportion of MDSCs approaching that in WT adoptively transferred mice (~30%). Notably, nearly 50% of MDSCs lacked GFP expression, indicating origination from WT HSPCs (FIG. 6B), whereas the remaining GET$^+$ MDSC derived from S100A9Tg donor cells. Although the total MDSC population did not increase to the level observed in the S100A9Tg adoptively transferred mice, a decreased proportion of HSCs to levels found in mice transplanted with S100A9Tg donor cells was observed (FIG. 6C). These findings indicate that the smaller population of activated MDSCs from S100A9Tg donor cells had sufficient suppressive activity to yield a comparable impairment of hematopoietic integrity. These findings were supported by sequential analyses of peripheral blood counts in which mixed source transplant recipients had cytopenias that were intermediate in severity relative to those in mice receiving the S100A9Tg or WT donor cells (FIG. 6D, E, F). Interestingly, while mixed donor recipients had the same proportion of HSCs after engraftment as Tg transplanted mice, their WBC counts were higher than mice transplanted with S100A9Tg HSC and lower than levels in WT HSC recipients. Similarly, onset of anemia was delayed in recipients of the mixed versus S100A9Tg donor cells. These findings suggest that normal HSC from WT mice are able to partially rescue hematopoiesis, but with time hematopoiesis is suppressed by accumulating MDSC derived from S100A9Tg donor cells.

Figure 6G:
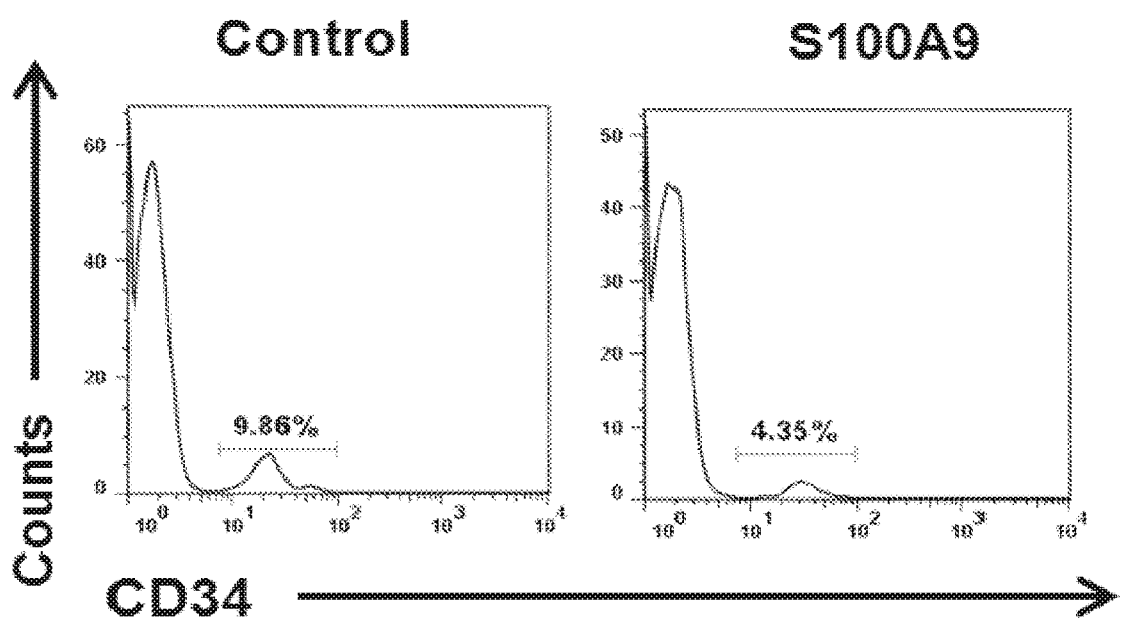
Figure 6H:
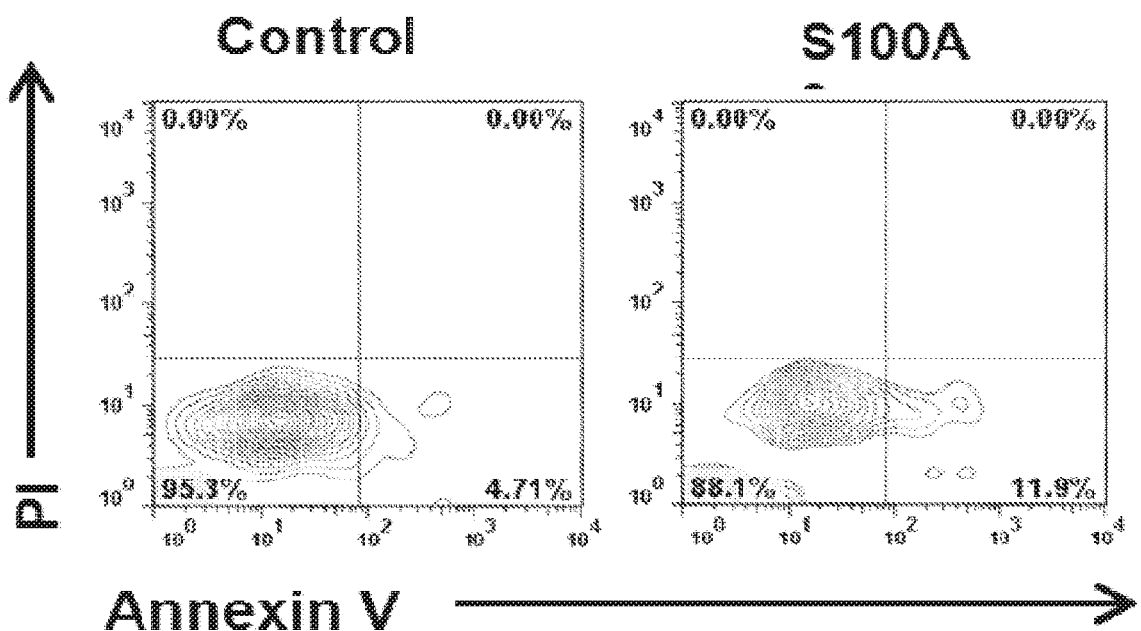
Figure 6I:
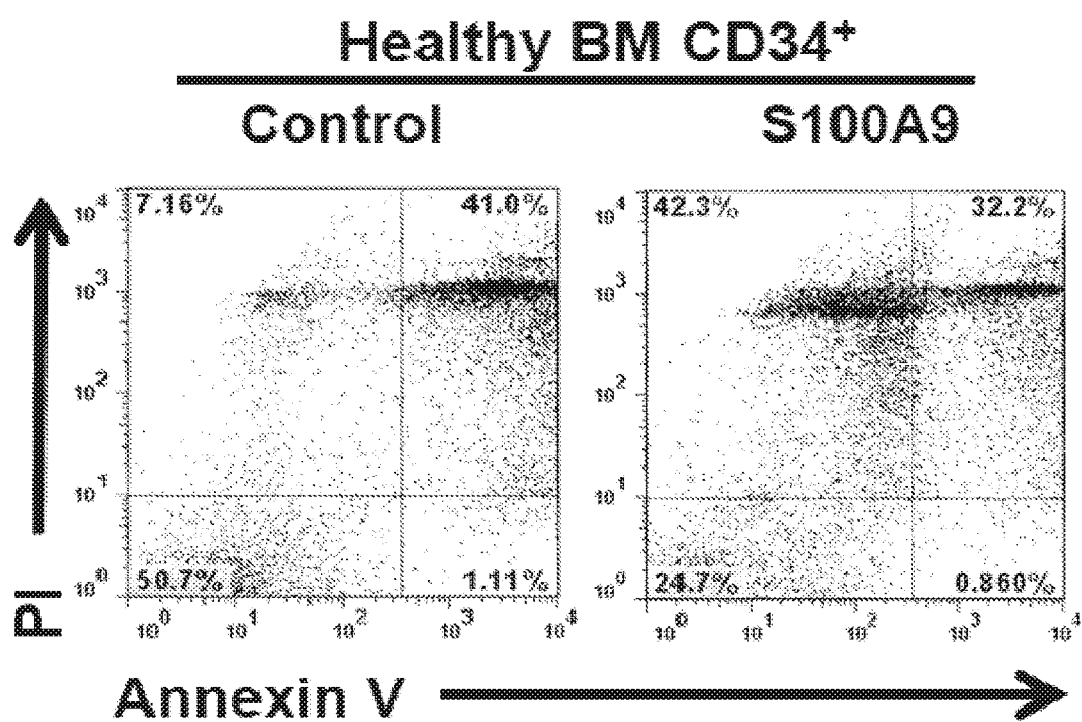

To address whether S100A9 alone has direct effects on HSCs, BM CD34±(MDSC depleted, MDSC−) from MDS patient specimens were treated with rhS100A9 for 24 and 48 hours and assessed apoptosis by flow cytometry. A decrease in the number of CD34$^+$ HSPCs was observed after treatment compared to controls accompanied by a corresponding increase in the apoptotic fraction among surviving cells after 48 hours exposure (FIGS. 6G and H). In order to corroborate these findings, healthy bone marrow-derived CD34$^−$ cells (Lonza, Wakerfield) were cultured with rhS100A9 and a decrease in viable cells was again observed after treatment (50.7% viability in control cells versus 24.7% in rhS100A9 treated cells, FIG. 6I). These findings suggest that S100A9 has a direct apoptotic effect in human HSCs.

Figure 7A:
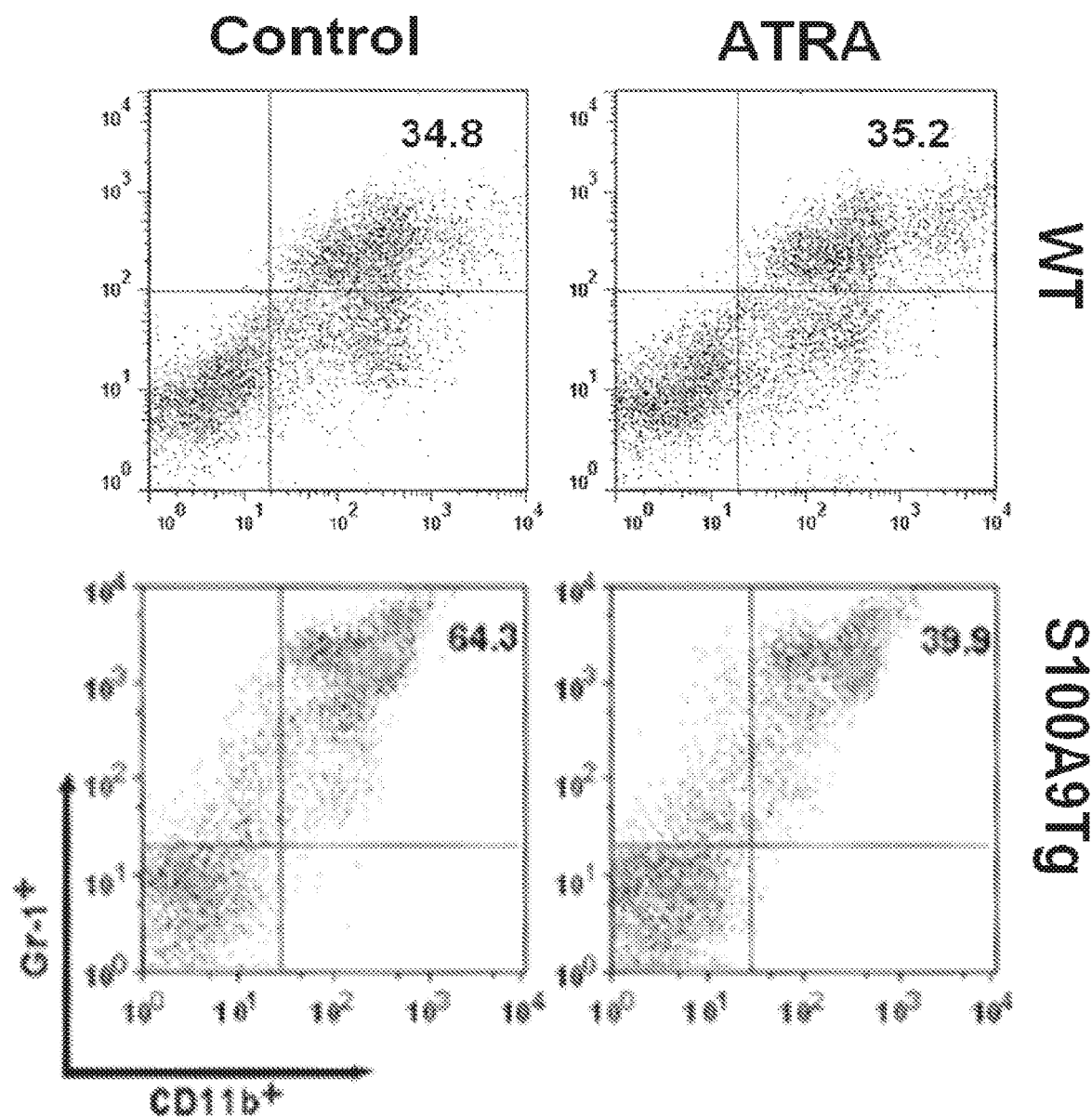
FIGS. 7A to 7I show targeting MDSC activation and signaling can improve suppressive BM microenvironment.
Figure 7B:
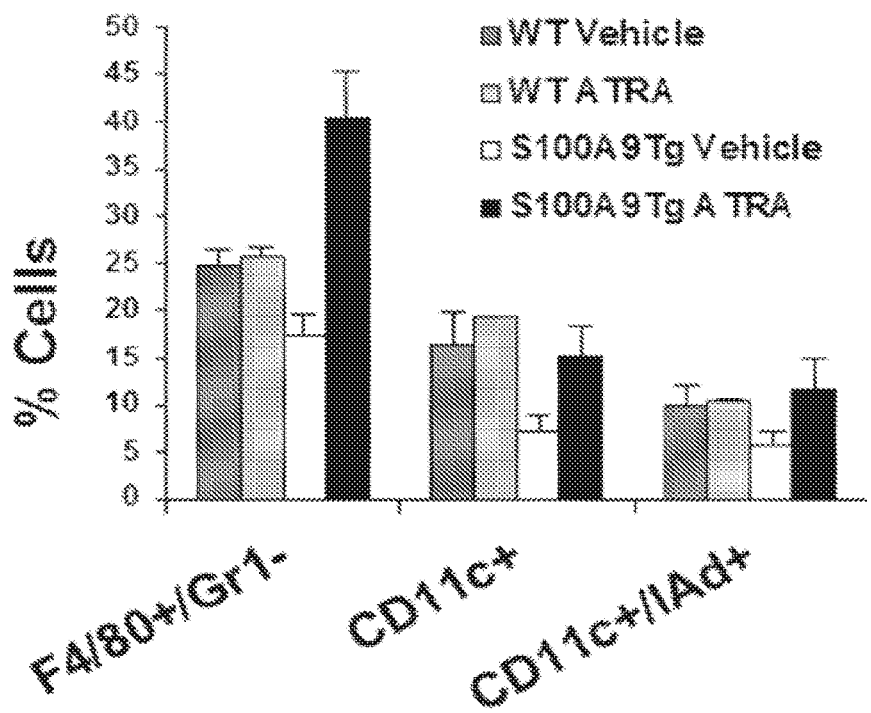
Figure 7C:
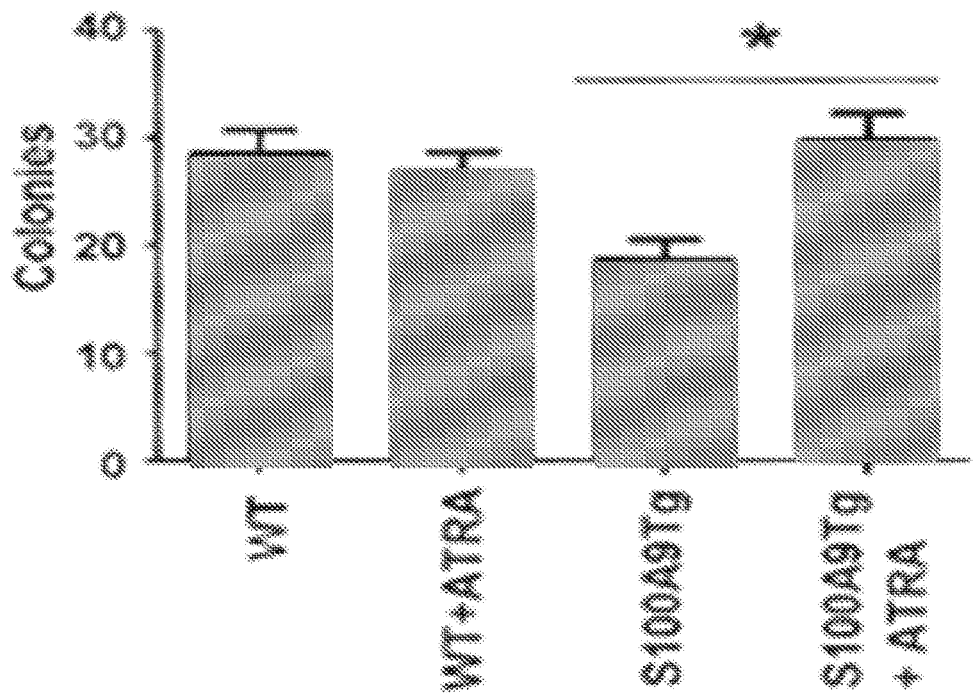
Figure 7D:
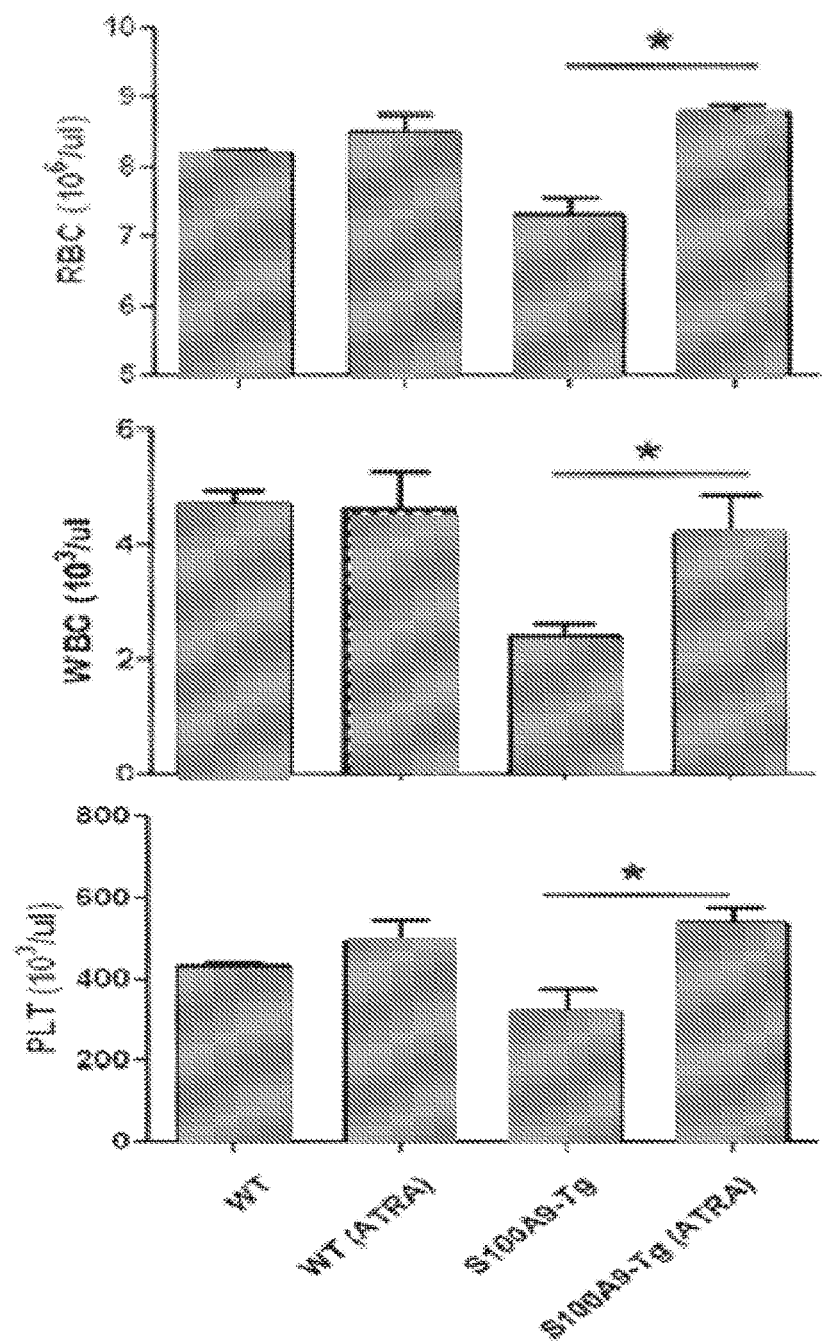

Forced maturation of MDSC restores hematopoiesis. To confirm the effector role of MDSC and investigate the potential benefit of targeted suppression of MDSC, S100A9Tg mice were treated with all-trans-retinoic acid (ATRA). ATRA induces MDSC differentiation into mature myeloid cells and neutralizes ROS production, thereby extinguishing MDSC through forced terminal differentiation (Nefedova, Y., et al. 2007. Cancer Res 67:11021-11028; Mirza, N., et al. 2006. Cancer Res 66:9299-9307). To this end, it was examined whether ATRA would induce MDSC differentiation in S100A9Tg mice and improve hematopoiesis. S100A9Tg and WT mice were treated with ATRA (250 µg/200 µl) or vehicle control orally for five consecutive days. Two days after completion of the treatment, ATRA reduced the total number of MDSC while numbers in WT mice remained at basal levels (FIG. 7A). Reductions in MDSC number in S100A9Tg mice were coupled to an increase in mature cells following ATRA treatment (FIG. 7B). Treatment of primary MDS BM specimens with ATRA also reduced in vitro MDSC accumulation. Importantly, BM progenitor cultures from ATRA-treated S100A9Tg mice showed significantly improved BFU-E recovery compared to vehicle-treated controls (FIG. 7C). Analysis of changes in peripheral blood counts showed that RBC, WBC and platelet counts significantly increased compared to vehicle treated controls (FIG. 7D), indicating that terminal differentiation of MDSCs can restore effective hematopoiesis.

Figure 7E:
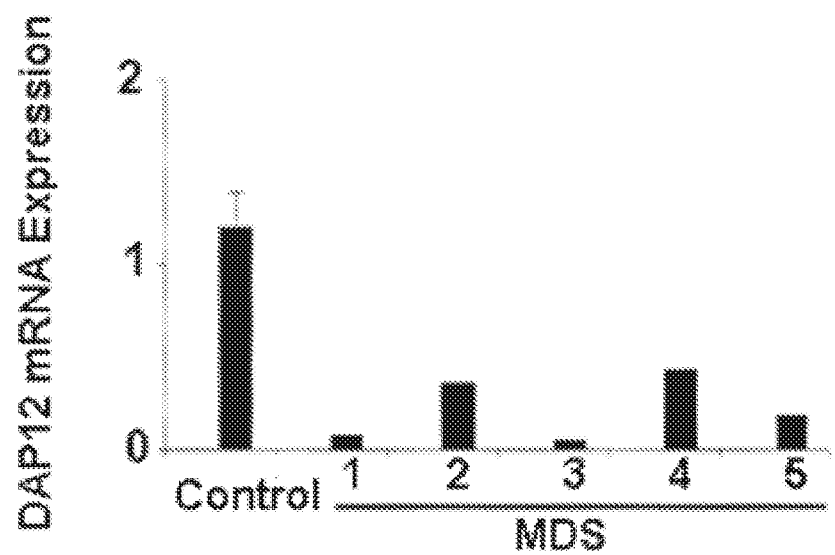
Figure 7F:
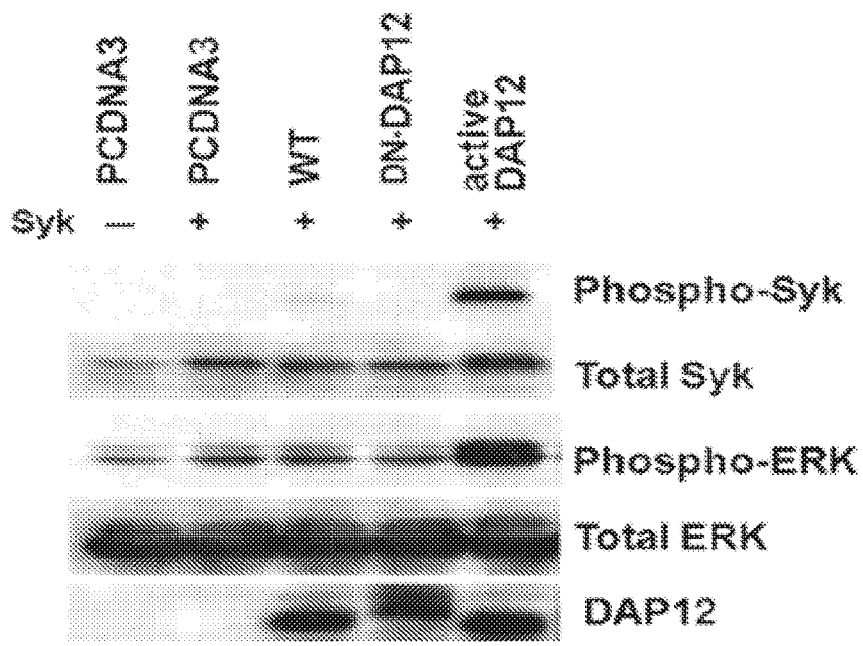
Figure 7G:
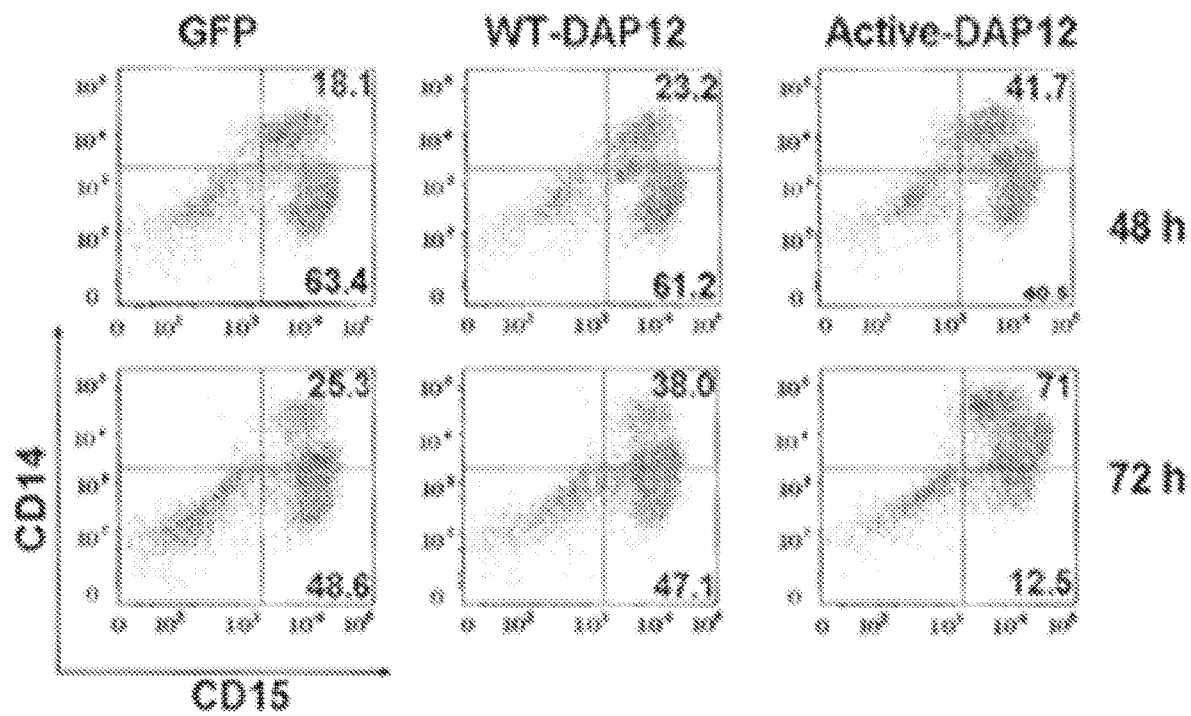
Figure 7H:
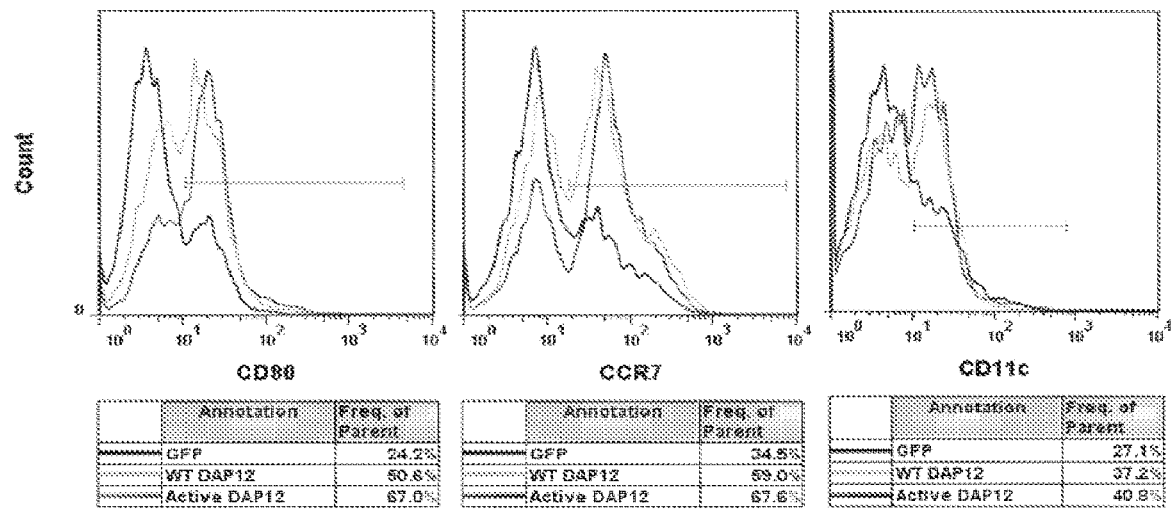
Figure 7I:
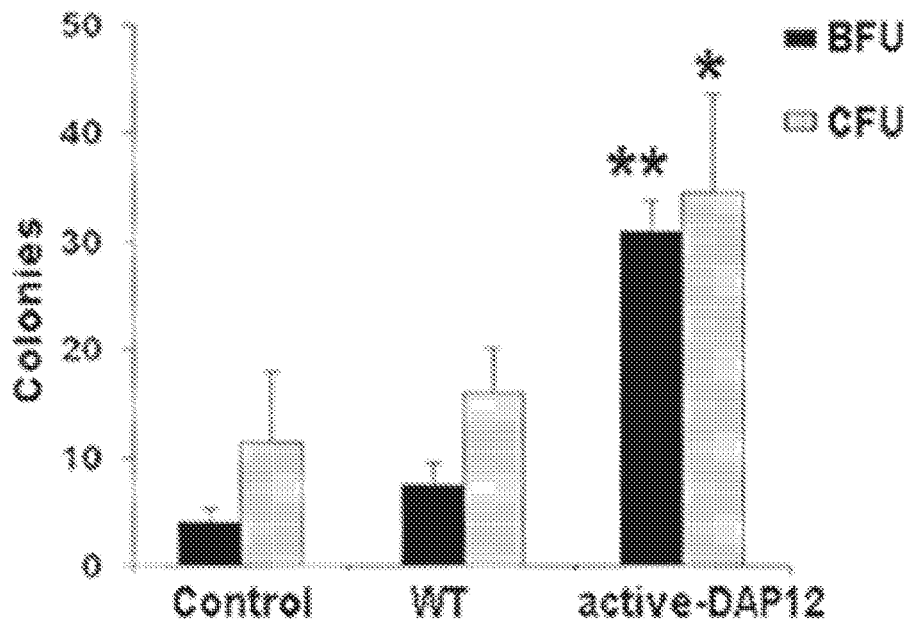
Figure 9:
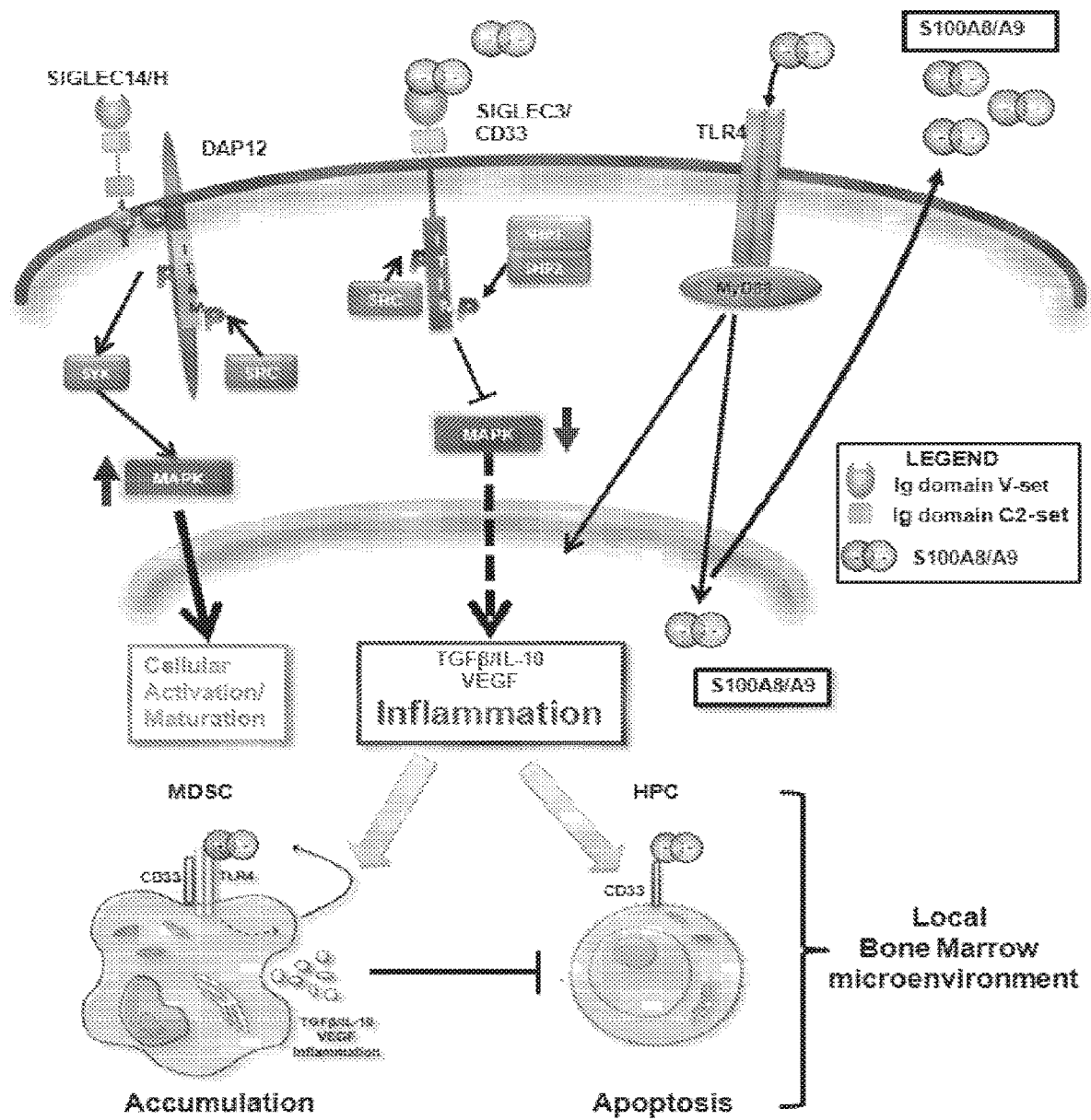
FIG. 9 is a model of CD33/Siglec 3-mediated signaling either through ITIM or ITAM motifs. CD33 has two cytosolic ITIM motifs. Src kinases phosphorylate tyrosine residues present in the ITIMS after CD33 cross-linking or upon interaction with its ligand(s). Phosphorylated ITIMs recruit and activate phosphatases (SHP1, SHP2, or SHIP-1), resulting in down regulation of MAPK and ultimately, cellular inhibition and the production of inhibitory cytokines. Activation of CD33 also induces S100A8 and S100A9 expression, which are secreted and act as heterodimers for CD33 or TLR4, and as such, mediates inflammation and MDSC activation. Siglecs that lack ITIMs possess charged amino acids in their trans-membrane domain, which allow association with DAP12, an ITAM-bearing activating adaptor. As is the case with ITIMs, Src kinases also phosphorylate tyrosine residues in the ITAM of DAP12. Syk kinase and ZAP70 are then recruited and perpetuate downstream cellular activation, differentiation, and/or maturation.
Figure 10:
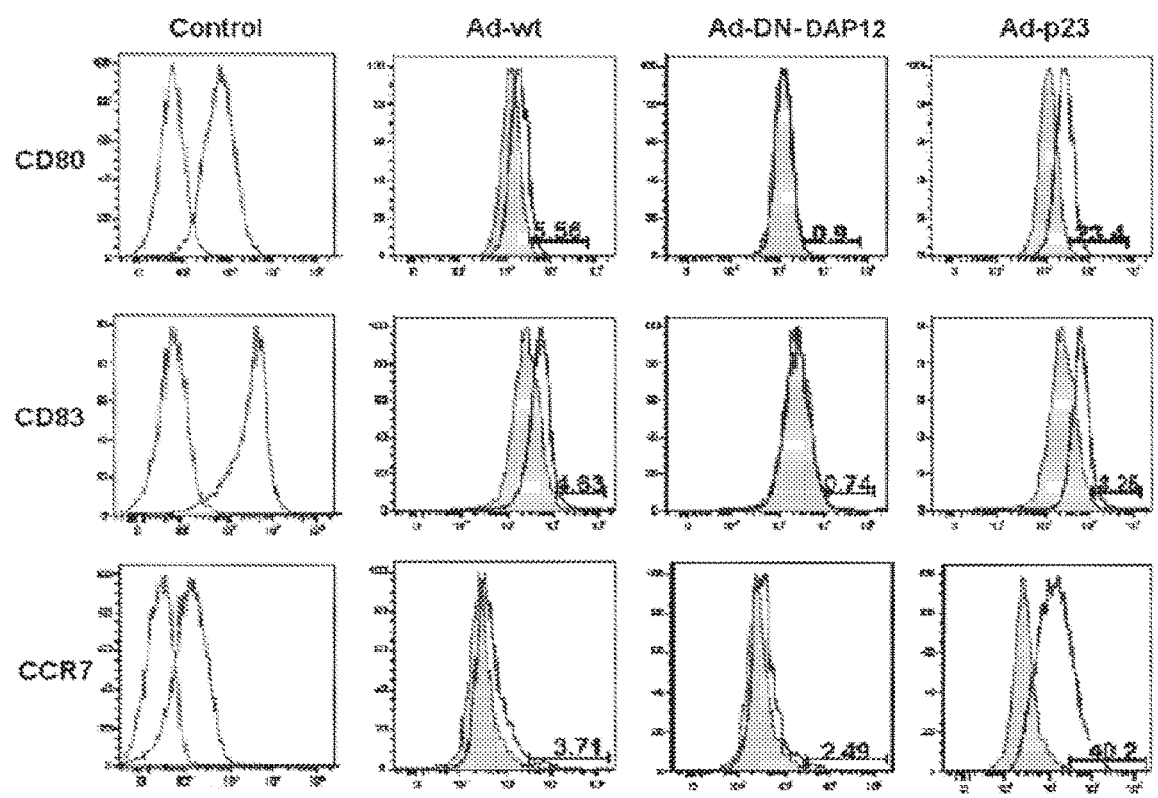
FIG. 10 shows t effect of active DAP12 on immature DC maturation. Primary DCs were prepared from healthy donors and infected with adenoviral vectors containing GFP alone, WI-DAP12, dnDAP12 and active DAP12 (Ad-P23) as indicated. The cells were cultured for 72 hrs before flow cytometric analysis using mature DC surface marker as indicated. Mock infected DC and Isotype IgG included in control group. Each experimental construct was compared to the empty-vector control (filled histograms), and infected cells were gated on GFP prior to analysis.
Figures 11A, 11B, 11C, 11D, 11E, 11F, 11G, 11H, 11I:
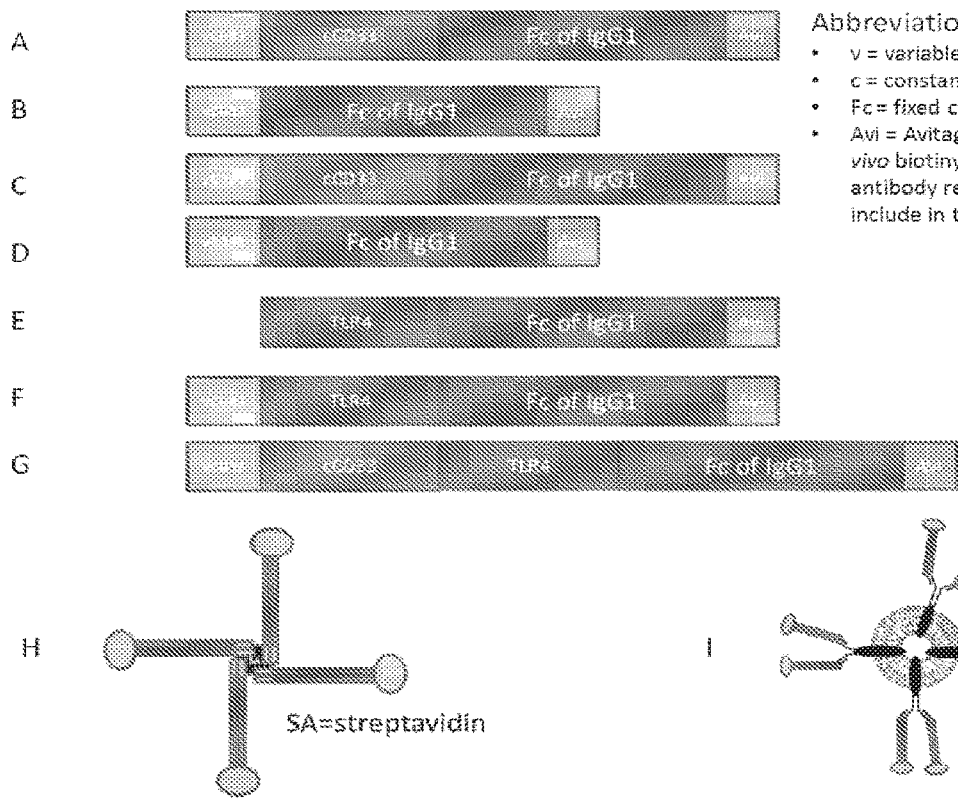
FIGS. 11A to 11G show a fusion protein contain the Fc portion of IgG, and a biotin acceptor peptide (e.g., AviTag™ sequence) for biotinylation by BirA or antibody recognition. The fusion protein in FIGS. 11A, 11C, and 11G contain the ectodomain of CD33. The fusion protein of 11B and 11D contains only the variable region of the ectodomain of CD33 ("vCD33"). The vCD33 region in FIGS. 11C and 11D contains single nucleotide polymorphisms ("SNPs") compared to the vCD33 in FIGS. 11A and 11B. The fusion protein depected in FIGS. 11E, 11F, and 11G contain the ectodomain of Toll like receptor 4 (TLR4). The fusion proteins in FIGS. 11F and 11G also contain the ectodomain of CD33 (FIG. 11G) or only the vCD33 region (FIG. 11F).
FIG. 11H shows a multimeric complex formed by the biotinylation of the AviTag™ sequence and the conjugation of these fusion proteins to a tetrameric streptavidin ("SA").
FIG. 11I shows a multimeric complex formed by the incorporation of antibodies that specifically bind AviTag™ into a liposome.

Investigations showed that MDSC employ CD33-associated ITIMs to inhibit their own cellular maturation (FIGS. 3N and O). However, ITIM signals can be over-ridden by stimulatory immunoreceptor tyrosine based activation motif (ITAM)-mediated signals (Lanier, L. L. 2005. Annu Rev Immunol 23:225-274; Ravetch, J. V., et al. 2000. Science 290:84-89). Some CD33-related receptors, such as certain Siglecs, lack ITIMs and instead function as activating receptors. Mouse Siglec-H and human Siglec-14 have been shown to interact with DAP12 (Blasius, A. L., et al. 2006. Blood 107:2474-2476; Blasius, A. L., et al. 2006. Trends Immunol 27:255-260; Angata, T., et al. 2006. Faseb J 20:1964-1973; Lanier, L. L., et al, 1998. Nature 391:703-707), an ITAM-containing adaptor that can promote myeloid cell maturation (FIG. 9) and inhibit TLR-4 activation (Turnbull, I. R., et al. 2007. Nat Rev Immunol 7:155-161). Rhe DAP12 gene expression of purified MDS-MDSC (n=5) was compared to age-matched healthy donor MDSC (n=5). DAP12 mRNA was significantly lower in MDS-MDSC in all specimens tested (FIG. 7E). It was reasoned that over-riding CD33-ITIM signaling via DAP12 would induce the differentiation of these immature myeloid cells and improve hematopoiesis. To test this, a constitutively active form of DAP12, named P23, was created and AD293 cells transfected with either GFP, WT-DAP12, or active-DAP12 P23 viral vectors. The results show that P23 binds Syk kinase and activates downstream signaling in transduced AD293 cells without external stimulation (FIG. 7F). Furthermore, P23 promotes primary human DC maturation as demonstrated by up-regulation of CD80, CD83, and CCR7 antigens (FIG. 10) (Blasius, A. L., et al. 2006. Blood 107:2474-2476; Blasius, A. L., et al. 2006. Trends Immunol 27:255-260). Based on these findings, it is possible that P23 could induce the maturation of MDS-MDSC and thereby prevent or disrupt hematopoietic suppression. To test this, expression of the human monocytic and granulocytic surface markers CD14 and CD15 were analyzed after transfection (Araki. H., et al. 2004. Blood 103:2973-2980) and results showed that while WT-DAP12 transfection alone was sufficient to induce up-regulation of CD14 and CD15, P23 transfection induced even greater expression of both maturation markers (FIG. 7G). Moreover, P23 promoted the maturation of primary MDS-MDSC as demonstrated by up-regulation of CD80, CD83, and CCR7 maturation markers (FIG. 7H). Lastly, to test whether DAP12-mediated MDSC maturation relieved suppression of erythropoiesis, MDS-MDSC were purified from seven MDS patients and infected with control, WT-DAP12 or P23 lentiviral constructs. To assess the suppressive function of the mature MDS-MDSCs on hematopoiesis, colony forming capacity was assessed after culture of infected cells with autologous, MDSC-depleted BM cells. P23-infected MDS-MDSC co-cultures yielded significantly higher colony numbers than control viral vector or WT-DAP12-infected MDS-MDSC co-cultures (FIG. 7I). These findings indicate that DAP12 overrides CD33-associated ITIM signaling to stimulate MDSC maturation, and reverse the suppressive effects on HPC colony forming capacity.

Discussion

Inflammatory stimuli within the BM microenvironment are recognized as important biological signals stimulating progenitor cell proliferation and apoptosis in MDS. A recent population-based study extended this further by demonstrating a strong linkage between chronic immune stimulation and MDS predisposition (Kristinsson, S. Y., et al. 2011. J Clin Oncol 29:2897-2903). Definitive evidence that niche intrinsic abnormalities per se can alone account for development of MDS in a cell non-autonomous fashion are limited. Raaijmakers and colleagues showed that selective osteo-progenitor dysfunction caused by deletion of Dicer1 in the mesenchymal component of the BM microenvironment was sufficient to perturb hematopoiesis and lead to development of myeloid dysplasia, followed by secondary emergence of myeloid-restricted genetic abnormalities (Raaijmakers, M. H., et al. 2010. Nature 464:852-857).

The disclosed studies show that Lin⁻HLA-DR⁻CD33⁺ MDSC accumulate in the BM of MDS patients, derive from a population that is distinct from the neoplastic clone, and serve as cellular effectors that suppress hematopoiesis, promote T cell tolerance and serve as a key source of myelo-suppressive and inflammatory molecules such as IL-10, TGF-β, NO, and arginase. Using multiple biological and biochemical approaches, it was shown that S100A9, also known as migration inhibitory factor-related protein 14 (MRP-14) or calgranulin-B, can serve as art endogenous native ligand for CD33/Siglec 3. Furthermore, forced expansion of MDSC by over-expression of the S100A9 in transgenic mice initiates development of hematologic features that phenocopy human MDS, specifically progressive age-dependent ineffective and dysplastic hematopoiesis. These findings indicate that expansion of a single cellular constituent of the BM microenvironment is sufficient to foster neoplastic change in heterologous myeloid progenitors through niche-conducive oncogenesis. The time dependent accumulation of MDSC in the transgenic mouse model parallels recent human findings that MDSCs expand with age accompanied by rising serum levels of proinflammatory cytokines (e.g., TNF-α, IL-6, and IL-1β), providing evidence that such senescence dependent changes driving MDSC expansion may play an important role in the age dependent pathogenesis of MDS (Verschoor C P, et al. 2013. J Leukoc Biol 93(4):633-7). Importantly, the LIN⁻HLA-DR⁻CD33⁻ phenotype did not alone confer suppressor cell function, as evidenced by lack of LIN⁻HLA-DR⁻CD33⁻ MDSC suppression from age-matched healthy donors or non-MDS cancer patients. The disclosed studies demonstrate the necessity for activation of innate immune signaling and generation of pro-inflammatory molecules, such as S100A9, for the induction of MDS-MDSC-mediated suppressor function. Furthermore, the disclosed finding that primary human MDS-MDSC lack molecular genetic abnormalities intrinsic to the malignant clone indicate that MDSC derive from non-neoplastic HSC, and that MDSC activation and expansion likely precedes emergence of genetically distinct MDS clones.

CD33, a Siglec receptor expressed by many immune cells including MDSC, is shown herein to be markedly over-expressed by MDS-MDSC, and this receptor is shown to control the suppressive functions of MDS-MDSC through disruption of ITIM-mediated signaling. Additionally, the disclosed findings that rhS100A9 directly triggers apoptosis in human HPCs, indicates that this ligand exerts dual roles in the promotion of ineffective hematopoiesis that involve both cellular (MDSC) and humoral mechanisms (CD33, TLR4). Moreover, cellular response to CTD33 ligand engagement appears cell type specific, i.e., apoptosis in HPC versus activation and proliferation in MDSC. Compensatory regeneration within the myeloid compartment could account for the increased proliferative index observed in MDS (Raza et. al. 1995. Blood 86(1):268-276) and preferential myeloid skewing that occurs with age. Over-expression of CD33 may therefore impair maturation signals from ITAM associated receptors that is critical to expansion of immature MDSC (FIGS. 7G and H). Consistent with this, shRNA silencing of CD33 reduced myelosuppressive cytokine elaboration, and importantly, restored hematopoietic progenitor colony forming capacity. Moreover, constitutively active DAP12 signaling was sufficient to override CD33-ITIM inhibition and induce MDSC differentiation, which restored erythropoiesis upon active-DAP12 transfection into MDS-MDSC. More importantly, DAP12 activation can inhibit TLR-mediated signaling pathways, which may also play a role in the inflammation-mediated BM suppression (Turnbull, I. R., et al, 2007. Nat Rev Immunol 7:155-161; Hamennan, J. A., et al, 2006. J Immunol 177:2051-2055).

Mounting evidence implicates activation of innate immune signaling in the pathogenesis and biologic features of human MDS (Hofmann, W. K., et al. 2002. Blood 100:3553-3560; Gondck, L. P., et al. 2008. Blood 111:1534-1542; Starczynowski, D. T., et al. 2008. Blood 112:3412-3424). In del(5q) MDS, allelic deletion of miR-145 and miR-146a results in de-repression of the respective targets, TIRAP and TRAF6. Of particular importance, Starcznowski and colleagues showed that knockdown of these specific miRs or over-expression of TRAF6 in murine HSPC recapitulated hematologic features of del(5q) MDS in a transplant model through both cell-autonomous and non-autonomous mechanisms involving interleukin-6 (Starczynowski, D. T., et al, 2010 Nat Med 16:49-58; Starczynowski, D. T., et al. 2010, Hernatol Oncol Clin North Am 24:343-359). The disclosed studies show that the heterodimeric DAMP S100A8/S100A9, specifically released at BM inflammatory sites, is not only aberrantly expressed in MDS but serves as a native ligand for CD33. This finding provides evidence that S100 proteins contribute directly to MDS pathogenesis through microenvironment-directed, cell non-autonomous mechanisms involving MDSC (Ehrchen, J. M., et al. 2009, J Leukoc Biol 86:557-566; Viemann, D., et al. 2007. Blood 109:2453-2460). Moreover, TLR activation suppresses osteoblast differentiation, while instructing myeloid commitment in HSC (Bandow, K., et al. 2010. Biochem Biophys Res Commun 402:755-761; De Luca, K., et at 2009, Leukemia 23:2063-2074). Prolonged activation of innate immune signaling with age, therefore, may disrupt the BM endosteal niche supporting maintenance of hematopoietic stein cells, and favor translocation of myeloid progenitors to an angiogenic niche characteristic of MDS (Bellamy, W. T., et al. 2001. Blood 97:1427-1434). This is supported by the disclosed findings of age dependent development of cytopenias with emergence of dysplastic cytological features in the S100A9Tg mice. More importantly, the competitive transplant experiments showed that admixture of S100A9Tg with WT donor HSCs delays, albeit with time still impairs hematopoiesis.

The disclosed findings support a model for MDS pathogenesis in which sustained activation of innate immune signaling in the BM microenvironment creates a permissive inflammatory milieu that is sufficient for development of myelodysplasia. Cell autonomous neoplastic hematopoietic progenitors may emerge following acquisition of secondary genetic abnormalities in the myeloid compartment. S100A9Tg mice simulate human MDS and can serve as an in vivo model to study MDS pathogenesis and development of novel therapeutics. Nevertheless, therapeutic interventions that promote MDSC maturation may have remitting potential when applied early in the disease course.

Example 2

Active caspase-1 (Table 3) and IL-1β generation (Table 4) were assessed in four populations: stem cells (CD34+CD38−), progenitors (CD34+CD38+), crythroids (CD71+), and myeloid cells (CD33+). Mean fluorescent intensity (MEI) values are shown in Table 3.

TABLE 3

Treatment with CD33-IgG decreases active caspase-1 generation in an MDS specimen.

| Ancestry | Stem Cells LIVE/CD34+/STEM | Progenitors LIVE/CD34+/PROGENITORS | Erythroids LIVE/CD71+ | Myeloids LIVE/CD33+ |
|---|---|---|---|---|
| Subset | Geom. Mean | Geom. Mean | Geom. Mean | Geom. Mean |
| Value Type | <FITC-A> | <FITC-A> | <FITC-A> | <FITC-A> |
| For | FAM FLICA | FAM FLICA | FAM FLICA | FAM FLICA |
| UNSTAINED | 731 | 5760 | 189 | 3908 |
| PLASMA ONLY | 7062 | 61966 | 4170 | 44708 |
| 1 µg IgG | 4316 | 38250 | 2836 | 37161 |
| 0.1 µg CD33-IgG | 5232 | 43019 | 3339 | 40221 |
| 0.5 µg CD33-lgG | 5015 | 48556 | 3135 | 41516 |
| 1 µg CD33-lgG | 3444 | 24089 | 2247 | 19533 |

TABLE 4

Treatment with CD33-IgG decreases IL-1β generation in an MDS specimen.

| Ancestry | LIVE/CD34+/STEM | LIVE/CD34+/PROGENITORS | LIVE/CD71+ | LIVE/CD33+ |
|---|---|---|---|---|
| Subset | Geom. Mean | Geom. Mean | Geom. Mean | Geom. Mean |
| Value Type | <PE-A> | <PE-A> | <PE-A> | <PE-A> |
| For | IL-1b-PE | IL-1b-PE | IL-1b-PE | IL-1b-PE |
| UNSTAINED | 1457 | 25484 | 45.5 | 9979 |
| PLASMA ONLY | 201 | 9682 | 56.6 | 8884 |
| 1 µg IgG | 126 | 6667 | 15.5 | 8051 |
| 0.1 µg CD33-IgG | 191 | 6380 | 48.2 | 8472 |
| 0.5 µg CD33-lgG | 151 | 10343 | 24.4 | 9073 |
| 1 µg CD33-lgG | 119 | 3092 | 12.6 | 3766 |

Figure 12A:
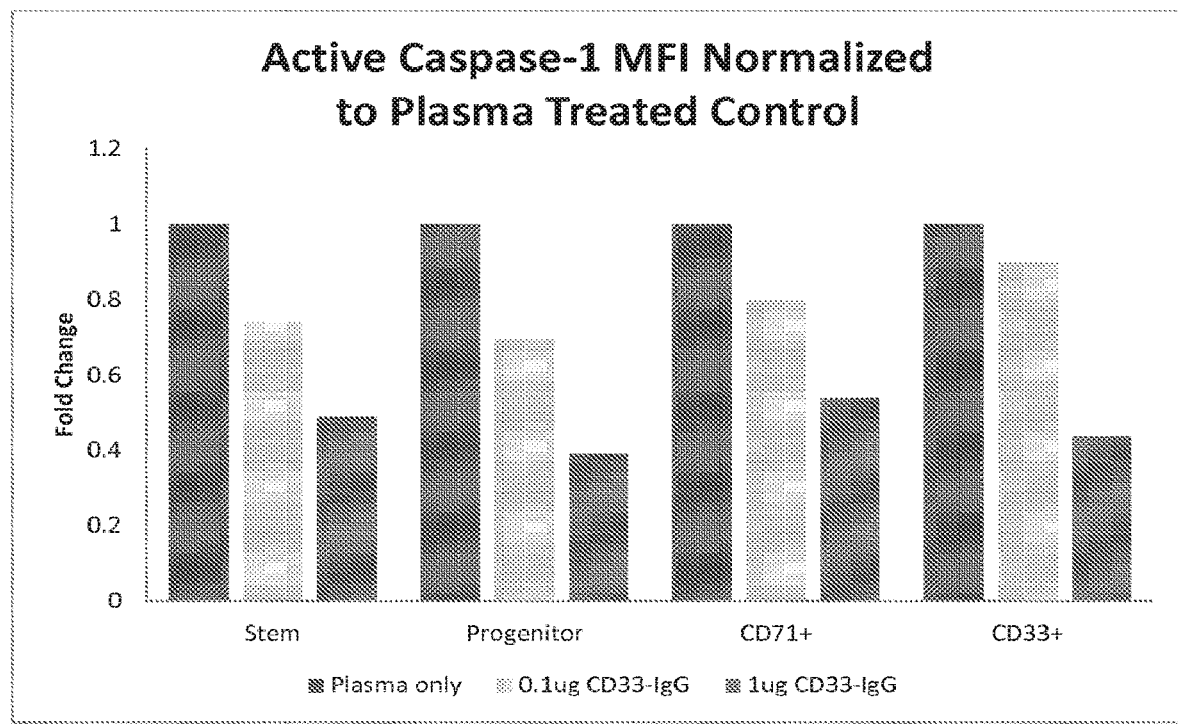
FIGS. 12A and 12B show fold change of active caspase-1 and IL-1β generation normalized to plasma treated control in four cell populations. Active caspase-1 and IL-1β generation were assessed in four populations by flow cytometry after treatment with CD33-IgG: stem cells (CD34+CD38−), progenitors (CD34+CD38+), erythroids (CD71+), and myeloid cells (CD33+). Fold change of active caspase-1 MFI (FIG. 12A) and IL-1β generation (FIG. 12B).
Figure 12B:
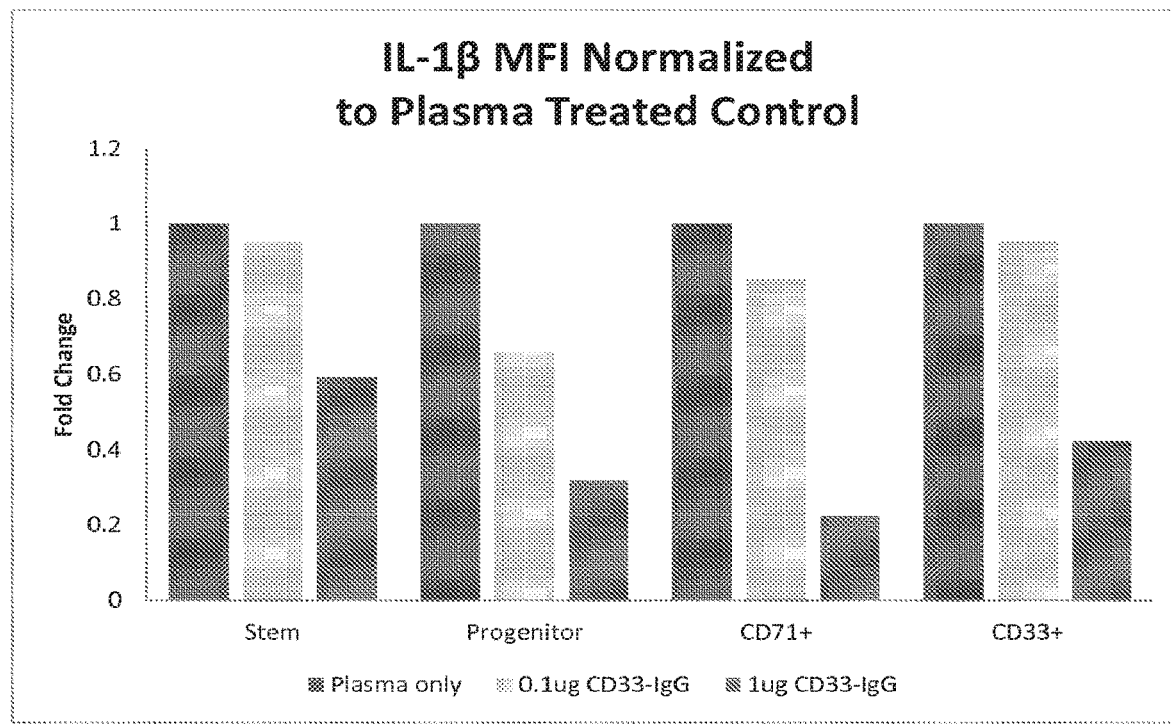

As shown in FIG. 12, fold change of active caspase-1 and IL-1β generation normalized to plasma treated control in four cell populations. Active caspase-1 and IL-1β generation were assessed in four populations by flow cytometry after treatment with CD33-IgG: stem cells (CD34+CD38−), progenitors (CD34+CD38+), erythroids (CD71+), and myeloid cells (CD33+). Fold change of active caspase-1 MFI (FIG. 12A) IL-1β generation (FIG. 12B).

Figure 13A:
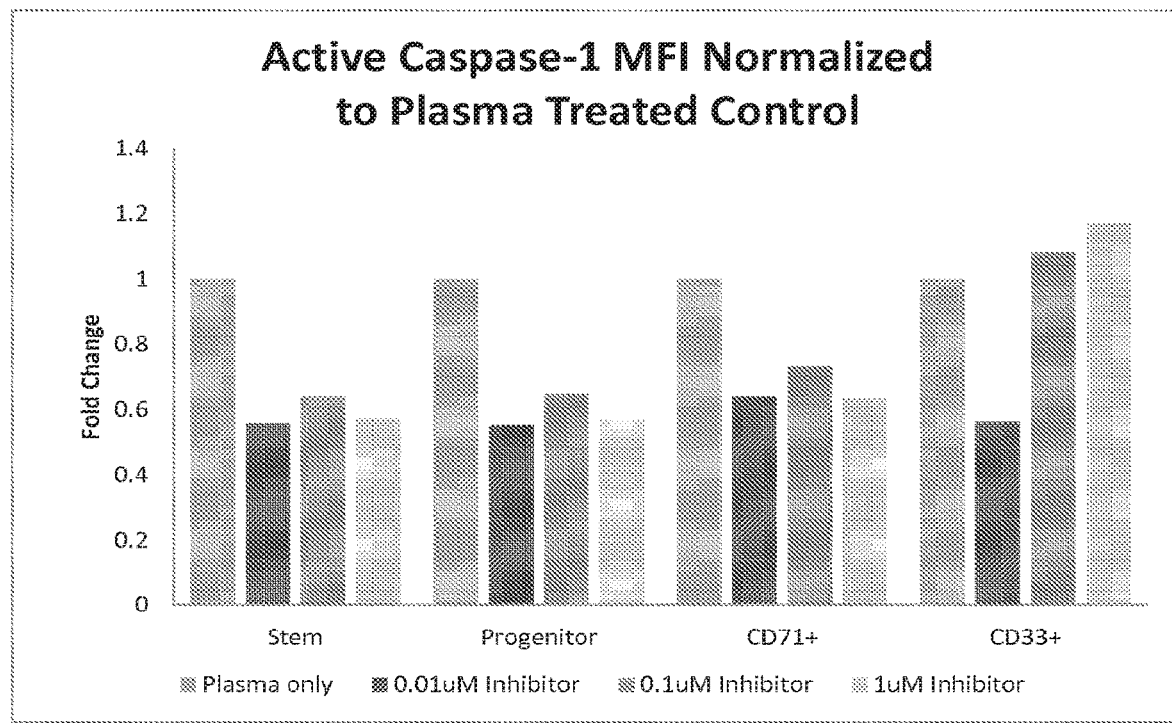
FIGS. 13A and 13B show fold change of active caspase-1 and IL-1β generation normalized to plasma treated control in four cell populations. Active caspase-1 and IL-β generation were assessed in four populations by flow cytometry after treatment with a related pathway inhibitor: stem cells (CD34+CD38−), progenitors (CD34+CD38+), erythroids (CD71+), and myeloid cells (CD33+). Fold change of active caspase-1 (FIG. 13A) and IL-1β generation (FIG. 13B).
Figure 13B:
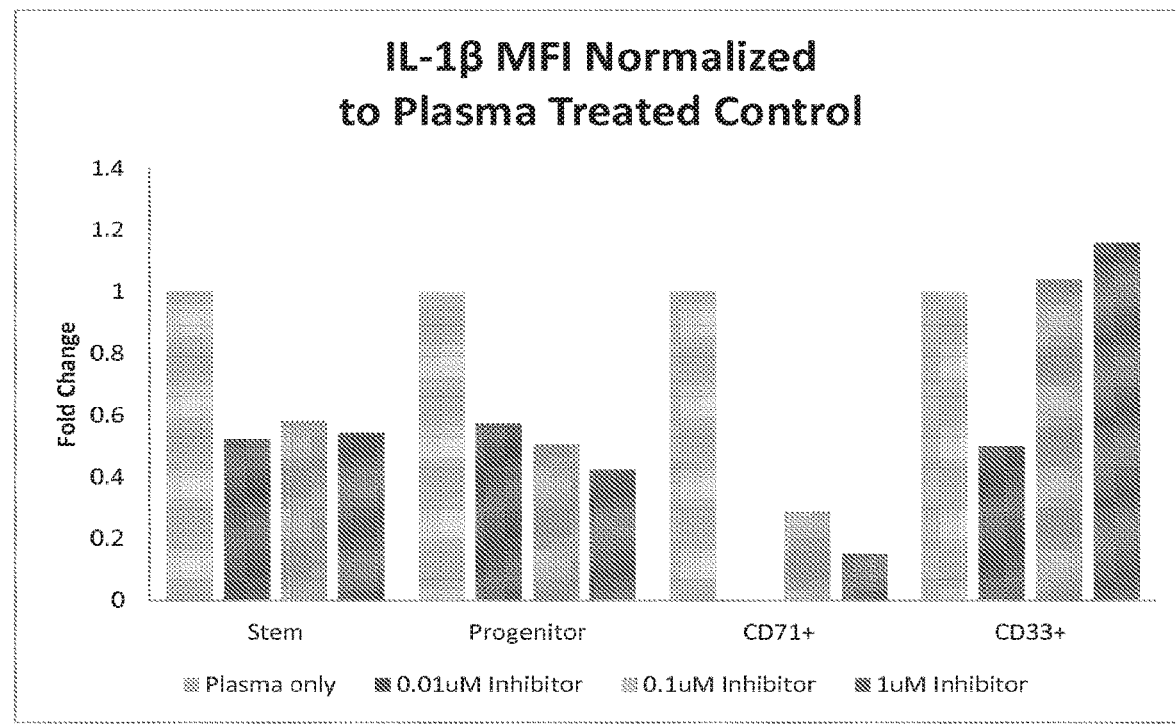

As shown in FIG. 13, fold change of active caspase-1 and IL-1β generation normalized to plasma treated control in four cell populations. Active caspase-1 and IL-1β generation were assessed in four populations by flow cytometry after treatment with a related pathway inhibitor: stem cells (CD34+CD38−), progenitors (CD34+CD38+), erythroids (CD71+), and myeloid cells (CD33+). Fold change of active caspase-1 MFI (FIG. 13A) and IL-1β generation (FIG. 13B).

Active caspase-1 and IL-1β generation were assessed in four populations: stem cells (CD34+CD38−), progenitors (CD34+CD38+), erythroids (CD71+), and myeloid cells (CD33+). Mean fluorescent intensity (MFI) values are found in the Tables 3 and 4.

Figure 14A:
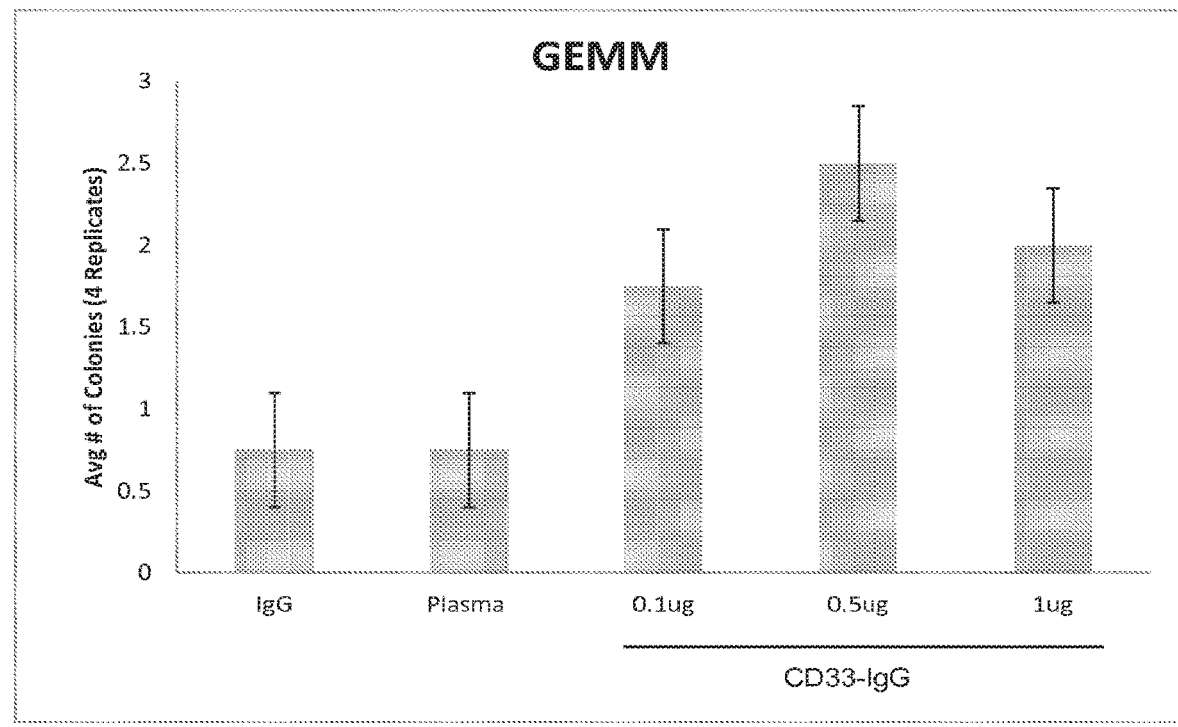
FIGS. 14A to 14C show neutralization of plasma S100A9 by CD33 Chimera trap enhances colony forming capacity in MDS patient specimens.
Figure 14B:
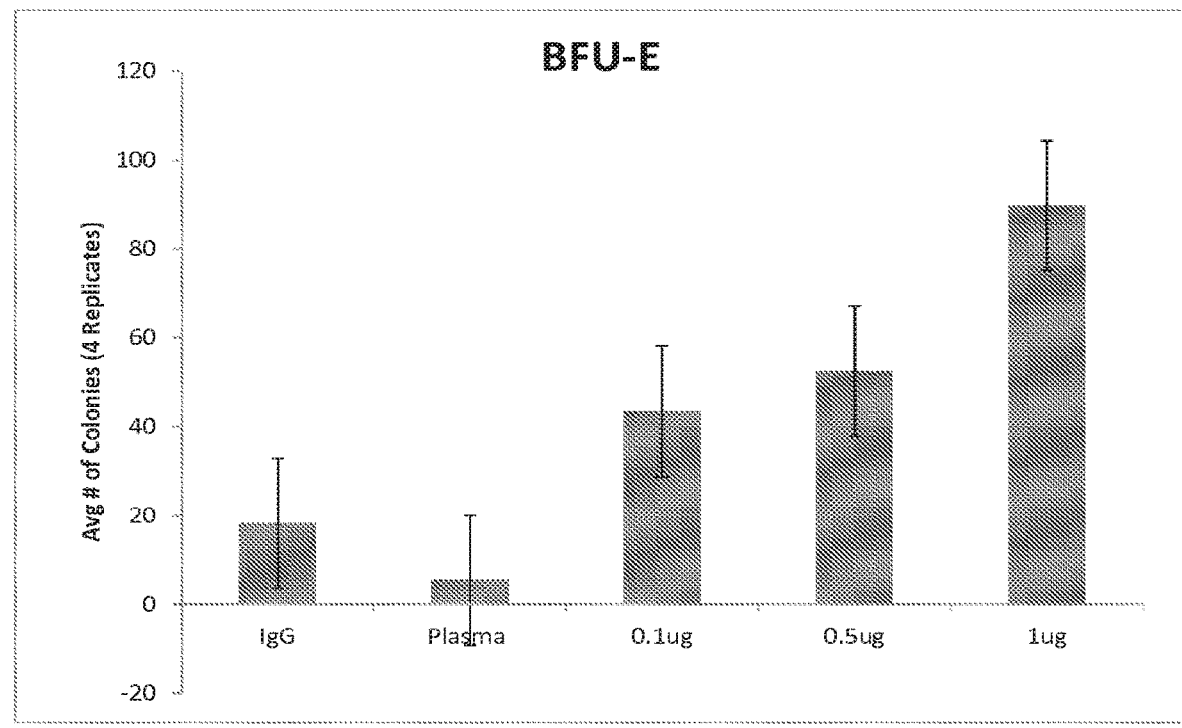
Figure 14C:
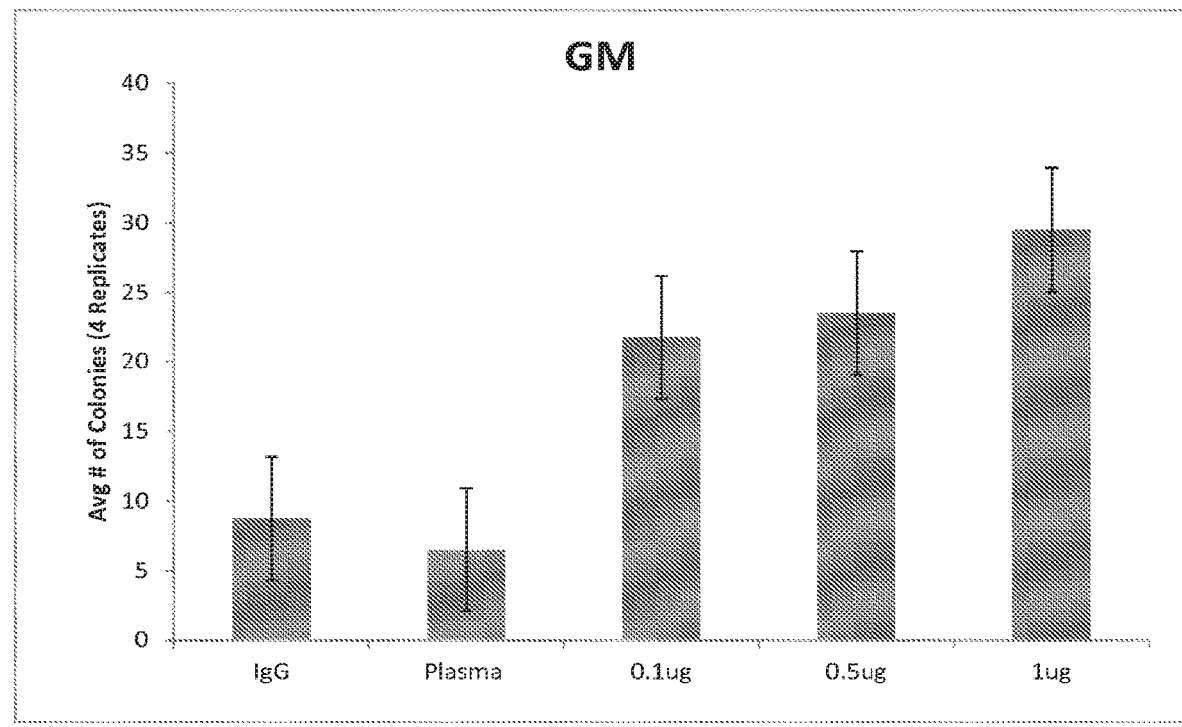
Figure 15A:
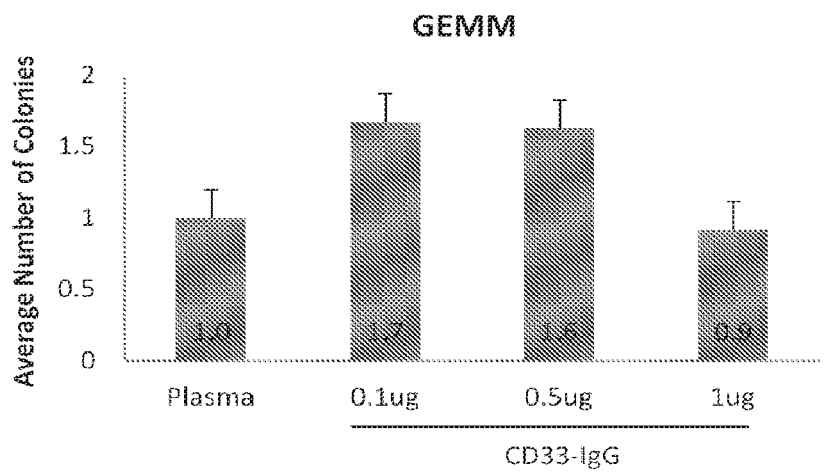
FIGS. 15A to 15C show change in colony forming capacity in four LR-MDS specimens treated with CD33 chimera. BM-MNC from each patient were incubated with autologous BM plasma and increasing concentrations of CD33-IgG, and were plated in four replicates per treatment condition in methylcellulose. Colonies were counted fourteen days after plating, and were averaged for each patient. The increase in CFC is represented as the fold change normalized to plasma-incubated control for GEMM (FIG. 15A), erythroid (FIG. 15B), and GM (FIG. 15C) colonies, respectively.
Figure 15B:
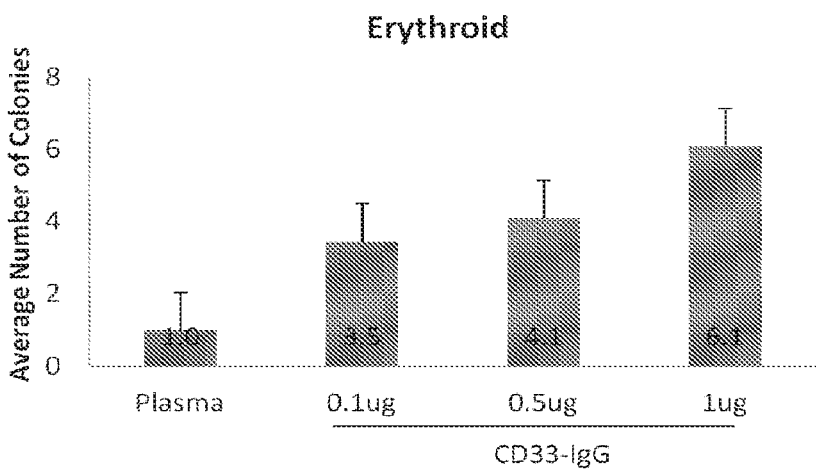
Figure 15C:
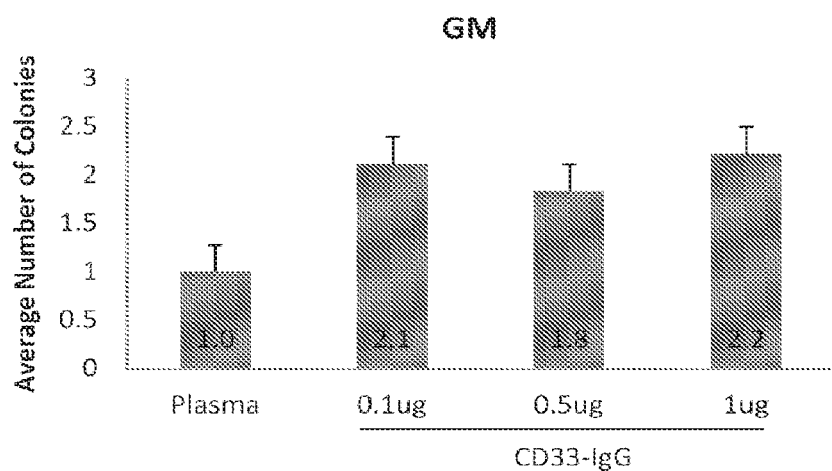
Figure 16A:
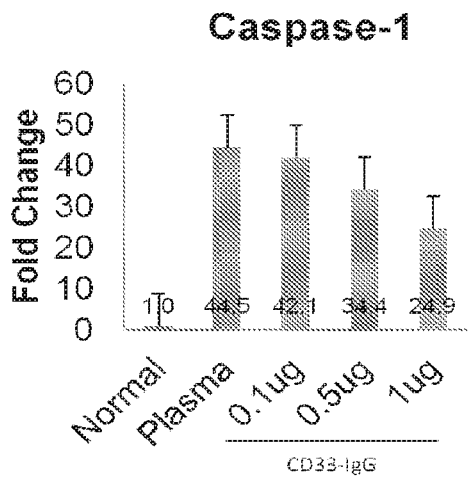
FIGS. 16A to 16E show CD33-chimera trap suppresses pyroptosis-related gene expression in MDS BM-MNC. BM-MNC were isolated from five low risk MDS patients and incubated with autologous BM plasma and increasing concentrations of the CD33 chimera. BM-MNC isolated from five normal donors were used for comparison. RNA was isolated and qPCR was carried out on pyroptosis-related genes Capsapse-1 (FIG. 16A), IL-1β (FIG. 16B), NLRP1 (FIG. 16C), NLRP3 (FIG. 16D), and IL-18 (FIG. 16E). Gene expression is represented as the fold change normalized to the normal donors.
Figure 16B:
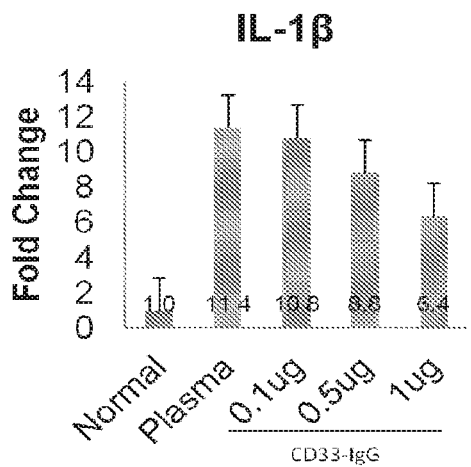
Figure 16C:
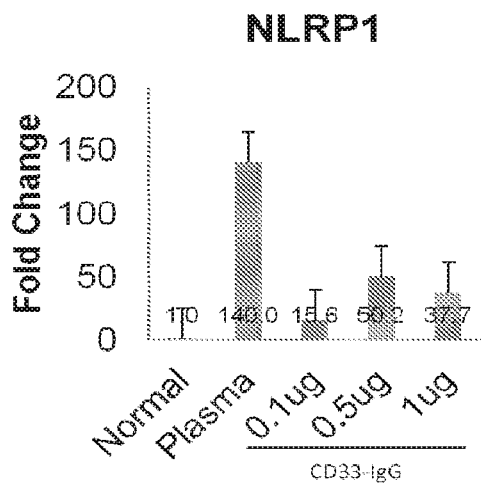
Figure 16D:
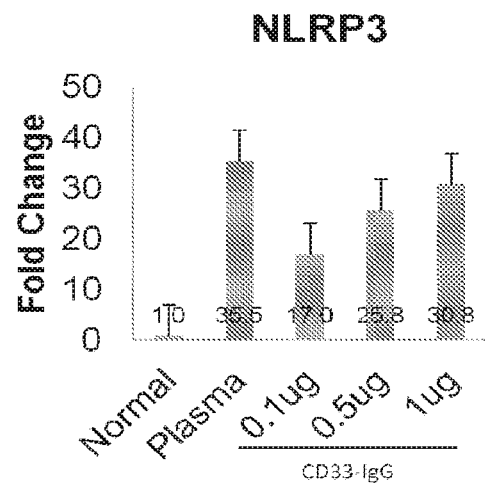
Figure 16E:
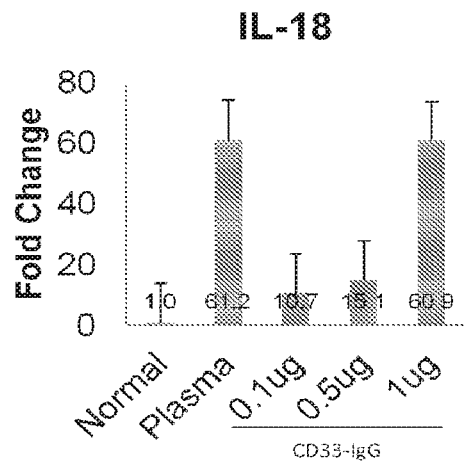

As shown in FIG. 14, neutralization of plasma S100A9 by CD33 Chimera trap enhances colony forming capacity in MDS patient specimens. FIGS. 14A to 14C show erythroid burst-forming units (BFU-E) (FIG. 14B), multipotential colony forming units (CFU-GEMM) (FIG. 14A), and granulocyte/macrophage colony forming units (CFU-GM) (FIG. 14C) in MDS patient specimens treated with IgG, plasma, or 0.1, 0.5, or 1.0 μg of CD33-IgG chimeric trap.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than rout experimentation, many equivalents to the specific embodiments of the invention described herein. Such equivalents are intended to be encompassed by the following claims.

---

What is claimed is:

1. A recombinant fusion protein, comprising:
(a) at least two S100A9-binding moieties selected from the group consisting of an extracellular domain of human CD33, an extracellular domain of toll like receptor 4 (TLR4), and an extracellular domain of Receptor for Advanced Glycation End Products (RAGE); wherein at least one of the at least two S100A9-binding moieties comprises the extracellular domain of human CD33, and wherein the extracellular domain of human CD33 comprises the variable region; and
(b) an immunoglobulin Fc region,
wherein the extracellular domain of human CD33 comprises the amino acid sequence SEQ ID NO:1-4, or an amino acid sequence having at least 90% identity to SEQ ID NO:1-4,
wherein the extracellular domain of TLR4 comprises the amino acid sequence SEQ ID NO:5, or an amino acid sequence having at least 90% identity to SEQ ID NO:5, and
wherein the extracellular domain of RAGE comprises the amino acid sequence SEQ ID NO:6, or an amino acid sequence having at least 90% identity to SEQ ID NO:6.

2. The fusion protein of claim 1, comprising a formula selected from the group consisting of:

eCD33-eTLR4-Fc, eCD33-eRAGE-Fc, eCD33-eTLR4-eRAGE-Fc, eCD33-eRAGE-eTLR4-Fc, eTLR4-eCD33-eRAGE-Fc, eRAGE-eCD33-eTLR4-Fc, eTLR4-eRAGE-eCD33-Fc, and eRAGE-eTLR4-eCD33-Fc, wherein "eCD33" comprises the extracellular domain of human CD33,
wherein "eTLR4" comprises the extracellular domain of TLR4,
wherein "eRAGE" comprises the extracellular domain of RAGE,
wherein "Fc" comprises the immunoglobulin Fc region, and
wherein "-" consists of a peptide linker or a peptide bond.

3. The fusion protein of claim 1, further comprising a biotin acceptor peptide that is biotinylated with biotin ligase (BirA) in the presence of biotin and ATP.

4. The fusion protein of claim 3, comprising a formula selected from the group consisting of:

eCD33-eTLR4-Fc-Avi, eCD33-eRAGE-Fc-Avi, eCD33-eTLR4-eRAGE-Fc-Avi, eCD33-eRAGE-eTLR4-Fc-Avi, eTLR4-eCD33-eRAGE-Fc-Avi, eRAGE-eCD33-eTLR4-Fc-Avi, eTLR4-eRAGE-eCD33-Fc-Avi, and eRAGE-eTLR4-eCD33-Fc-Avi wherein "eCD33" comprises the extracellular domain of human CD33,
wherein "eTLR4" comprises the extracellular domain of TLR4,
wherein "eRAGE" comprises the extracellular domain of RAGE,
wherein "Fc" comprises the immunoglobulin Fc region,
wherein "Avi" comprises a biotin acceptor peptide that can be biotinylated with biotin ligase (BirA) in the presence of biotin and ATP, and
wherein "-" consists of a peptide linker or a peptide bond.

5. The fusion protein of claim 3, wherein the biotin acceptor peptide comprises the amino acid sequence SEQ ID NO:7, or an amino acid sequence having at least 90% identity to SEQ ID NO:7.

6. The fusion protein of claim 1, wherein the extracellular domain of human CD33 comprises the amino acid sequence SEQ ID NO:1, or an amino acid sequence having at least 90% identity to SEQ ID NO:1.

7. The fusion protein of claim 6, wherein the extracellular domain of human CD33 comprises the amino acid sequence SEQ ID NO:2.

8. The fusion protein of claim 1, wherein the variable region of human CD33 comprises the amino acid sequence SEQ ID NO:3, or an amino acid sequence having at least 90% identity to SEQ ID NO:3.

9. The fusion protein of claim 8, wherein the variable region of human CD33 comprises the amino acid sequence SEQ ID NO:4.

10. A multimeric complex comprising two or more fusion proteins of claim 1 conjugated to a core molecule or particle.

11. The multimeric complex of claim 10, wherein the core molecule is streptavidin, wherein the two or more fusion proteins are biotinylated.

12. The multimeric complex of claim 10, wherein the core molecule is a liposome comprising antibodies that specifically bind the two or more fusion proteins.

13. The multimeric complex of claim 12, wherein the antibodies specifically bind the biotin acceptor peptide.

14. The multimeric complex of claim 10, comprising from 2 to 5 fusion proteins conjugated to the core molecule or particle.

15. The fusion protein of claim 1, wherein the extracellular domain of human CD33 comprises the amino acid sequence SEQ ID NO:1, or an amino acid sequence having at least 95% identity to SEQ ID NO:1.

16. The fusion protein of claim 1, wherein the extracellular domain of human CD33 comprises the amino acid sequence SEQ ID NO:1.

* * * * *